US012410245B1

(12) United States Patent
Barker et al.

(10) Patent No.: US 12,410,245 B1
(45) Date of Patent: Sep. 9, 2025

(54) COMPOSITIONS AND METHODS FOR DETECTING AND REGULATING FIBRONECTIN-INTEGRIN INTERACTION AND SIGNALING

(71) Applicants: University of Virginia Patent Foundation, Charlottesville, VA (US); Georgia Tech Research Corporation, Atlanta, GA (US)

(72) Inventors: Thomas H. Barker, Charlottesville, VA (US); Leandro Moretti, Charlottesville, VA (US); Lizhi Cao, Acton, MA (US); John Nicosia, Atlanta, GA (US)

(73) Assignees: University of Virginia Patent Foundation; Georgia Tech Research Corporation

( * ) Notice: Subject to any disclaimer, the term of this patent is extended or adjusted under 35 U.S.C. 154(b) by 0 days.

(21) Appl. No.: 17/823,800

(22) Filed: Aug. 31, 2022

Related U.S. Application Data

(62) Division of application No. 16/457,393, filed on Jun. 28, 2019, now abandoned.

(60) Provisional application No. 62/690,992, filed on Jun. 28, 2018.

(51) Int. Cl.
| *C07K 16/46* | (2006.01) |
| *C07K 16/00* | (2006.01) |
| *C07K 16/18* | (2006.01) |
| *C40B 20/04* | (2006.01) |
| *C40B 40/10* | (2006.01) |
| *G01N 33/563* | (2006.01) |

(52) U.S. Cl.
CPC .............. *C07K 16/18* (2013.01); *C40B 20/04* (2013.01); *C40B 40/10* (2013.01); *G01N 33/563* (2013.01); *C07K 2317/565* (2013.01); *C07K 2317/622* (2013.01); *C07K 2319/02* (2013.01); *C07K 2319/21* (2013.01)

(58) Field of Classification Search
None
See application file for complete search history.

(56) References Cited

U.S. PATENT DOCUMENTS

| 4,554,101 A | 11/1985 | Hopp |
| 4,816,567 A | 3/1989 | Cabilly et al. |
| 4,946,778 A | 8/1990 | Ladner et al. |
| 4,975,369 A | 12/1990 | Beavers et al. |
| 5,001,065 A | 3/1991 | Larrick et al. |
| 5,075,431 A | 12/1991 | Shively et al. |
| 5,081,235 A | 1/1992 | Shively et al. |
| 5,169,939 A | 12/1992 | Gefter et al. |
| 5,202,238 A | 4/1993 | Fell, Jr. et al. |
| 5,204,244 A | 4/1993 | Fell et al. |
| 5,225,539 A | 7/1993 | Winter |
| 5,231,026 A | 7/1993 | Chang |
| 5,292,867 A | 3/1994 | Chang |
| 5,354,847 A | 10/1994 | Liu et al. |
| 5,436,157 A | 7/1995 | Herr et al. |
| 5,472,693 A | 12/1995 | Gourlie et al. |
| 5,482,856 A | 1/1996 | Fell, Jr. et al. |
| 5,491,088 A | 2/1996 | Hellstrom et al. |
| 5,500,362 A | 3/1996 | Robinson et al. |
| 5,502,167 A | 3/1996 | Waldmann et al. |
| 5,530,101 A | 6/1996 | Queen et al. |
| 5,571,894 A | 11/1996 | Wels et al. |
| 5,585,089 A | 12/1996 | Queen et al. |
| 5,587,458 A | 12/1996 | King et al. |
| 5,641,870 A | 6/1997 | Rinderknecht et al. |
| 5,693,761 A | 12/1997 | Queen et al. |

(Continued)

FOREIGN PATENT DOCUMENTS

| EP | 3 539 992 | 9/2019 |
| WO | WO 1992/02190 | 2/1992 |

(Continued)

OTHER PUBLICATIONS

Bachman, Haylee N,. Exploring Fibronectin's Integrin Binding Domain Effects on Lung Fibroblast Integrin Specificity and Downstream Phenotypic Differences. Dissertation. pp. 1-169. Georgia Institute of Technology Dec. 2017 (Year: 2017).*
Addgene (2017) Over-Agar Antibiotic Plating. Basic Molecular Biology Protocol available from the website of Addgene of Watertown, Massachusetts, United States of America.
Aota et al. (1994) The Short Amino Acid Sequence Pro-His-Ser-Arg-Asn in Human Fibronectin Enhances Cell-Adhesive Function. J Biol Chem 269:24756-247561.
Arimori et al. (2017) Fv-clasp: An Artificially Designed Small Antibody Fragment with Improved Production Compatibility, Stability, and Crystallizability. Structure 25:1611-1622.
Brown et al. (2011) Guiding Epithelial Cell Phenotypes with Engineered Integrin-Specific Recombinant Fibronectin Fragments. Tissue Eng, Part A 17:139-50.
Brown et al. (2015) Integrin alpha3beta1 Binding to Fibronectin Is Dependent on the Ninth Type III Repeat. J Biol Chem 290:25534-25547.

(Continued)

*Primary Examiner* — Maher M Haddad
(74) *Attorney, Agent, or Firm* — Jenkins, Taylor & Hunt, P.A.

(57) ABSTRACT

Provided are antibodies that include amino acid sequences of SEQ ID NOs: 2, 4, and 6-12, or amino acid sequences that are about 95% identical thereto, and fragments thereof. Also provided are scFv peptides that include a $V_H$ segment having a first amino acid sequence of amino acids 4-113 of any one of SEQ ID NOs: 2 and 8-12, a $V_L$ segment having a second amino acid sequence having amino acids 113-237 of SEQ ID NOs. 2 and 8-12, or both; nucleic acids encoding the same; methods for using the same to detect and/or target conformational states of FN in samples; methods for treating diseases and/or disorders and/or for meliorating at least one symptom of consequence of a disease or disorder associated with abnormal expression of a force-induced conformational state of FN in subjects; and methods for screening for compounds having selective binding activities for conformational states of FN.

8 Claims, 18 Drawing Sheets
(16 of 18 Drawing Sheet(s) Filed in Color)
Specification includes a Sequence Listing.

(56) References Cited

U.S. PATENT DOCUMENTS

| | | | |
|---|---|---|---|
| 5,693,762 | A | 12/1997 | Queen et al. |
| 5,712,120 | A | 1/1998 | Rodriguez et al. |
| 5,714,350 | A | 2/1998 | Co et al. |
| 5,766,886 | A | 6/1998 | Studnicka et al. |
| 5,770,196 | A | 6/1998 | Studnicka |
| 5,777,085 | A | 7/1998 | Co et al. |
| 5,821,123 | A | 10/1998 | Studnicka |
| 5,821,337 | A | 10/1998 | Carter et al. |
| 5,869,619 | A | 2/1999 | Studnicka |
| 5,877,293 | A | 3/1999 | Adair et al. |
| 5,886,152 | A | 3/1999 | Nakatani et al. |
| 5,895,205 | A | 4/1999 | Werner et al. |
| 5,929,212 | A | 7/1999 | Jolliffe et al. |
| 6,054,297 | A | 4/2000 | Carter et al. |
| 6,180,370 | B1 | 1/2001 | Queen et al. |
| 6,407,213 | B1 | 6/2002 | Carter et al. |
| 6,479,284 | B1 | 11/2002 | Marasco et al. |
| 6,548,640 | B1 | 4/2003 | Winter |
| 6,632,927 | B2 | 10/2003 | Adair et al. |
| 6,639,055 | B1 | 10/2003 | Carter et al. |
| 6,677,436 | B1 | 1/2004 | Sato et al. |
| 6,750,325 | B1 | 6/2004 | Jolliffe et al. |
| 6,797,492 | B2 | 9/2004 | Daugherty et al. |
| 7,060,808 | B1 | 6/2006 | Goldstein et al. |
| 7,906,625 | B2 | 3/2011 | Shen et al. |
| 8,398,980 | B2 | 3/2013 | Kano et al. |
| 8,436,150 | B2 | 5/2013 | Ng et al. |
| 8,796,439 | B2 | 8/2014 | Pfeifer et al. |
| 10,253,111 | B2 | 4/2019 | Elias et al. |
| 10,513,562 | B2 | 12/2019 | Takagi |
| 2002/0034765 | A1 | 3/2002 | Daugherty et al. |
| 2003/0017534 | A1 | 1/2003 | Buelow et al. |
| 2003/0022244 | A1 | 1/2003 | Solomon et al. |
| 2003/0153043 | A1 | 8/2003 | Carr et al. |
| 2004/0253645 | A1 | 12/2004 | Daugherty et al. |
| 2006/0073137 | A1 | 4/2006 | Adair et al. |
| 2018/0298087 | A1 | 10/2018 | Gruber |
| 2018/0312588 | A1 | 11/2018 | Wiltzius et al. |
| 2018/0346564 | A1 | 12/2018 | Eguchi et al. |
| 2019/0151448 | A1 | 5/2019 | Abel et al. |
| 2021/0355199 | A1 | 11/2021 | Barker et al. |

FOREIGN PATENT DOCUMENTS

| | | |
|---|---|---|
| WO | WO 1993/16185 | 8/1993 |
| WO | WO 2007/019107 | 2/2007 |
| WO | WO 2007/030652 | 3/2007 |
| WO | WO 2007/089798 | 8/2007 |
| WO | WO 2008/060374 | 5/2008 |
| WO | WO 2018/088403 | 5/2018 |

OTHER PUBLICATIONS

Cao et al. (2012) Phage-Based Molecular Probes that Discriminate Force-Induced Structural States of Fibronectin in vivo. Proc Natl Acad Sci U S A 109:7251-7256.

Cao (2014) Development of Conformation-Sensitive Probes to Fibronectin for ECM Targeting and Imaging of Fibrosis. Dissertation. Georgia Institute of Technology, pp. 1-127.

Cao et al. (2017) Detection of an Integrin-Binding Mechanoswitch within Fibronectin during Tissue Formation and Fibrosis. ACS Nano 11:7110-7117.

Carisey et al. (2013) Vinculin Regulates the Recruitment and Release of Core Focal Adhesion Proteins in a Force-Dependent Manner. Curr Biol 23:271-281.

Chandler et al. (2011) Adipose Progenitor Cells Increase Fibronectin Matrix Strain and Unfolding in Breast Tumors. Phys Biol 8:015008.

Chen et al. (2013) Fusion Protein Linkers: Property, Design and Functionality. Adv Drug Deliv Rev 65:1357-1369.

Craig et al. (2001) Comparison of the Early Stages of Forced Unfolding for Fibronectin Type III Modules. Proc Natl Acad Sci U S A 98:5590-5595.

Craig et al. (2004) Tuning the Mechanical Stability of Fibronectin Type III Modules Through Sequence Variations. Structure 2004, 12, 21-30.

Craig et al. (2008) Effect of Linker and Spacer on the Design of a Fibronectin-Mimetic Peptide Evaluated via Cell Studies and AFM Adhesion Forces. Langmuir 24:10282-10292.

Cuccuru et al. (2012) A simple, rapid and inexpensive technique to bind small peptides to polystyrene surfaces for immunoenzymatic assays. J Immunol Methods 382:216-219.

Datta et al. (2011) Novel therapeutic approaches for pulmonary fibrosis. Br J Pharmacol 163:141-172.

De Kruif et al. (1995) Selection and application of human single chain Fv antibody fragments from a semi-synthetic phage antibody display library with designed CDR3 regions. J Mol Biol 248:97-105.

Gallant et al. (2005) Cell Adhesion Strengthening: Contributions of Adhesive Area, Integrin Binding, and Focal Adhesion Assembly. Mol Biol Cell 16(9):4329-4340.

Garcia et al. (2002) Distinct Activation States of alpha5beta1 Integrin Show Differential Binding to RGD and Synergy Domains of Fibronectin. Biochemistry 41:9063-9069.

Gee et al. (2008) Fibronectin Unfolding Revisited: Modeling Cell Traction-Mediated Unfolding of the Tenth Type-III Repeat. PLoS One 3:e2373.

Grashoff et al. (2010) Measuring Mechanical Tension Across Vinculin Reveals Regulation of Focal Adhesion Dynamics. Nature 466:263-266.

Grodberg & Dunn (1988) OmpT encodes the *Escherichia coli* outer membrane protease that cleaves T7 RNA polymerase during purification. J Bacteriol 170:1245-1258.

Henderson et al. (2013) Targeting of AlphaV Integrin Identifies a Core Molecular Pathway that Regulates Fibrosis in Several Organs. Nat Med 19:1617-1624.

Hubbard et al. (2016) Fibronectin Fiber Extension Decreases Cell Spreading and Migration. J Cell Physiol 231:1728-1736.

Huse et al. (1989) Generation of a large combinatorial library of the immunoglobulin repertoire in phage lambda. Science 246:1275-1281.

Huston et al. (1988) Protein engineering of antibody binding sites: recovery of specific activity in an anti-digoxin single-chain Fv analogue produced in *Escherichia coli*. Proc Natl Acad Sci U S A 85:5879-5883.

Izbicki et al. (2002) Time Course of Bleomycin-Induced Lung Fibrosis. Int J Exp Pathol 83:111-119.

Jiang et al. (1994) Astrocytes Modulate Retinal Vasculogenesis: Effects on Fibronectin Expression. J Cell Sci 107:2499-2508.

King et al. (2011) Idiopathic pulmonary fibrosis. Lancet 378(9807):1949-1961.

Koenig et al. (2017) Mutational landscape of antibody variable domains reveals a switch modulating the interdomain conformational dynamics and antigen binding. Proc Natl Acad Sci U S A 114:486-495.

Krammer et al. (1999) Forced Unfolding of the Fibronectin Type III Module Reveals a Tensile Molecular Recognition Switch. Proc Natl Acad Sci U S A 96:1351-1356.

Kuddannaya et al. (2013) Surface Chemical Modification of Poly(dimethylsiloxane) for the Enhanced Adhesion and Proliferation of Mesenchymal Stem Cells. ACS Appl Mater Interfaces 5:9777-9784.

Lawson et al. (2005) Increased and Prolonged Pulmonary Fibrosis in Surfactant Protein C-Deficient Mice Following Intratracheal Bleomycin. Am J Pathol 167:1267-1277.

Lemmon et al. (2011) Probing the Folded State of Fibronectin Type III Domains in Stretched Fibrils by Measuring Buried Cysteine Accessibility. J Biol Chem 286:26375-26382.

Li et al. (2005) Mechanical Unfolding Intermediates Observed by Single-Molecule Force Spectroscopy in a Fibronectin Type III Module. J Mol Biol 345:817-826.

Little et al. (2008) Assay to Mechanically Tune and Optically Probe Fibrillar Fibronectin Conformations from Fully Relaxed to Breakage. Matrix Biol 27:451-461.

(56) References Cited

OTHER PUBLICATIONS

Mardon & Grant (1994) The Role of the Ninth and Tenth Type III Domains of Human Fibronectin in Cell Adhesion. FEBS Lett 340:197-201.
Markowski et al. (2012) Directing Epithelial to Mesenchymal Transition Through Engineered Microenvironments Displaying Orthogonal Adhesive and Mechanical Cues. J Biomed Mater Res, Part A 100:2119-2127.
Martino et al. (2009) Controlling Integrin Specificity and Stem Cell Differentiation in 2D and 3D Environments Through Regulation of Fibronectin Domain Stability. Biomaterials 30:1089-1097.
Moek et al. (2017) Theranostics Using Antibodies and Antibody-Related Therapeutics. J Nucl Med Off Publ Soc Nucl Med 58:83S-90S.
Moretti (2016) Approaches to Improve Expression and Specificity of an Antibody Probe Against Fibronectin. Thesis, Georgia Institute of Technology, p. 1-66.
Morton & Myszka (1998) Kinetic analysis of macromolecular interactions using surface plasmon resonance biosensors. Methods Enzymol 295:268-294.
Morton et al. (1995) Interpreting complex binding kinetics from optical biosensors: a comparison of analysis by linearization, the integrated rate equation, and numerical integration. Anal Biochem 227(1):176-185.
Mould et al. (1997) Defining the Topology of Integrin alpha5beta1-Fibronectin Interactions Using Inhibitory Anti-alpha5 and Anti-beta1 Monoclonal Antibodies. Evidence that the Synergy Sequence of Fibronectin is Recognized by the Amino-Terminal Repeats of the alpha5 Subunit. J Biol Chem 272:17283-17292.
National Heart, Lung, and Blood Institute. Idiopathic Pulmonary Fibrosis, available from the website of the National Heart, Lung, and Blood Institute (NHLBI).
Office Action (Restriction Requirement) corresponding to U.S. Appl. No. 16/457,393 dated Jun. 29, 2020.
Office Action corresponding to U.S. Appl. No. 16/457,393 dated Jul. 29, 2021.
Offord & Grens (2018) Directed Evolution, Phage Display Nab Chemistry Nobel. The Scientist Magazine, October 3, 3018.
Pankov & Yamada (2002) Fibronectin at a glance. J Cell Sci 115:3861-3863.
Patan (2004) Vasculogenesis and Angiogenesis. Cancer Treat Res 117:3-32.
Pitulescu et al. (2010) Inducible Gene Targeting in the Neonatal Vasculature and Analysis of Retinal Angiogenesis in Mice. Nat Protoc 5:1518-1534.
Pulmonary Fibrosis Foundation (2018) What is Pulmonary Fibrosis. available from the website of the Pulmonary Fibrosis Foundation, Chicago, Illinois, United States of America.
Raghu & Mikacenic (2018) Pathogenesis of idiopathic pulmonary fibrosis. Available from the website of UPTODATE®, Wolters Kluwer, Riverwoods, Illinois, United States of America.
Rosano & Ceccarelli (2014) Recombinant protein expression in *Escherichia coli*: advances and challenges. Front Microbiol 5:Article 172.
Ruoslahti & Pierschbacher (1987) New Perspectives in Cell Adhesion: RGD and Integrins. Science 238:491-497.
Schoonooghe (2012) Engineering and Expression of Bloody and Tribody Constructs in Mammalian Cells and in the Yeast *Pichia pastoris*. Methods Mol Biol Actions. 899:157-75.
Schornberg et al. (2009) Alpha5beta1-Integrin Controls Ebolavirus Entry by Regulating Endosomal Cathepsins. Proc Natl Acad Sci U S A 106:8003-8008.
Shukla et al. (2013) Structure of Active Betaarrestin-1 Bound to a G-Protein-Coupled Receptor Phosphopeptide. Nature 497:137-141.
Sims et al. (1993) A humanized CD18 antibody can block function without cell destruction. J Immunol 151:2296-2308.
Smith et al. (2007) Force-Induced Unfolding of Fibronectin in the Extracellular Matrix of Living Cells. PLoS Biol 5:2243-2254.
Tobias (2014) Biomolecular binding kinetic assays on the octet platform. Forte Bio Appl Note 14:1-21.
Trafton (2010) Explained: Directed evolution. Speeding up protein evolution in the lab can yield useful molecules that nature never intended. MIT News May 13, 2010. Massachusetts Institute of Technology, Cambridge, Massachusetts, United States of America.
Tuszynski et al. (1988) Thrombospondin promotes platelet aggregation. Blood 72:109-115.
Van der Walle et al. (2002) Novel Mutant Human Fibronectin FIII9-10 Domain Pair with Increased Conformational Stability and Biological Activity. Protein Eng 15:1021-1024.
Verhoeyen et al. (1988) Reshaping human antibodies: grafting an antilysozyme activity. Science 239:1534-1536.
Zhu et al. (2008) Structure of a Complete Integrin Ectodomain in a Physiologic Resting State and Activation and Deactivation by Applied Forces. Mol Cell 32:849-861.
Office Action corresponding to U.S. Appl. No. 16/457,393 dated Dec. 24, 2020.

\* cited by examiner

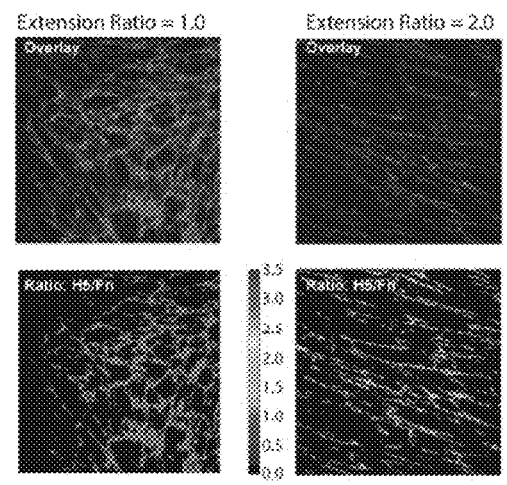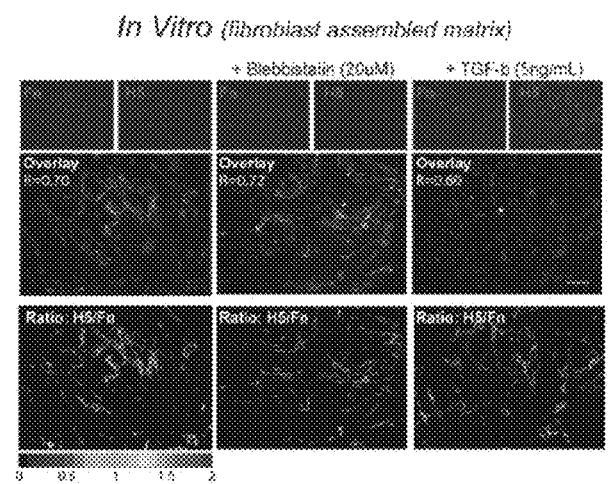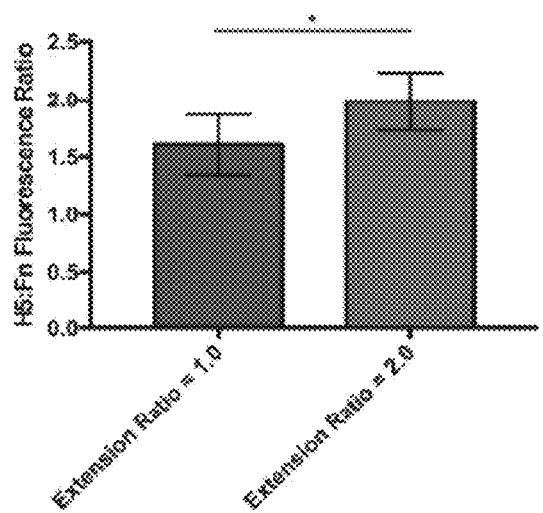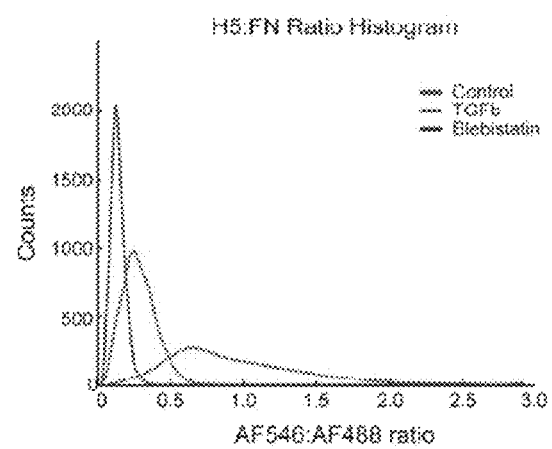
FIG. 5B
FIG. 5C

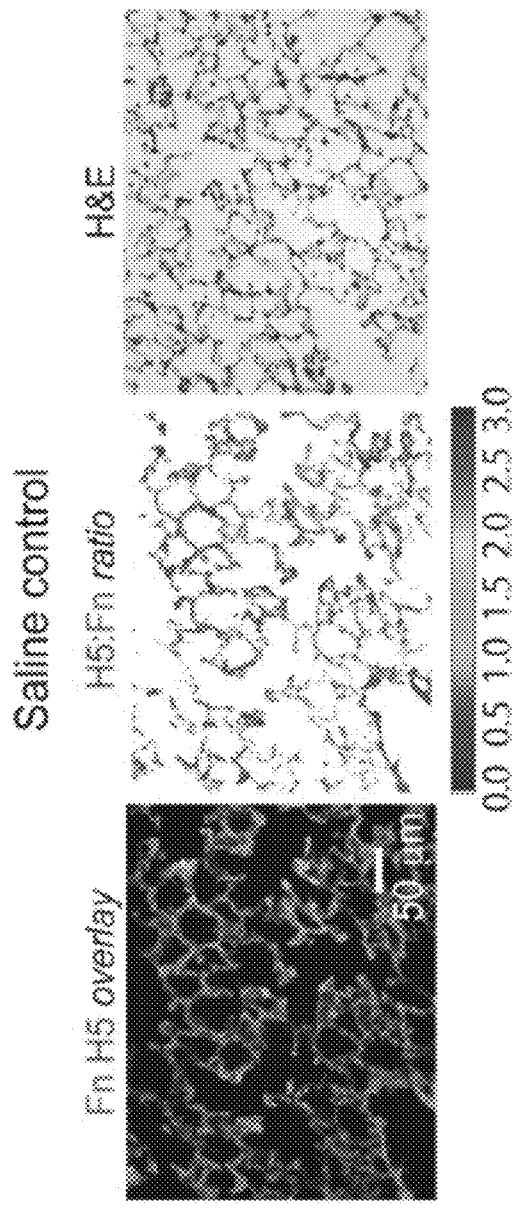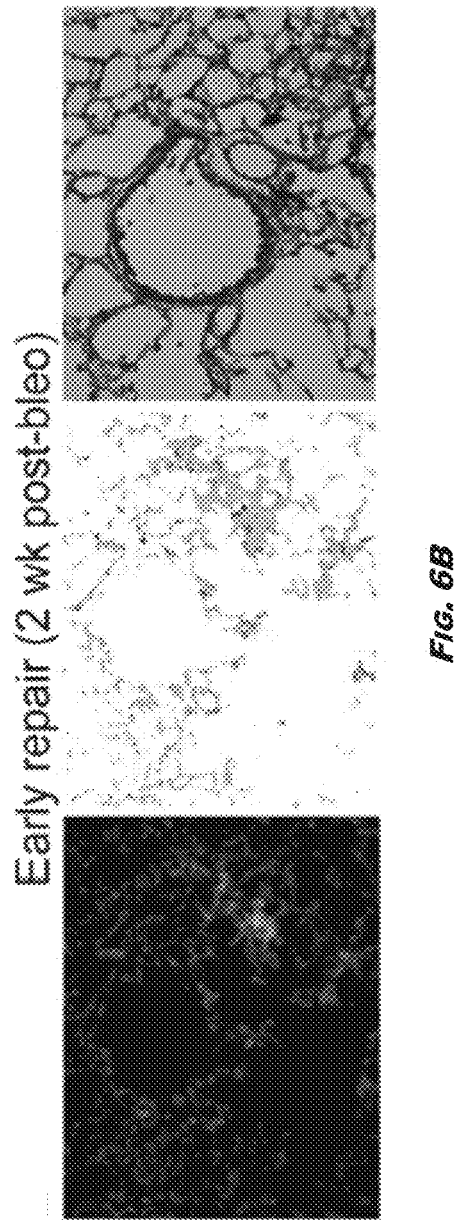
FIG. 6A
FIG. 6B

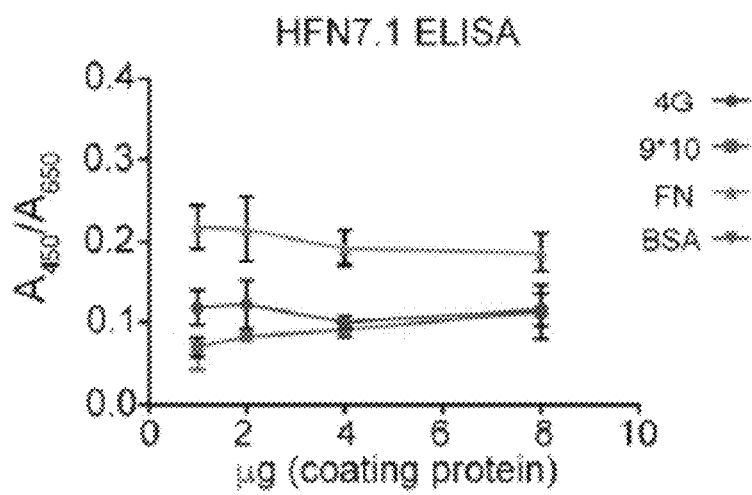
*FIG. 9I*
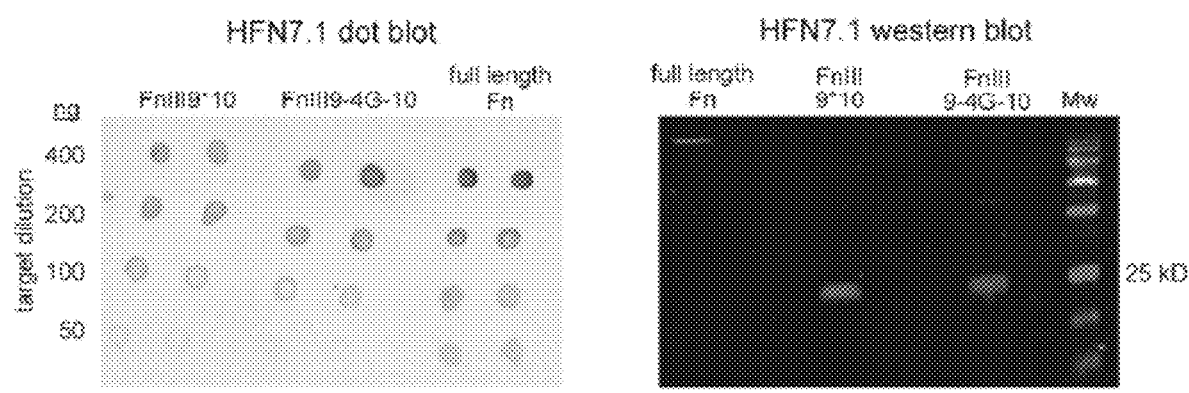
*FIG. 9J*  *FIG. 9K*

9*10     4G     Clones plated

COMPOSITIONS AND METHODS FOR DETECTING AND REGULATING FIBRONECTIN-INTEGRIN INTERACTION AND SIGNALING

CROSS REFERENCE TO RELATED APPLICATIONS

This application is a divisional of U.S. patent application Ser. No. 16/457,393, filed Jun. 28, 2019 (now pending), which itself claims the benefit of U.S. Provisional Patent Application Ser. No. 62/690,992, filed Jun. 28, 2018, the disclosure of each of which is incorporated herein by reference in its entirety.

GOVERNMENT INTEREST

This invention was made with government support under Grant No. HL127283 awarded by The National Institutes of Health. The government has certain rights in the invention.

REFERENCE TO SEQUENCE LISTING XML SUBMITTED ELECTRONICALLY

The content of the Sequence Listing XML filed using Patent Center as an XML file (Name: 3062_52_3_DIV.xml; Size: 51,315 bytes; and Date of Creation: Aug. 31, 2022) is incorporated herein by reference in its entirety.

TECHNICAL FIELD

The presently disclosed subject matter relates to compositions and methods for detecting and regulating fibronectin-integrin interaction and signaling. In particular, the presently disclosed subject matter relates to compositions and methods useful for targeting of a mechanically exposed cryptic site within fibronectin's integrin binding domain.

BACKGROUND

The extracellular matrix (ECM) forms the complex niche of structural elements surrounding cells in vivo. Cells interact with and are instructed by the ECM via cellular structures known as focal adhesions, large protein complexes composed of transmembrane receptors (integrins) and intracellular adaptor proteins that mechanically couple the cell's cytoskeleton to fibrillar ECM proteins such as fibronectin (Fn). Protein-protein interactions within focal adhesions are dynamic; mechanical forces play important roles for focal adhesion maturation and development, as well as for force-sensitive cell signaling via mechanosensory proteins. Conformations of both intracellular focal adhesion constituents (e.g., vinculin, integrins) as well as extracellular components (e.g., Fn) are altered by forces transmitted to and from the ECM. In the latter case, Fn within the ECM exhibits distinct but undefined altered structural states in response to cellular forces both in vitro and in vivo.

Fn comprises three types of tandem repeating units, each containing two antiparallel β-sheets. Type I and II repeats are structurally stabilized by disulfide bonds, whereas type III repeats are stabilized only by hydrogen bonding and Van der Waals forces, making them sensitive to unfolding due to physiologically relevant forces. These findings, when coupled with the active role of Fn's 9th and 10th type III repeats (FnIII9-10) in mediating integrin-specific interactions, inspired the theory that mechanical forces could trigger a "switch" in the integrin-binding profile of Fn. Fn-integrin interactions are known to drive critical cell behaviors and are mediated primarily through the canonical and promiscuous integrin binding sequence Arg-Gly-Asp (RGD) within the 10th type III repeat. A subset of integrins, including integrin α5β1, is additionally dependent on the sequence motif PHSRN (SEQ ID NO: 7) within the neighboring 9th type III repeat. Integrin specificity to Fn can be modulated in vitro by altering the structural stability of the integrin binding domain (i.e., the 9th and 10th type III repeats) via directed mutation resulting in the regulation of developmentally and pathologically relevant cell differentiation pathways, and, importantly, cellular responses to microenvironmental mechanics (e.g., stiffness). Despite these findings, the integrin switch theory and its potential relevance to biological processes in vivo remains undefined.

There is a long felt need in the art for compositions and methods useful for detecting and regulating the Fn integrin switch and for diagnosing, distinguishing, treating, and preventing diseases and disorders associated with this pathway. The presently disclosed subject matter addresses these needs.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides isolated and purified antibodies that comprise an amino acid sequence selected from the group consisting of SEQ ID NOs: 2, 4, and 6-12, a fragment thereof, or an antibody having an amino acid sequence that is approximately 95% identical to the sequence of any one of SEQ ID NOs: 2, 4, and 6-12, or a fragment thereof. In some embodiments, the amino acid sequence comprises at least one modification selected from the group consisting of an amino acid deletion, an amino acid addition, an amino acid substitution, and combinations thereof. In some embodiments, the antibody or fragment thereof comprises an scFv fragment. In some embodiments, the scFv fragment is mammalian. In some embodiments, the scFv fragment is humanized.

In some embodiments, the isolated and purified antibody, or fragment or homolog thereof, comprises a heavy chain CDR1 of sequence SYAMS (SEQ ID NO: 24), a heavy chain CDR2 of sequence DIYDGGGTNYADSVKG (SEQ ID NO: 25), a heavy chain CDR3 of sequence TADNFY (SEQ ID NO: 26) or TADNFD (SEQ ID NO: 27), a light chain CDR1 of sequence RASQSISSYLN (SEQ ID NO: 28), a light chain CDR2 of sequence AASTLQS (SEQ ID NO: 29), and a light chain CDR3 of sequence QQANSAPTT (SEQ ID NO: 30).

In some embodiments, the isolated and purified antibody, or fragment or homolog thereof, comprises a modification at its N-terminus, its C-terminus, or both. In some embodiments, the modification comprises addition of a peptide tag, a SARAH domain, or a combination thereof. In some embodiments, the tag comprises a his tag, a myc tag, a VSV tag, an HA tag, a SortaseA tag, a PelB sequence, or any combination of one or more thereof. In some embodiments, the SARAH domain comprises a sequence selected from the group consisting of SEQ ID NOs: 19-23.

The presently disclosed subject matter also provides in some embodiments isolated and purified nucleic acid sequences encoding the antibodies and fragments disclosed herein.

The presently disclosed subject matter also provides in some embodiments single chain variable fragment (scFv) peptides. In some embodiments, the scFv peptides comprise a $V_H$ segment comprising a first amino acid sequence selected from the group consisting of amino acids 4-113 of any one of SEQ ID NOs: 2 and 8-12, a $V_L$ segment comprising a second amino acid sequence selected from the group consisting of amino acids 113-237 of SEQ ID NOs. 2 and 8-12, or a combination thereof. In some embodiments, the $V_H$ segment and $V_L$ segment are coupled together with a linker peptide, optionally a glycine-rich peptide, and further optionally a glycine-rich peptide comprising a concatemer of one, two, or three copies of SEQ ID NO: 17, a concatemer of one, two, or three copies of SEQ ID NO: 18, or a mixture of one, two, or three copies of SEQ ID NO: 17 and one, two, or three copies of SEQ ID NO: 18. In some embodiments, the scFv peptides further comprises at least two pairs of the $V_H$ segment and $V_L$ segment, wherein the at least two pairs are linked to form a multivalent scFv. In some embodiments, the scFv peptide is present in the pharmacologically acceptable carrier. In some embodiments, the scFv peptide is grafted into a human or humanized antibody.

The presently disclosed subject matter also provides in some embodiments recombinant nucleic acids. In some embodiments, the recombinant nucleic acids comprise a first nucleic acid segment encoding a $V_H$ segment having a first amino acid sequence selected from the group consisting of amino acids 4-113 of any one of SEQ ID NOs: 2 and 8-12, a second nucleic acid segment encoding a $V_L$ segment having a second amino acid sequence selected from the group consisting of amino acids 113-227 of SEQ ID NOs. 2 and 8-12, or a combination thereof, wherein the first and second segments are optionally present in a same reading frame. In some embodiments, the recombinant nucleic acids further comprise a third nucleic acid segment encoding a linker peptide coupling together the first and second segments in frame. In some embodiments, the recombinant nucleic acids further comprise one or more additional nucleic acid segments that encode one or more subsequences of an intact antibody, such that the recombinant nucleic acid encodes a recombinant intact antibody.

The presently disclosed subject matter also provides in some embodiments methods for targeting conformational states of fibronectin (FN) in samples, optionally biological samples isolated from or present within a subject. In some embodiments, the methods comprise contacting a sample with a composition having a selective binding activity for a conformational state of FN comprising FnIII9-4G-10 (4G), whereby the conformational state is targeted. In some embodiments, the sample comprises or is suspected to comprise a tissue undergoing tissue repair, a tissue that is diseased, a tissue that suffers from a disorder, or any combination thereof.

The presently disclosed subject matter also provides in some embodiments methods for detecting conformational states of fibronectin (FN) in samples. In some embodiments, the methods comprise contacting a sample with a composition having a selective binding activity for a conformational state of FN comprising FnIII9-4G-10 (4G); and detecting the binding of the composition, whereby the conformational state of FN is detected. In some embodiments, the sample comprises or is suspected to comprise a tissue undergoing tissue repair, a tissue that is diseased, a tissue that suffers from a disorder, or a combination thereof. In some embodiments, the sample comprises or is suspected to comprise a pathologic extracellular matrix (ECM). In some embodiments, the sample comprises or is suspected to comprise tumor stroma, a fibrotic ECM, or a combination thereof. In some embodiments, detecting the binding of the composition comprises detecting a binding ratio of composition to FN. In some embodiments, detecting the binding of the composition comprises distinguishing normal from diseased tissue. In some embodiments, detecting the binding of the composition comprises determining severity of fibrosis in the sample. In some embodiments, detecting the binding of the composition comprises detecting a transient, force-induced conformational change in FN. In some embodiments, detecting the binding of the composition comprises extracting structural information for an ECM in the sample. In some embodiments, extracting structural information for an ECM in the sample comprises delineating regions of high ECM strain. In some embodiments, the high ECM strain is associated with enhanced αv integrin binding character.

In some embodiments, the methods further comprise determining a type of treatment to be administered to the subject based on the detecting of the binding of the composition.

The presently disclosed subject matter also provides in some embodiments methods for treating diseases and/or disorders in subjects. In some embodiments, the methods comprise administering to a subject in need there of a therapeutically effective amount of a composition having a selective binding activity for a conformational state of FN comprising FnIII9-4G-10 (4G), whereby treatment is accomplished. In some embodiments, the disease and/or disorder has a characteristic selected from the group consisting of a tissue undergoing tissue repair, a tissue that is diseased, a tissue that suffers from a disorder, and any combination thereof. In some embodiments, the characteristic is a pathologic extracellular matrix (ECM). In some embodiments, the characteristic is tumor stroma, a fibrotic ECM, or a combination thereof.

In some embodiments of the presently disclosed methods, the composition having a selective binding activity for a conformational state of FN comprising FnIII9-4G-10 (4G) is an isolated and purified antibody comprising an amino acid sequence selected from the group consisting of SEQ ID NOs: 2, 4, and 6-12, a fragment thereof, or an antibody have a sequence approximately 95% identical to a sequence of SEQ ID NOs: 2, 4, and 6-12, or a fragment thereof. In some embodiments, the amino acid sequence comprises at least one modification selected from the group consisting of an amino acid deletion, an amino acid addition, an amino acid substitution, and combinations thereof. In some embodiments, the antibody or fragment thereof comprises a scFv fragment. In some embodiments, the scFv fragment is mammalian. In some embodiments, the scFv fragment is humanized.

The presently disclosed subject matter also provides in some embodiments methods for screening for compounds having selective binding activities for conformational states of FN comprising FnIII9-4G-10 (4G). In some embodiments, the methods comprise providing a sample comprising a conformational state of FN comprising FnIII9-4G-10 (4G); contacting the sample with a candidate compound; and detecting binding of the candidate compound to the sample.

In some embodiments, the candidate compound is a member of a library of compounds. In some embodiments, the candidate compound is a small molecule or an antibody. In some embodiments, the conformational state of FN is a force-induced conformational change in Fn.

The presently disclosed subject matter also provides in some embodiments compounds identified by the presently disclosed methods.

The presently disclosed subject matter also provides in some embodiments methods for treating diseases and/or disorder in subjects comprising administering to a subject in need thereof a therapeutically effective amount of a composition comprising the scFv peptide in accordance with the presently disclosed subject matter, whereby treatment is accomplished.

The presently disclosed subject matter also provides in some embodiments methods for ameliorating at least one symptom of consequence of a disease or disorder associated with abnormal expression of a force-induced conformational state of FN comprising FnIII9-4G-10 (4G) in a subject. In some embodiments, the methods comprise administering to a subject in need thereof a therapeutically effective amount of a composition comprising the scFv peptide in accordance with the presently disclosed subject matter, wherein at least one symptom of consequence of a disease or disorder associated with abnormal expression of a force-induced conformational state of FN comprising FnIII9-4G-10 (4G) is ameliorated.

In some embodiments of the therapeutic methods, the disease or disorder is associated with a tissue undergoing tissue repair, a tissue that is diseased, a tissue that suffers from a disorder, or any combination thereof. In some embodiments, the disease or disorder is associated with a pathologic extracellular matrix (ECM). In some embodiments, the disease or disorder is associated with tumor stroma, a fibrotic ECM, or a combination thereof.

The presently disclosed subject matter also provides in some embodiments single chain variable fragment (scFv) peptide comprising a heavy chain CDR1 of sequence SYAMS (SEQ ID NO: 24), a heavy chain CDR2 of sequence DIYDGGGTNYADSVKG (SEQ ID NO: 25), a heavy chain CDR3 of sequence TADNFY (SEQ ID NO: 26) or TADNFD (SEQ ID NO: 27), a light chain CDR1 of sequence RASQSISSYLN (SEQ ID NO: 28), a light chain CDR2 of sequence AASTLQS (SEQ ID NO: 29), and a light chain CDR3 of sequence QQANSAPTT (SEQ ID NO: 30). In some embodiments, the scFv comprises a $V_H$ segment and a $V_L$ segment coupled together with a linker peptide. In some embodiments, the linker peptide is a glycine-rich peptide. In some embodiments, the glycine-rich peptide comprises a concatemer of one, two, or three copies of SEQ ID NO: 17, a concatemer of one, two, or three copies of SEQ ID NO: 18, or a mixture of one, two, or three copies of SEQ ID NO: 17 and one, two, or three copies of SEQ ID NO: 18. In some embodiments, the scFv peptide further comprises at least two pairs of the $V_H$ segment and $V_L$ segment, wherein the at least two pairs are linked to form a multivalent scFv. In some embodiments, the In some embodiments, the scFv peptide is present in the pharmacologically acceptable carrier. In some embodiments, the scFv peptide is grafted into a human or humanized antibody. In some embodiments, the scFv peptide further comprises a modification at its N-terminus, its C-terminus, or both. In some embodiments, the the modification comprises addition of a peptide tag, a SARAH domain, or a combination thereof. In some embodiments, the tag comprises a his tag, a myc tag, a VSV tag, an HA tag, a SortaseA tag, a PelB sequence, or any combination of one or more thereof. In some embodiments, the tag comprises an amino acid sequence selected from the group consisting of SEQ ID NOs: 31-36. In some embodiment, the SARAH domain comprises a sequence selected from the group consisting of SEQ ID NOs: 19-23.

Accordingly, it is an object of the presently disclosed subject matter to provide compositions and methods for detecting and regulating fibronectin-integrin interaction and signaling. This and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, Figures, and EXAMPLES. Additionally, various aspects and embodiments of the presently disclosed subject matter are described in further detail below.

BRIEF DESCRIPTION OF THE FIGURES

The patent or application file contains at least one drawing executed in color. Copies of this patent or patent application publication with color drawings will be provided by the United States Patent and Trademark Office upon request and payment of the necessary fee.

FIG. 1A is a series of PyMol structure predictions of engineered recombinant fragments of Fn's integrin binding domain. FnIII9*10, represents a stabilized native structure through a Leu-to-Pro point mutation at position 1408. In this conformation, the PHSRN (SEQ ID NO: 7)-to-RGD distance was approximately 36 Å. FnIII9-4G-10 is a mutation of the FnII9*10 variant that contains a 4×Gly insertion between the $9^{th}$ and $10^{th}$ type III repeats. This mutation increased domain separation and the PHSRN (SEQ ID NO: 7)-to-RGD distance to approximately 43 Å. These fragments have been employed in the past to predict potential biological consequences of the theorized integrin switch. FIG. 1B is a series of plots showing SPR binding characterization of integrins α5β1 and αVβ3 to the FnIII9*10 and FnIII9-4G-10 fragments and demonstrating a nearly complete loss of binding of α5β1 upon domain separation whereas αVβ3 binding was predictably unaffected. Black curves show experimental sensogram traces, red curves show computationally fitted data. Equilibrium dissociation constants ($K_D$) are shown above the curves. FIG. 1C is a series of fluorescence micrographs showing that fibroblasts cultured on FnIII9*10 and FnIII9-4G-10 fragments and immunostained for integrin α5 and αv demonstrated the fragments' capabilities of skewing cellular binding toward specific integrins corroborating SPR analysis. Scale bar is 20 μm.

FIG. 3 depicts the strategy employed in the ELISA assay, in which individual scFv antibodies were produced and incubated on both FnIII9*10 and FnIII9-4G-10. Ratio of ELISA signal was used as a metric to assess scFv antibodies with skewed preference in binding one Fn fragment over the other.

FIGS. 5A-5C depict the results of experiments showing that the H5 antibody was capable of discriminating conformational changes of Fn's integrin binding domain (i.e. the integrin switch) in multiple model systems. FIG. 5A is a series of photos (left panel) depicting staining of H5 on in vitro Fn fibers deposited on PDMS membranes and demonstrating the strain-dependent conformation of Fn's integrin binding domain at the listed extension ratios. These data are also summarized in the graph in the right panel. A discrete transition from modest to high binding occurred between an extension ratio of 1.25 and 1.5. N=10, error bars reflect SD, ***p<0.001, one-way ANOVA with Tukey's post-test. FIG. 5B is a series of fluorescence micrographs (top panel) and bar graphs (bottom panel) showing staining of strained or relaxed decelluarized ECM assembled by human foreskin fibroblasts by H5, indicating that the Fn integrin binding domain within complex (anisotropic) Fn-rich ECM underwent a conformational change in response to strain. N=6, error bars reflect SD, *p<0.01, Wilcoxon sum-rank test. FIG. 5C is a series of fluorescence micrographs (top panel) and a plot summarizing the fluorescence micrograph data (bottom panel) demonstrating that the conformation of Fn's integrin binding domain within primary lung fibroblast-laden Fn-rich ECM was sensitive to modulation of fibroblast contractility through agonists (TGF-β) and inhibitors (blebbistatin). Scale bar, 50 μm.

FIGS. 6A-6D are a series of photographs showing that Fn's integrin mechano-switch displayed spatially distinct patterns of activation in a model of resolving lung fibrosis. In FIGS. 6A-6D, mouse lung tissue sections (scale bar=50 μm) were immunostained for H5 (red), Fn (green), and DNA (blue) at the indicated time points post-bleomycin-induced fibrotic injury. In this model, bleomycin induced fibrosis by 14-21 days, and was typically resolved by 56 days. H5:Fn ratio images displaying the heterogeneity of Fn fiber conformation within the ECM at the tissue scale are shown as the middle panel of each of FIGS. 6A-6D, along with H&E staining of corresponding serial section at the same time points (right panel of each of FIGS. 6A-6D). The early repair (FIG. 6B) and fibrotic (FIG. 6C) time points showed areas of higher H5:Fn ratio, indicating the unfolding of Fn's integrin binding domain, perhaps indicative of active fibrosis. By resolution (FIG. 6D), the H5:Fn ratiometric image resembled that of the saline control (FIG. 6A).

FIG. 8A is a photograph of whole mount immunostaining for retinal endothelial cells during post-natal retinal angiogenesis with Tip Cell area and Capillary area (i.e. mature vessels) identified (scale bar=500 μm). FIG. 8B is a series of photographs of the tip cell region (scale bar=50 μm) and FIG. 8C is a series of photographs of mature vessels (scale bar=80 μm) that were immunostained with isolectin B4 (IB4, green) and H5 (red) and anti-Fn (blue) at post-natal day 6. Tip cells and blood vessels were visualized using isolectin B4. H5:Fn ratiometric images were generated for each region. The Tip Cell area (FIG. 8B) showed regions of high H5:Fn ratio, suggestive of endothelial tip cell force generation during angiogenesis. The mature vessel area (FIG. 8C), where forces were predicted to be low, displayed a low H5:Fn ratio.

FIGS. 9A-9K presents the result of experiments showing that the H5 antibody recognized conformational change of the integrin binding domain by binding an epitope specifically on the 9th type III repeat that can be exposed by denaturation. FIGS. 9A and 9B are SPR analysis of binding of H5 antibody to recombinant FnIII9*10 (FIG. 9A) and FnIII9-4G-10 (FIG. 9B) fragments demonstrating the conformation selectivity of its binding. H5 bound preferentially to the molecularly extended conformation. Black lines show experimental sensogram traces, red lines show fitted data. Equilibrium dissociation constants ($K_D$) are shown above the curves. FIG. 9C is a graph of competitive binding of the H5 antibody to FnIII9-4G-10 in the presence of soluble FnIII9 (FnIII6-9) and FnIII10 (FnIII10-14) fragments. FnIII9-4G-10 was immobilized on ELISA plates and the H5 antibody was co-incubated with the indicated soluble Fn fragments prior to incubation with FnIII9-4G-10. N=8 for each group, error bars reflect SEM. FIGS. 9D and 9E depict the results of domain mapping studies performed by SPR using Fn fragments including either the 9th type III repeat (FnIII6-9; FIG. 9B), or the 10th type III repeat (FnIII10-14; FIG. 9C). Binding of H5 was only observed by SPR when fragments including the 9th Fn type III repeat were immobilized, suggesting that the epitope for H5 was located within FnIII9. FIG. 9F is a graph showing the results of ELISA of H5 binding to full-length Fn and Fn fragments. H5 bound increasingly to increasing amounts of surface adsorbed FnIII9-4G-10 to a significantly greater degree than FnIII9*10 or full length Fn at all concentrations (p<0.0001; Two-way ANOVA with Tukey's post-test, N=3). FIGS. 9G and 9H are a Nitrocellulose dot blot (FIG. 9G) and Western blot (FIG. 9H), respectively, of H5 binding to full-length Fn and Fn fragments. Under these denaturing conditions, H5 bound FnIII9-4G-10 and FnIII9*10 to a similar degree. FIGS. 9I-9K are a bar graph of the results of ELISA (FIG. 9I), dot blot (FIG. 9J), and Western blot (FIG. 9K) of HFN7.1, a commercially-available antibody targeting FnIII9-10 (Novus Biologicals, LLC, Centennial, Colorado, United States of America). In the ELISA, HFN7.1 only bound FnIII9-4G-10 to a significantly greater degree than FnIII9*10 at 1 μM (p<0.05) and was not significant at higher concentrations (Two-way ANOVA with Tukey's post-test, N=3). HFN7.1 did not show preferential affinity for FnIII9*10 or FnIII9-4G-10 in the dot blot or Western blot.

FIG. 10A is a bar graph showing inhibition of attachment of human foreskin fibroblasts (HFF) to full length Fn. FIG. 10B is a bar graph showing inhibition of attachment of CHOB2 and CHOB2-αVβ3 cells to full length Fn. FIG. 10C is a bar graph showing inhibition of attachment of integrin α5β1 expressing K562 cells to full length Fn. N=6 for all experiments, error bars are SEM, statistics were performed with one-way ANOVA, with Tukey's post-test, (*: p<0.05; ***: p<0.001).

BRIEF DESCRIPTION OF THE SEQUENCE LISTING

Figure 1A:
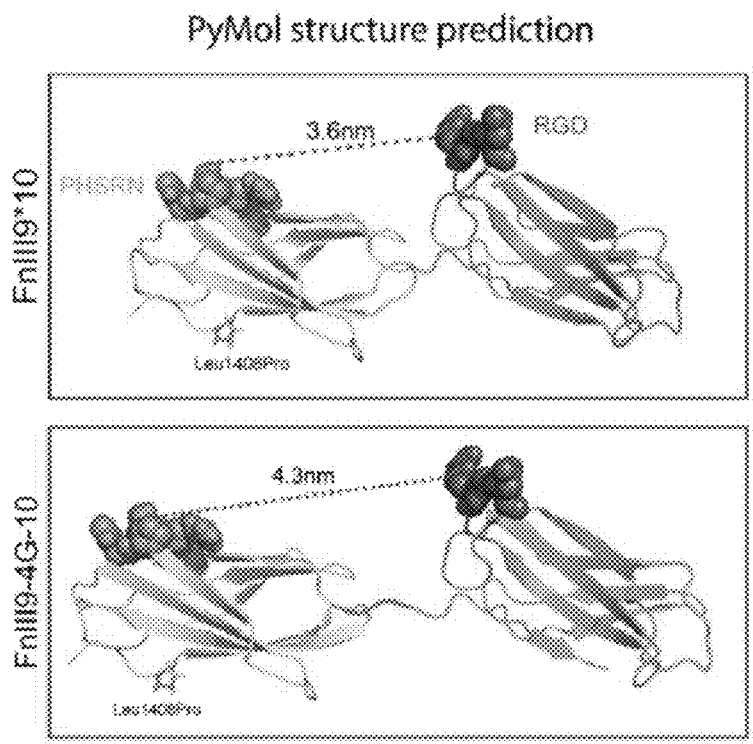
FIGS. 1A-1C depict the results of experiments showing that fibronectin (Fn) strain drives differential integrin affinity.

SEQ ID NOs: 1 and 2 are the nucleic acid and amino acid sequences, respectively, of the H5 scFv.

SEQ ID NOs: 3 and 4 are the nucleic acid and amino acid sequences, respectively, of a PelB+H5 scFv, the pelB sequence (amino acids 1-22 of SEQ ID NO: 4) being added to enhance expression of the construct in E. coli.

SEQ ID NOs: 5 and 6 are the amino acid sequences of exemplary PelB+H5 scFvs, which differ at amino acid 112 (corresponds to amino acid 93 of the H5 sequence of SEQ ID NO: 2), with SEQ ID NO: 5 having a threonine at this amino acid (like the H5 sequence of SEQ ID NO: 2) and SEQ ID NO: 6 having an isoleucine at this amino acid.

SEQ ID NO: 7 is the amino acid sequence of the pentapeptide motif PHSRN that is found in the 9th type III repeat of fibronectin.

SEQ ID NO: 8 is a consensus sequence derived from a comparison and alignment of SEQ ID NOs: 2 and 9-12.

SEQ ID NO: 9 is the amino acid sequence of the R1F8 scFv, in which alanine 96 of SEQ ID NO: 5 was replaced with a threonine.

SEQ ID NO: 10 is the amino acid sequence of the R4B8 scFv, in which aspartic acid 103 in CDR3 of SEQ ID NO: 2 was replaced by a tyrosine.

SEQ ID NO: 11 is the amino acid sequence of the R2G3 scFv, in which proline 41 between CDR1 and CDR2 of SEQ ID NO: 2 was replaced by a serine, and asparagine 73 between CDR2 and CDR3 of SEQ ID NO: 2 was replaced by an aspartic acid.

SEQ ID NO: 12 is the amino acid sequence of the R1H6 scFv, in which leucine 78 between CDR2 and CDR3 of SEQ ID NO: 2 was replaced by a methionine.

SEQ ID NOs: 13 and 14 are the nucleotide sequences of exemplary oligonucleotide primers that can be employed to amplify the full length of the H5 scFv coding sequence.

SEQ ID NOs: 15 and 16 are the nucleotide sequences of exemplary oligonucleotide primers that can be employed to amplify the coding sequence of the heavy chain of the H5 scFv.

SEQ ID NOs: 17 and 18 are the amino acid sequences of an exemplary tetrapeptide linker consisting of four glycine residues and an exemplary pentapeptide linker consisting of a serine residue followed by four glycine residues. It is noted that to create a linker peptide, one, two, three, or more copies of SEQ ID NO: 17 can be combined (i.e., concatemerized), one, two, three, or more copies of SEQ ID NO: 18 can be combined (i.e., concatemerized), or one, two, three, or more copies of SEQ ID NO: 17 can be combined with one, two, three, or more copies of SEQ ID NO: 18.

SEQ ID NOs: 19-23 are the amino acid sequences of exemplary SARAH domains that can be added to the N-terminus, the C-terminus, or both of an scFv of the presently disclosed subject matter.

SEQ ID NOs: 24-30 are the amino acid sequences of heavy chain CDRs 1-3 (SEQ ID NOs: 24-27, respectively, with SEQ ID NOs: 26 and 27 representing heavy chain CDR3 alternatives) and light chain CDRs 1-3 (SEQ ID NOs: 28-30, respectively) of the exemplary scFvs of the presently disclosed subject matter.

SEQ ID NOs: 31-36 are the amino acid sequences of exemplary tags that can be added to the N-terminus, the C-terminus, or both of an scFv of the presently disclosed subject matter. SEQ ID NO: 31 is an exemplary myc tag, SEQ ID NO: 32 is an exemplary VSV tag, SEQ ID NO: 33 is an exemplary His tag, SEQ ID NO: 34 is an exemplary HA tag, SEQ ID NO: 35 is an exemplary SortaseA tag, and SEQ ID NO: 36 is an exemplary PelB tag.

SEQ ID NO: 37 is a linker sequence, NSAAH.

DETAILED DESCRIPTION

General Considerations

Fibronectin (Fn) is an extracellular matrix protein that orchestrates complex cell adhesion and signaling through cell surface integrin receptors during tissue development, remodeling, and disease, such as fibrosis. Fn is sensitive to mechanical forces in its tandem type III repeats resulting in extensive molecular elongation. As such, it has long been hypothesized that cell- and tissue-derived forces may activate an "integrin switch" within the critical integrin binding 9th and 10th type III repeats—conferring differential integrin binding specificity leading to differential cell responses. Yet, no direct evidence exists to prove the hypothesis nor demonstrate the physiological existence of the switch. Provided in accordance with the presently disclosed subject matter is direct experimental evidence for the Fn integrin switch both in vitro and ex vivo using a scFv engineered to detect the transient, force-induced conformational change, representing an opportunity for detection and targeting of early molecular signatures of cell contractile forces in tissue repair and disease.

The extracellular matrix (ECM) forms the complex niche of structural elements surrounding cells in vivo. Cells interact with and are instructed by the ECM via cellular structures known as focal adhesions, large protein complexes composed of transmembrane receptors (integrins) and intracellular adaptor proteins that mechanically couple the cell's cytoskeleton to fibrillar ECM proteins such as fibronectin (Fn). Protein-protein interactions within focal adhesions are dynamic; mechanical forces play important roles for focal adhesion maturation and development, as well as for force-sensitive cell signaling via mechanosensory proteins. Recent work has shown that conformations of both intracellular focal adhesion constituents (e.g., vinculin, integrins; see Zhu et al., 2008; Grashoff et al., 2010; Carisey et al., 2013) as well as extracellular components (e.g., Fn; see Smith et al., 2007; Lemmon et al., 2011; Cao et al., 2012) are altered by forces transmitted to and from the ECM. In the latter case, previous work demonstrated that Fn within the ECM exhibits distinct but undefined altered structural states in response to cellular forces both in vitro and in vivo (see Chandler et al., 2011; Cao et al., 2012).

Fn comprises three types of tandem repeating units, each containing two antiparallel β-sheets. Type I and II repeats are structurally stabilized by disulfide bonds, whereas type III repeats are stabilized only by hydrogen bonding and Van der Waals forces, making them sensitive to unfolding due to physiologically relevant forces (see Krammer et al., 1999; Craig et al., 200; Craig et al., 2004; Li et al., 2005; Gee et al., 2008). These findings, when coupled with the active role of Fn's $9^{th}$ and $10^{th}$ type III repeats (FnIII9-10) in mediating integrin-specific interactions, inspired the theory that mechanical forces could trigger a "switch" in the integrin-binding profile of Fn (Krammer et al., 1999). Fn-integrin interactions are known to drive critical cell behaviors and are mediated primarily through the canonical and promiscuous integrin binding sequence Arg-Gly-Asp (RGD) within the $10^{th}$ type III repeat (Ruoslahti & Pierschbacher, 1987). A subset of integrins, including integrin α5β1, is additionally dependent on the sequence motif PHSRN (SEQ ID NO: 7) within the neighboring 9th type III repeat (Aota et al., 1994; Mardon & Grant, 1994; Mould et al., 1997; Garcia et al., 2002). Integrin specificity to Fn can be modulated in vitro by altering the structural stability of the integrin binding domain (i.e. the 9th and 10th type III repeats) via directed mutation (van der Walle et al., 2002) resulting in the regulation of developmentally and pathologically relevant cell differentiation pathways (Martino et al., 2009; Brown et al., 2011), and, importantly, cellular responses to microenvironmental mechanics (e.g., stiffness; Markowski et al., 2012). Despite these findings, the integrin switch theory and its potential relevance to biological processes in vivo remained undefined prior to the presently disclosed subject matter.

Reports have suggested that the relative separation distance between the "synergy" PHSRN sequence (SEQ ID NO: 7) in the 9th Fn type III repeat and the RGD site in the 10th Fn type III repeat is critical for engagement and activation of integrin α5β1 (Martino et al., 2009) and α3β1 (Brown et al., 2015) with an optimal PHSRN (SEQ ID NO: 7)-RGD distance of 3.7 nm for high affinity integrin α5β1 engagement (Craig et al., 2008). Furthermore, recent findings demonstrated that Fn fiber extension decreases cell spreading and adhesion (Hubbard et al., 2016).

The development of conformation-specific antibodies by phage display is well established, as work by Lefkowitz and coworkers have used phage display to isolate a conformation specific Fab to activated β-arrestin-1 (Shukla et al., 2013). Yet, particular challenges of the experiments described herein were that (1) the conformational change of the integrin binding domain was due to the application of force; (2) the application of force to Fn fibers led to multiple conformational changes along the length of the 440 kDa protein; and (3) the conformational change was highly labile due to the ability of Fn type III repeats to refold in the absence of force. Here predicted structures from steered molecular dynamics simulations coupled with molecular engineering were utilized to produce a mimetic of the strained integrin binding domain in order to perform phage display to discover the H5 clone. It is likely that the two model Fn fragments differ not only in separation between RGD and PHSRN (SEQ ID NO: 7), but also in relative conformational stability. FnIII9*10 is stabilized by a Leu1408Pro mutation between FnIII9 and FnIII1018, whereas FnIII-4G-10 is separated by a 4-glycine linker between the two domains.

One exemplary application of the H5 scFv of the presently disclosed subject matter is to probe pathologic ECMs, specifically tumor stroma and fibrotic ECMs which contain highly contractile myofibroblasts. Recent reports suggest that αv integrins on myofibroblasts are implicated in fibrogenesis in a broad range of fibrotic diseases, and that pharmacological blockade of αv integrins ameliorates liver and lung fibrosis (Henderson et al., 2013). The presently disclosed subject matter provides data regarding H5 staining of bleomycin-treated lungs in the context of idiopathic pulmonary fibrosis (IPF), a fatal form of progressive lung fibrosis in humans. The lungs of IPF patients are mechanically and biochemically heterogeneous, with areas of soft, normal lung tissue and stiffer regions of mature fibrosis. The H5 scFv is used to delineate regions of high ECM strain that also present an enhanced αv integrin binding character due to the conformation of the integrin binding domain, perhaps indicative of ongoing fibrosis.

The ability of the H5 antibody to extract structural information from the ECM was also demonstrated in a model of retinal angiogenesis, the process by which new blood vessels form by from endothelial sprouting (Patan, 2004). In mouse tissue sections, regions of high H5:Fn ratio were found at the extensions of endothelial tip cells, suggesting that Fn is unfolded in these regions. Fn is known to be a mediator of retinal angiogenesis, wherein astrocytes deposit fibronectin prior to differentiation of angioblasts to endothelial cells (Jiang et al., 1994). The results set forth herein suggest that forces from endothelial tip cells unfold Fn, presenting an αvβ3 binding character within the provisional matrix that may influence the formation of new blood vessels.

Described herein in some embodiments is a conformation-sensitive single-chain antibody (clone H5) to the integrin binding FnIII9-10 domain of Fn and demonstrated its mechano-sensitive binding to Fn in multiple model systems in vitro and ex vivo. While not wishing to be bound by any particular theory of operation, these force-sensitive conformational changes observed in the integrin binding domain of Fn are seen as evidence of the long theorized Fn "integrin-switch" which likely regulate integrin-specific cell responses based on controlling the presentation and accessibility of Fn epitopes in vivo and in engineered contexts. It is also provided herein that H5 specifically detects a force-induced conformational change within a protein. As mechanics of tissues are becoming increasingly implicated in pathogenesis of fibrotic diseases, there is a nascent opportunity to explore targeting the mechanochemical character of ECM as a paradigm for tissue imaging and disease diagnosis.

DEFINITIONS

Certain abbreviations employed in the instant disclosure and/or claims are summarized in Table 1.

TABLE 1

Table of Abbreviations

| | |
|---|---|
| βA | beta alanine |
| ECM | extracellular matrix |
| Fn or FN | fibronectin |
| HFF | human foreskin fibroblast |
| $K_D$ | dissociation constant |
| PDMS | polydimethylsiloxane |
| RGD | Arg-Gly-Arg |
| RT | room temperature |
| sc | single chain |
| scFv | single chain variable fragment antibody |
| SPR | surface plasmon resonance |
| TMB | 3,3',5,5'-tetramethylbenzidine |

Headings are included herein for reference and to aid in locating certain sections. These headings are not intended to limit the scope of the concepts described therein under, and these concepts may have applicability in other sections throughout the entire specification.

In describing and claiming the presently disclosed subject matter, the following terminology will be used in accordance with the definitions set forth below.

The terminology used herein is for the purpose of describing particular embodiments only and is not intended to be limiting of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed subject matter and the claims.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In some embodiments, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about".

The terms "additional therapeutically active compound" or "additional therapeutic agent", as used in the context of the presently disclosed subject matter, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease, or disorder, including, but not limited to, pain and inflammation.

As used herein, the term "adjuvant" refers to a substance that elicits an enhanced immune response when used in combination with a specific antigen.

As use herein, the terms "administration of" and or "administering" a compound should be understood to mean providing a compound of the presently disclosed subject matter or a prodrug of a compound of the presently disclosed subject matter to a subject in need of treatment.

The term "adult" as used herein, is meant to refer to any non-embryonic or non-juvenile subject. For example, the term "adult adipose tissue stem cell", refers to an adipose stem cell, other than that obtained from an embryo or juvenile subject.

As used herein, an "agent" is meant to include something being contacted with a cell population to elicit an effect, such as a drug, a protein, a peptide. An "additional therapeutic agent" refers to a drug or other compound used to treat an illness and can include, for example, an antibiotic or a chemotherapeutic agent.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom", means reducing the severity of the symptom or the frequency with which such a symptom is experienced by a patient, or both.

As used herein, an "analog" of a chemical compound is a compound that, by way of example, resembles another in structure but is not necessarily an isomer (e.g., 5-fluorouracil is an analog of thymine).

As used herein, amino acids are represented by the full name thereof, by the three letter code corresponding thereto, and/or by the one-letter code corresponding thereto, as summarized in Table 2:

TABLE 2

Amino Acids and Codes Therefor

| Full Name | 3-Letter Code | 1-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the presently disclosed subject matter, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the presently disclosed subject matter.

The term "amino acid" is used interchangeably with "amino acid residue", and may refer to a free amino acid and to an amino acid residue of a peptide. It will be apparent from the context in which the term is used whether it refers to a free amino acid or a residue of a peptide.

Amino acids have the following general structure:

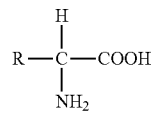

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the presently disclosed subject matter follows the conventional practice wherein the amino group is presented to the left and the carboxy group to the right of each amino acid residue. In the formulae representing selected specific embodiments of the presently disclosed subject matter, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antagomir" refers to a small RNA or DNA (or chimeric) molecule to antagonize endogenous small RNA regulators like microRNA (miRNA). These antagonists bear complementary nucleotide sequences for the most part, which means that antagomirs should hybridize to the mature microRNA (miRNA). They prevent other molecules from binding to a desired site on an mRNA molecule and are used to silence endogenous microRNA (miR). Antagomirs are therefore designed to block biological activity of these post-transcriptional molecular switches. Like the preferred target ligands (microRNA, miRNA), antagomirs have to cross membranes to enter a cell. Antagomirs also known as anti-miRs or blockmirs.

MicroRNAs are generally about 16-25 nucleotides in length. In some embodiments, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "antibody", as used herein, refers to an immunoglobulin molecule which is able to specifically or selectively bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the presently disclosed subject matter may exist in a variety of forms. The term "antibody" refers to polyclonal and monoclonal antibodies and derivatives thereof (including chimeric, synthesized, humanized and human antibodies), including an entire immunoglobulin or antibody or any functional fragment of an immunoglobulin molecule which binds to the target antigen and or combinations thereof. Examples of such functional entities include complete antibody molecules, antibody fragments, such as $F_v$, single chain $F_v$, complementarity determining regions (CDRs), $V_L$ (light chain variable region), $V_H$ (heavy chain variable region), Fab, $F(ab')_2$ and any combination of those or any other functional portion of an immunoglobulin peptide capable of binding to target antigen.

Antibodies exist, e.g., as intact immunoglobulins or as a number of well characterized fragments produced by digestion with various peptidases. Thus, for example, pepsin digests an antibody below the disulfide linkages in the hinge region to produce $F(ab')_2$ a dimer of Fab which itself is a light chain joined to $V_H$-$C_{H1}$ by a disulfide bond. The $F(ab')_2$ may be reduced under mild conditions to break the disulfide linkage in the hinge region, thereby converting the $F(ab')_2$ dimer into an $Fab_1$ monomer. The $Fab_1$ monomer is essentially an Fab with part of the hinge region (see Paul, 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

An "antibody heavy chain", as used herein, refers to the larger of the two types of polypeptide chains present in all antibody molecules.

An "antibody light chain", as used herein, refers to the smaller of the two types of polypeptide chains present in all antibody molecules.

The term "single chain antibody" refers to an antibody wherein the genetic information encoding the functional fragments of the antibody are located in a single contiguous length of DNA. For a thorough description of single chain antibodies, see Bird et al., 1988; Huston et al., 1988.

The term "humanized" refers to an antibody wherein the constant regions have at least about 80% or greater homology to human immunoglobulin. Additionally, some of the nonhuman, such as murine, variable region amino acid residues can be modified to contain amino acid residues of human origin. Humanized antibodies have been referred to as "reshaped" antibodies. Manipulation of the complementarity-determining regions (CDR) is a way of achieving humanized antibodies. See for example, Jones et al., 1986; Riechmann et al., 1988, both of which are incorporated by reference herein. For a review article concerning humanized antibodies, see Winter & Milstein, 1991, incorporated by reference herein. See also U.S. Pat. Nos. 4,816,567; 5,482,856; 6,479,284; 6,677,436; 7,060,808; 7,906,625; 8,398,980; 8,436,150; 8,796,439; and 10,253,111; and U.S. Patent Application Publication Nos. 2003/0017534, 2018/0298087, 2018/0312588, 2018/0346564, and 2019/0151448, each of which is incorporated by reference in its entirety.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antimicrobial agents" as used herein refers to any naturally-occurring, synthetic, or semi-synthetic compound or composition or mixture thereof, which is safe for human or animal use as practiced in the methods of this presently disclosed subject matter, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the presently disclosed subject matter include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "autologous", as used herein, refers to something that occurs naturally and normally in a certain type of tissue or in a specific structure of the body.

In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "blastema", as used herein, encompasses inter alia, the primordial cellular mass from which an organ, tissue or part is formed as well as a cluster of cells competent to initiate and/or facilitate the regeneration of a damaged or ablated structure.

The term "biocompatible", as used herein, refers to a material that does not elicit a substantial detrimental response in the host.

The term "biodegradable", as used herein, means capable of being biologically decomposed. A biodegradable material differs from a non-biodegradable material in that a biodegradable material can be biologically decomposed into units which may be either removed from the biological system and/or chemically incorporated into the biological system.

As used herein, the term "biologically active fragments" or "bioactive fragment" of the polypeptides encompasses natural or synthetic portions of the full-length protein that are capable of specific or selective binding to their natural ligand or of performing the function of the protein.

The term "biological sample", as used herein, refers to samples obtained from a subject, including, but not limited to, skin, hair, tissue, blood, plasma, cells, sweat and urine.

The term "bioresorbable", as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable", as the term is used herein, means that at least 80% of the total mass of material implanted is resorbed within one year.

The terms "cell" and "cell line", as used herein, may be used interchangeably. All of these terms also include their progeny, which are any and all subsequent generations. It is understood that all progeny may not be identical due to deliberate or inadvertent mutations.

The terms "cell culture" and "culture", as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture", "organ culture", "organ system culture" or "organotypic culture" may occasionally be used interchangeably with the term "cell culture".

The phrases "cell culture medium", "culture medium" (plural "media" in each case) and "medium formulation" refer to a nutritive solution for cultivating cells and may be used interchangeably.

The term "cell surface protein" means a protein found where at least part of the protein is exposed at the outer aspect of the cell membrane. Examples include growth factor receptors.

As used herein, the term "chemically conjugated", or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene comprises the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and in some embodiments at least about 75%, at least about 90%, or at least about 95% of the nucleotide residues of the first portion are capable of base pairing with nucleotide residues in the second portion. More in some embodiments, all nucleotide residues of the first portion are capable of base pairing with nucleotide residues in the second portion.

A "compound", as used herein, refers to any type of substance or agent that is commonly considered a drug, or a candidate for use as a drug, combinations, and mixtures of the above, as well as polypeptides and antibodies of the presently disclosed subject matter.

A "computer-readable medium" is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

As used herein, the term "conservative amino acid substitution" is defined herein as an amino acid exchange within one of the five groups summarized in Table 3.

TABLE 3

Conservative Amino Acid Substitutions

| Group | Characteristics | Amino Acids |
|---|---|---|
| A. | Small aliphatic, nonpolar or slightly polar residues | Ala, Ser, Thr, Pro, Gly |
| B. | Polar, negatively charged residues and their amides | Asp, Asn, Glu, Gln |
| C. | Polar, positively charged residues | His, Arg, Lys |
| D. | Large, aliphatic, nonpolar residues | Met Leu, Ile, Val, Cys |
| E. | Large, aromatic residues | Phe, Tyr, Trp |

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

"Cytokine", as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "delivery vehicle" refers to any kind of device or material which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and in some embodiments at least about 99%, by weight, of the protein or peptide in the preparation is the particular protein or peptide.

The term "feeder cells" as used herein refers to cells of one type that are co-cultured with cells of a second type, to provide an environment in which the cells of the second type can be maintained, and perhaps proliferate. The feeder cells can be from a different species than the cells they are supporting. Feeder cells can be non-lethally irradiated or treated to prevent their proliferation prior to being co-cultured to ensure to that they do not proliferate and mingle with the cells which they are feeding. The terms, "feeder cells", "feeders", and "feeder layers" are used interchangeably herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment", as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, in some embodiments, at least about 100 to about 200 nucleotides, in some embodiments, at least about 200 nucleotides to about 300 nucleotides, yet in some embodiments, at least about 300 to about 350, in some embodiments, at least about 350 nucleotides to about 500 nucleotides, yet in some embodiments, at least about 500 to about 600, in some embodiments, at least about 600 nucleotides to about 620 nucleotides, yet in some embodiments, at least about 620 to about 650, and most in some embodiments, the nucleic acid fragment will be greater than about 650 nucleotides in length. In the case of a shorter sequence such as SEQ ID NO: 1, fragments are shorter.

As used herein, a "functional" biological molecule is a biological molecule in a form in which it exhibits a property by which it is characterized. A functional enzyme, for example, is one which exhibits the characteristic catalytic activity by which the enzyme is characterized.

"Graft" refers to any free (unattached) cell, tissue, or organ for transplantation.

"Allograft" or "allogeneic" refers to a transplanted cell, tissue, or organ derived from a different animal of the same species.

"Xenograft" or "xenogeneic" refers to a transplanted cell, tissue, or organ derived from an animal of a different species.

The term "growth factor" as used herein means a bioactive molecule that promotes the proliferation of a cell or tissue. Growth factors useful in the presently disclosed subject matter include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue. Note that many factors are pleiotropic in their activity and the activity can vary depending on things such as the cell type being contacted, the state of proliferation or differentiation of the cell, etc.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin & Altschul, 1990, modified as in Karlin & Altschul, 1993). This algorithm is incorporated into the NBLAST and XBLAST programs of Altschul et al., 1990, and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al., 1997. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

The term "ingredient" refers to any compound, whether of chemical or biological origin, that can be used in cell culture media to maintain or promote the proliferation, survival, or differentiation of cells. The terms "component", "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit", as used herein, means to suppress or block an activity or function such that it is lower relative to a control value. The inhibition can be via direct or indirect mechanisms. In some embodiments, the activity is suppressed or blocked by at least 10% compared to a control value, more in some embodiments by at least 25%, and in some embodiments by at least 50%.

The term "inhibitor" as used herein, refers to any compound or agent, the application of which results in the inhibition of a process or function of interest, including, but not limited to, expression, levels, and activity. Inhibition can be inferred if there is a reduction in the activity or function of interest.

The term "inhibit a complex", as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound or cells of the presently disclosed subject matter by any number of routes and means including, but not limited to, intravitreal, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

The term "injury" refers to any physical damage to the body caused by violence, accident, trauma, or fracture, etc., as well as damage by surgery.

As used herein, an "instructional material" includes a publication, a recording, a diagram, or any other medium of expression which can be used to communicate the usefulness of the peptide of the presently disclosed subject matter in the kit for effecting alleviation of the various diseases or disorders recited herein. Optionally, or alternately, the instructional material may describe one or more methods of alleviating the diseases or disorders in a cell or a tissue of a mammal. The instructional material of the kit of the presently disclosed subject matter may, for example, be affixed to a container which contains the identified compound presently disclosed subject matter or be shipped together with a container which contains the identified compound. Alternatively, the instructional material may be shipped separately from the container with the intention that the instructional material and the compound be used cooperatively by the recipient.

Used interchangeably herein are the terms: 1) "isolate" and "select"; and 2) "detect" and "identify".

The term "isolated", when used in reference to compositions and cells, refers to a particular composition or cell of interest, or population of cells of interest, at least partially isolated from other cell types or other cellular material with which it naturally occurs in the tissue of origin. A composition or cell sample is "substantially pure" when it is at least 60%, or at least 75%, or at least 90%, and, in certain cases, at least 99% free of materials, compositions, cells other than composition or cells of interest. Purity can be measured by any appropriate method, for example, by fluorescence-activated cell sorting (FACS), or other assays which distinguish cell types. Representative isolation techniques are disclosed herein for antibodies and fragments thereof.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "ligand" is a compound that specifically or selectively binds to a target compound. A ligand (e.g., an antibody) "specifically binds to", "is specifically immunoreactive with", "having a selective binding activity", "selectively binds to" or "is selectively immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically or selectively binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow & Lane, 1988, for a description of immunoassay formats and conditions that can be used to determine specific immunoreactivity.

A "receptor" is a compound that specifically or selectively binds to a ligand.

A ligand or a receptor (e.g., an antibody) "specifically binds to", "is specifically immunoreactive with", "having a selective binding activity", "selectively binds to" or "is selectively immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically or selectively binds under hybridization conditions to a compound polynucleotide comprising a complementary sequence; an antibody specifically or selectively binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow & Lane 1988 for a description of immunoassay formats and conditions that can be used to determine specific or selective immunoreactivity. See also the EXAMPLES set forth herein below for additional formats and conditions that can be used to determine specific or selective immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

Micro-RNAs are generally about 16-25 nucleotides in length. In some embodiments, miRNAs are RNA molecules of 22 nucleotides or less in length. These molecules have been found to be highly involved in the pathology of several types of cancer. Although the miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules. miRNAs are species of small non-coding single-stranded regulatory RNAs that interact with the 3'-untranslated region (3'-UTR) of target mRNA molecules through partial sequence homology. They participate in regulatory networks as controlling elements that direct comprehensive gene expression. Bioinformatics analysis has predicted that a single miRNA can regulate hundreds of target genes, contributing to the combinational and subtle regulation of numerous genetic pathways.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil).

As used herein, the term "nucleic acid" encompasses RNA as well as single and double-stranded DNA and cDNA. Furthermore, the terms, "nucleic acid", "DNA", "RNA" and similar terms also include nucleic acid analogs, i.e. analogs having other than a phosphodiester backbone. For example, the so-called "peptide nucleic acids", which are known in the art and have peptide bonds instead of phosphodiester bonds in the backbone, are considered within the scope of the presently disclosed subject matter. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

The term "nucleic acid construct", as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

The term "peptide" typically refers to short polypeptides.

The term "per application" as used herein refers to administration of cells, a drug, or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent", as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

The term "propagate" means to reproduce or to generate.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross & Mienhofer, 1981 for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. Representative purification techniques are disclosed herein for antibodies and fragments thereof.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell". A gene which is expressed in a recombinant host cell wherein the gene comprises a recombinant polynucleotide, produces a "recombinant polypeptide".

A "recombinant polypeptide" is one which is produced upon expression of a recombinant polynucleotide.

The term "regulate" refers to either stimulating or inhibiting a function or activity of interest.

As used herein, term "regulatory elements" is used interchangeably with "regulatory sequences" and refers to promoters, enhancers, and other expression control elements, or any combination of such elements.

A "reversibly implantable" device is one which may be inserted (e.g., surgically or by insertion into a natural orifice of the animal) into the body of an animal and thereafter removed without great harm to the health of the animal.

A "sample", as used herein, refers in some embodiments to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

As used herein, the term "single chain variable fragment" (scFv) refers to a single chain antibody fragment comprised of a heavy and light chain linked by a peptide linker. In some cases scFv are expressed on the surface of an engineered cell, for the purpose of selecting particular scFv that bind to an antigen of interest.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In some embodiments, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" when used in reference to a substrate forming a linkage with a compound, relates to a solvent insoluble substrate that is capable of forming linkages (in some embodiments covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "solid support suitable for maintaining cells in a tissue culture environment" is meant any surface such as a tissue culture dish or plate, or even a cover, where medium containing cells can be added, and that support can be placed into a suitable environment such as a tissue culture incubator for maintaining or growing the cells. This should of course be a solid support that is either sterile or capable of being sterilized. The support does not need to be one suitable for cell attachment.

The term "solid support is a low adherence, ultralow adherence, or non-adherence support for cell culture purposes" refers to a vehicle such as a bacteriological plate or a tissue culture dish or plate which has not been treated or prepared to enhance the ability of mammalian cells to adhere to the surface. It could include, for example, a dish where a layer of agar has been added to prevent cells from attaching. It is known to those of ordinary skill in the art that bacteriological plates are not treated to enhance attachment of mammalian cells because bacteriological plates are generally used with agar, where bacteria are suspended in the agar and grow in the agar.

The term "standard", as used herein, refers to something used for comparison. For example, a standard can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In some embodiments, the activity or function is stimulated by at least 10% compared to a control value, more in some embodiments by at least 25%, and in some embodiments by at least 50%.

The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of diagnosis or treatment is an animal, including a human. It also includes pets and livestock.

As used herein, a "subject in need thereof" is a patient, animal, mammal, or human, who will benefit from the method of this presently disclosed subject matter.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "substantially homologous amino acid sequences" includes those amino acid sequences which have at least about 95% homology, in some embodiments at least about 96% homology, more in some embodiments at least about 97% homology, in some embodiments at least about 98% homology, and most in some embodiments at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the presently disclosed subject matter.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In some embodiments, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; in some embodiments in 7% (SDS), 0.5 M NaPO4, 1 mM EDTA at 50° C. with washing in 1×SSC, 0.1% SDS at 50° C.; in some embodiments 7% SDS, 0.5 M NaPO4, 1 mM EDTA at 50° C. with washing in 0.5×SSC, 0.1% SDS at 50° C.; and more in some embodiments in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984), and the BLASTN or FASTA programs (Altschul et al., 1990a; Altschul et al., 1990b; Altschul et al., 1997). The default settings provided with these programs are suitable for determining substantial similarity of nucleic acid sequences for purposes of the presently disclosed subject matter.

The term "substantially pure" describes a compound, e.g., a protein or polypeptide which has been separated from components which naturally accompany it. Typically, a compound is substantially pure when at least 10%, more in some embodiments at least 20%, more in some embodiments at least 50%, more in some embodiments at least 60%, more in some embodiments at least 75%, more in some embodiments at least 90%, and most in some embodiments at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "substituent" as used in the phrase "other cells which are not substituents of the at least one self-organizing blastema" refers to substituent cells of the blastema. Therefore, a cell which is not a substituent of a self-organizing blastema can be a cell that is adjacent to the blastema and need not be a cell derived from a self-organizing blastema.

A "surface active agent" or "surfactant" is a substance that has the ability to reduce the surface tension of materials and enable penetration into and through materials.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The use of the phrase "tissue culture dish or plate" refers to any type of vessel which can be used to plate cells for growth or differentiation.

The term "thermal injury" is used interchangeably with "thermal burn" herein.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "topical application", as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous".

The term "transfection" is used interchangeably with the terms "gene transfer", "transformation", and "transduction", and means the intracellular introduction of a polynucleotide.

"Transfection efficiency" refers to the relative amount of the transgene taken up by the cells subjected to transfection. In practice, transfection efficiency is estimated by the amount of the reporter gene product expressed following the transfection procedure.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat", as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear, break, or rupture to a tissue or cell layer. A wound may occur by any physical insult, including a surgical procedure or as a result of a disease, disorder condition.

Methods useful for the practice of the presently disclosed subject matter which are not described herein are also known in the art. Useful methods include those described in PCT International Patent Application Publication Nos. WO 2007/019107; WO 2007/030652; WO 2007/089798; WO 2008/060374, the methods of which are hereby incorporated by reference.

EXEMPLARY EMBODIMENTS

The presently disclosed subject matter provides compositions and methods useful for targeting of a mechanically exposed cryptic site within fibronectin's integrin binding domain. Thus, in some embodiments, the presently disclosed subject matter provides methods for targeting conformational states of fibronectin (FN) in samples, optionally biological samples isolated from or present within a subject. In some embodiments, the methods comprise contacting a sample with a composition having a selective binding activity for a conformational state of FN comprising FnIII9-4G-10 (4G), whereby the conformational state is targeted. In some embodiments, the sample comprises or is suspected to comprise a tissue undergoing tissue repair, a tissue that is diseased, a tissue that suffers from a disorder, or any combination thereof.

The presently disclosed subject matter provides for the detection of an integrin-binding mechanoswitch within fibronectin (Fn) during tissue formation and fibrosis. The disclosed results demonstrate the in vivo existence and activation of the long theorized Fn conformational switch within the integrin binding domain and suggest its influence in skewing integrin specificity in both developmental processes, as well as in pathological tissue fibrosis. Antibodies such as the presently disclosed H5 thus represent an attractive approach to detecting and targeting key developmental and disease processes.

Binding kinetics and activity of H5 are disclosed herein. H5 recognizes FnIII9, also referred to herein as FnIII9-4G-10 (4G), and it selectively inhibits $\alpha v\beta 3$ binding to Fn-absorbed surfaces.

The presently disclosed subject matter provides compositions and methods useful for detecting distinct conformational states of Fn. In some embodiments, H5 binding to Fn can detect distinct conformational states of Fn, such as FnIII9-4G-10 (4G).

The presently disclosed subject matter provides in some embodiments compositions and methods useful for detecting distinct conformational states of Fn and the binding ratios are useful for distinguishing normal tissue from tissue that is diseased or suffers from a disorder. In some embodiments, the severity of fibrosis in a tissue can be determined. In some embodiments, the presently disclosed subject matter is useful for detecting transient, force-induced conformational change in Fn. The compositions and methods are useful for targeting early molecular signatures of cell contractile forces during tissue repair. The compositions and methods are useful for targeting early molecular signatures of cell contractile forces in diseases and disorders.

In some embodiments, the presently disclosed subject matter provides compositions and methods useful for detecting and comparing pathologic ECMs. In some embodiments, the presently disclosed subject matter provides compositions and methods useful for detecting and distinguishing tumor stroma and fibrotic ECMs.

In some embodiments, the presently disclosed subject matter provides compositions and methods useful for delineating regions of high ECM strain. In some embodiments, the high ECM strain is associated with enhanced $\alpha v$ integrin binding character due to the conformation of the integrin binding domain, perhaps indicative of ongoing fibrosis.

In some embodiments, an antibody of the presently disclosed subject matter is useful for extracting structural information from the ECM.

In some embodiments, the compositions and methods are useful for determining antibody:Fn ratios, which in turn can be used for diagnosing or distinguishing normal from diseased tissue and for determining the type of treatment to be administered when the subject has been diagnosed with a disease or disorder.

The presently disclosed subject matter provides other antibodies and biologically active fragments and homologs thereof as well as methods for preparing and testing new antibodies for the properties disclosed herein.

In some embodiments, the fragments are fragments of scFv. In some embodiments, the scFv fragments are mammalian. In some embodiments, the scFv fragments are humanized.

In some embodiments, an antibody or biologically active fragment or homolog thereof is useful for treating a disease or disorder associated with the fibronectin-interaction signaling pathway disclosed herein. In some embodiments, the pathway is regulated by a mechanoswitch.

In some embodiments, the presently disclosed subject matter uses a biologically active antibody or biologically active fragment or homolog thereof. In some embodiments, the isolated polypeptide comprises a mammalian molecule at least about 30% homologous to a polypeptide having the amino acid sequence of at least one of the sequences disclosed herein. In some embodiments, the isolated polypeptide is at least about 35% homologous, more in some embodiments, about 40% homologous, more in some embodiments, about 45% homologous, in some embodiments, about 50% homologous, more in some embodiments, about 55% homologous, in some embodiments, about 60% homologous, more in some embodiments, about 65% homologous, more in some embodiments, about 70% homologous, more in some embodiments, about 75% homologous, in some embodiments, about 80% homologous, more in some embodiments, about 85% homologous, more in some embodiments, about 90% homologous, in some embodiments, about 95% homologous, more in some embodiments, about 96% homologous, more in some embodiments, about 97% homologous, more in some embodiments, about 98% homologous, and most in some embodiments, about 99% homologous to at least one of the peptide sequences disclosed herein.

The presently disclosed subject matter further encompasses modification of the antibodies and fragments thereof disclosed herein, including amino acid deletions, additions, and substitutions, particularly conservative substitutions. The presently disclosed subject matter also encompasses modifications to increase in vivo half-life and decrease degradation in vivo. Substitutions, additions, and deletions can include, for example, 1, 2, 3, 4, 5, 6, 7, 8, 9, 10, 11, 12, 13, 14, 15, 16, 17, 18, 19, 20, 21, 22, 23, 24, and 25 changes as long as the activity disclosed herein remains substantially the same.

The presently disclosed subject matter includes an isolated nucleic acid comprising a nucleic acid sequence encoding an antibody of the presently disclosed subject matter, or a fragment or homolog thereof. In some embodiments, the nucleic acid sequence encodes a peptide comprising an antibody sequence of the presently disclosed subject matter, or a biologically active fragment of homolog thereof.

In some embodiments, a homolog of a peptide (antibody or fragment) of the presently disclosed subject matter is one with one or more amino acid substitutions, deletions, or additions, and with the sequence identities described herein. In some embodiments, the substitution, deletion, or addition is conservative. In some embodiments, a serine or an alanine is substituted for a cysteine residue in a peptide of the presently disclosed subject matter.

In some embodiments, the subject is a mammal. In some embodiments, the mammal is a human.

The presently disclosed subject matter encompasses the use of purified isolated, recombinant, and synthetic peptides.

The presently disclosed subject matter further encompasses the use of drugs or other molecules that can target the exposed cryptic site disclosed herein and can, for example, recognize the conformational changes disclosed herein and have the same activity disclosed herein.

Thus, the presently disclosed subject matter provides in some embodiments methods for detecting conformational states of fibronectin (FN) in samples. In some embodiments, the methods comprise contacting a sample with a composition having a selective binding activity for a conformational state of FN comprising FnIII9-4G-10 (4G); and detecting the binding of the composition, whereby the conformational state of FN is detected. In some embodiments, the sample comprises or is suspected to comprise a tissue undergoing tissue repair, a tissue that is diseased, a tissue that suffers from a disorder, or a combination thereof. In some embodiments, the sample comprises or is suspected to comprise a pathologic extracellular matrix (ECM). In some embodiments, the sample comprises or is suspected to comprise tumor stroma, a fibrotic ECM, or a combination thereof. Reference is made to the Examples as set forth herein below for exemplary approaches for sample assessment. In some embodiments, detecting the binding of the composition comprises detecting a binding ratio of composition to FN. See FIGS. 5A-5C and 6A-6D for exemplary ratio evaluations.

In some embodiments, detecting the binding of the composition comprises distinguishing normal from diseased tissue. In some embodiments, detecting the binding of the composition comprises determining severity of fibrosis in the sample, such as by using a binding ratio of composition to FN. Reference is made to the Examples as set forth herein below for exemplary approaches for sample assessment. In some embodiments, detecting the binding of the composition comprises detecting a transient, force-induced conformational change in FN. In some embodiments, detecting the binding of the composition comprises extracting structural information for an ECM in the sample. In some embodiments, extracting structural information for an ECM in the sample comprises delineating regions of high ECM strain. In some embodiments, the high ECM strain is associated with enhanced αv integrin binding character. Here as well, reference is made to the Examples as set forth herein below for exemplary approaches for sample assessment.

In some embodiments, the methods further comprise determining a type of treatment to be administered to the subject based on the detecting of the binding of the composition.

The presently disclosed subject matter also provides in some embodiments methods for treating diseases and/or disorders in subjects. In some embodiments, the methods comprise administering to a subject in need there of a therapeutically effective amount of a composition having a selective binding activity for a conformational state of FN comprising FnIII9-4G-10 (4G), whereby treatment is accomplished. In some embodiments, the disease and/or disorder has a characteristic selected from the group consisting of a tissue undergoing tissue repair, a tissue that is diseased, a tissue that suffers from a disorder, and any combination thereof. In some embodiments, the characteristic is a pathologic extracellular matrix (ECM). In some embodiments, the characteristic is tumor stroma, a fibrotic ECM, or a combination thereof. Here as well, reference is made to the Examples as set forth herein below for exemplary diseases and disorders.

In some embodiments of the presently disclosed methods, the composition having a selective binding activity for a conformational state of FN comprising FnIII9-4G-10 (4G) is an isolated and purified antibody comprising an amino acid sequence selected from the group consisting of SEQ ID NOs: 2, 4, and 6-12, a fragment thereof, or an antibody have a sequence approximately 95% identical to a sequence of SEQ ID NOs: 2, 4, and 6-12, or a fragment thereof. In some embodiments, the amino acid sequence comprises at least one modification selected from the group consisting of an amino acid deletion, an amino acid addition, an amino acid substitution, and combinations thereof. In some embodiments, the antibody or fragment thereof comprises a scFv fragment. In some embodiments, the scFv fragment is mammalian. In some embodiments, the scFv fragment is humanized.

The presently disclosed subject matter also provides in some embodiments methods for screening for compounds having selective binding activities for conformational states of FN comprising FnIII9-4G-10 (4G). In some embodiments, the methods comprise providing a sample comprising a conformational state of FN comprising FnIII9-4G-10 (4G); contacting the sample with a candidate compound; and detecting binding of the candidate compound to the sample. In some embodiments, the candidate compound is a member of a library of compounds. In some embodiments, the candidate compound is a small molecule or an antibody. In some embodiments, the conformational state of FN is a force-induced conformational change in Fn. Reference is made to the Examples as set forth herein below for exemplary approaches for binding assessment.

The presently disclosed subject matter also provides in some embodiments compounds identified by the presently disclosed methods.

The presently disclosed subject matter also provides in some embodiments methods for treating diseases and/or disorder in subjects comprising administering to a subject in need thereof a therapeutically effective amount of a composition comprising the scFv peptide in accordance with the presently disclosed subject matter, whereby treatment is accomplished. Here as well, reference is made to the Examples as set forth herein below for exemplary diseases and disorders.

The presently disclosed subject matter also provides in some embodiments methods for ameliorating at least one symptom of consequence of a disease or disorder associated with abnormal expression of a force-induced conformational state of FN comprising FnIII9-4G-10 (4G) in a subject. In some embodiments, the methods comprise administering to a subject in need thereof a therapeutically effective amount of a composition comprising the scFv peptide in accordance with the presently disclosed subject matter, wherein at least one symptom of consequence of a disease or disorder associated with abnormal expression of a force-induced conformational state of FN comprising FnIII9-4G-10 (4G) is ameliorated. Here as well, reference is made to the Examples as set forth herein below for exemplary diseases and disorders.

In some embodiments of the therapeutic methods, the disease or disorder is associated with a tissue undergoing tissue repair, a tissue that is diseased, a tissue that suffers from a disorder, or any combination thereof. In some embodiments, the disease or disorder is associated with a pathologic extracellular matrix (ECM). In some embodiments, the disease or disorder is associated with tumor stroma, a fibrotic ECM, or a combination thereof. Here as well, reference is made to the Examples as set forth herein below for exemplary diseases and disorders.

Exemplary Sequences of the Presently Disclosed Subject Matter

The presently disclosed subject matter provides for the use of various antibodies with the activity described herein as well as biologically active fragments and homologs thereof.

In some embodiments, the presently disclosed subject matter provides isolated and purified antibodies that comprise an amino acid sequence selected from the group consisting of SEQ ID NOs: 2, 4, and 6-12, a fragment thereof, an antibody having an amino acid sequence that is approximately 95% identical to the sequence of any one of SEQ ID NOs: 2, 4, and 6-12, a fragment thereof, and and substantially homologous amino acid sequences of any of the foregoing sequences. In some embodiments, the amino acid sequence comprises at least one modification selected from the group consisting of an amino acid deletion, an amino acid addition, an amino acid substitution, and combinations thereof. In some embodiments, the antibody or fragment thereof comprises an scFv fragment. In some embodiments, the scFv fragment is mammalian. In some embodiments, the scFv fragment is humanized.

In some embodiments, the isolated and purified antibody, or fragment or homolog thereof, comprises a heavy chain CDR1 of sequence SYAMS (SEQ ID NO: 24), a heavy chain CDR2 of sequence DIYDGGGTNYADSVKG (SEQ ID NO: 25), a heavy chain CDR3 of sequence TADNFY (SEQ ID NO: 26) or TADNFD (SEQ ID NO: 27), a light chain CDR1 of sequence RASQSISSYLN (SEQ ID NO: 28), a light chain CDR2 of sequence AASTLQS (SEQ ID NO: 29), and a light chain CDR3 of sequence QQANSAPTT (SEQ ID NO: 30).

In some embodiments, the isolated and purified antibody, or fragment or homolog thereof, comprises a modification at its N-terminus, its C-terminus, or both. In some embodiments, the modification comprises addition of a peptide tag, a SARAH domain, or a combination thereof. In some embodiments, the tag comprises a his tag, a myc tag, a VSV tag, an HA tag, a SortaseA tag, a PelB sequence, or any combination of one or more thereof.

The presently disclosed subject matter also provides in some embodiments isolated and purified nucleic acid sequences encoding the antibodies and fragments disclosed herein, and substantially homologous nucleic acid sequences thereto.

The presently disclosed subject matter also provides in some embodiments single chain variable fragment (scFv) peptides and substantially homologous amino acid sequences thereto. In some embodiments, the scFv peptides comprise a $V_H$ segment comprising a first amino acid sequence selected from the group consisting of amino acids 4-113 of any one of SEQ ID NOs: 2 and 8-12, a $V_L$ segment comprising a second amino acid sequence selected from the group consisting of amino acids 113-237 of SEQ ID NOs. 2 and 8-12, or a combination thereof. In some embodiments, the $V_H$ segment and $V_L$ segment are coupled together with a linker peptide, optionally a glycine-rich peptide, and further optionally a glycine-rich peptide comprising a concatemer of one, two, or three copies of SEQ ID NO: 17, a concatemer of one, two, or three copies of SEQ ID NO: 18, or a mixture of one, two, or three copies of SEQ ID NO: 17 and one, two, or three copies of SEQ ID NO: 18. In some embodiments, the scFv peptides further comprises at least two pairs of the $V_H$ segment and $V_L$ segment, wherein the at least two pairs are linked to form a multivalent scFv. In some embodiments, the scFv peptide is present in the pharmacologically acceptable carrier. In some embodiments, the scFv peptide is grafted into a human or humanized antibody.

The presently disclosed subject matter also provides in some embodiments recombinant nucleic acids and substantially homologous nucleic acid sequences thereto. In some embodiments, the recombinant nucleic acids comprise a first nucleic acid segment encoding a $V_H$ segment having a first amino acid sequence selected from the group consisting of amino acids 4-113 of any one of SEQ ID NOs: 2 and 8-12, a second nucleic acid segment encoding a $V_L$ segment having a second amino acid sequence selected from the group consisting of amino acids 113-227 of SEQ ID NOs. 2 and 8-12, or a combination thereof, wherein the first and second segments are optionally present in a same reading frame. In some embodiments, the recombinant nucleic acids further comprise a third nucleic acid segment encoding a linker peptide coupling together the first and second segments in frame. In some embodiments, the recombinant nucleic acids further comprise one or more additional nucleic acid segments that encode one or more subsequences of an intact antibody, such that the recombinant nucleic acid encodes a recombinant intact antibody.

The presently disclosed subject matter also provides in some embodiments single chain variable fragment (scFv) peptide comprising a heavy chain CDR1 of sequence SYAMS (SEQ ID NO: 24), a heavy chain CDR2 of sequence DIYDGGGTNYADSVKG (SEQ ID NO: 25), a heavy chain CDR3 of sequence TADNFY (SEQ ID NO: 26) or TADNFD (SEQ ID NO: 27), a light chain CDR1 of sequence RASQSISSYLN (SEQ ID NO: 28), a light chain CDR2 of sequence AASTLQS (SEQ ID NO: 29), and a light chain CDR3 of sequence QQANSAPTT (SEQ ID NO: 30). In some embodiments, the scFv comprises a $V_H$ segment and a $V_L$ segment coupled together with a linker peptide. In some embodiments, the linker peptide is a glycine-rich peptide. In some embodiments, the glycine-rich peptide comprises a concatemer of one, two, or three copies of SEQ ID NO: 17, a concatemer of one, two, or three copies of SEQ ID NO: 18, or a mixture of one, two, or three copies of SEQ ID NO: 17 and one, two, or three copies of SEQ ID NO: 18. In some embodiments, the scFv peptide further comprises at least two pairs of the $V_H$ segment and $V_L$ segment, wherein the at least two pairs are linked to form a multivalent scFv. In some embodiments, the In some embodiments, the scFv peptide is present in the pharmacologically acceptable carrier. In some embodiments, the scFv peptide is grafted into a human or humanized antibody. In some embodiments, the scFv peptide further comprises a modification at its N-terminus, its C-terminus, or both. In some embodiments, the the modification comprises addition of a peptide tag, a SARAH domain, or a combination thereof. In some embodiments, the tag comprises a his tag, a myc tag, a VSV tag, an HA tag, a SortaseA tag, a PelB sequence, or any combination of one or more thereof. In some embodiments, the tag comprises an amino acid sequence selected from the group consisting of SEQ ID NOs: 31-36. In some embodiment, the SARAH domain comprises a sequence selected from the group consisting of SEQ ID NOs: 19-23.

In some embodiments, the presently disclosed antibodies, fragments, and homologs thereof can comprise a tag sequence, linker sequence, spacer sequence and/or other additional sequence that can be used in to facilitate expression, stability, purification, isolation, or other desired feature or aspect. Multiple copies of such sequences can be employed. Such sequences can be added to the N-terminus, the C-terminus, or both of an antibody, fragment, or homolog thereof of the presently disclosed subject matter. Representative such sequences include SARAH sequences. SEQ ID NOs: 19-23 are the amino acid sequences of exemplary SARAH domains that can be added to the N-terminus, the C-terminus, or both an antibody, fragment, or homolog thereof of the presently disclosed subject matter. Representative such sequences also include tags sequences such as myc, VSV, His, HA, SortaseA, and PelB tags. By way of particular example and not limitation, SEQ ID NOs: 31-36 are the amino acid sequences of exemplary tags that can be added to the N-terminus, the C-terminus, or both of that can be added to the N-terminus, the C-terminus, or both an antibody, fragment, or homolog thereof of the presently disclosed subject matter. EQKLISEEDL (SEQ ID NO: 31) is an exemplary myc tag, YTDIEMNRLGK (SEQ ID NO: 32) is an exemplary VSV tag, HHHHHH (SEQ ID NO: 33) is an exemplary His tag, YPYDVPDYA (SEQ ID NO: 34) is an exemplary HA tag, LPTEGG (SEQ ID NO: 35) is an exemplary SortaseA tag, and MKYLLPTAAAGLLL-LAAQPAMA (SEQ ID NO: 36) is an exemplary PelB tag. A representative linker sequence is a GAA sequence, which is used in the phage display application to connect the scFv to the p3 coat protein. Another representative linker sequence is NSAAH (generally applicable linker; SEQ ID NO: 37). A representative spacer sequence can include any length sequence as would be apparent to one of ordinary skill in the art upon a review of the instant disclosure, include one amino acid, such as alanine (A).

In some embodiments, an antibody or fragment thereof in accordance with the presently disclosed subject matter is modified by a SARAH domain. Representative approaches for implementing SARAH domains are described in European Patent Application No. 17868682.0; PCT International Patent Application Publication No. WO 2018/088403; U.S. patent application Ser. No. 16/345,639; and in Arimori et al., 2017, each of are herein wherein incorporated by reference in their entireties. In some embodiments, an N-terminus of a SARAH domain is linked to a C-terminus of a heavy chain domain ($V_H$ region) and/or to a C-terminus of a light chain domain ($V_L$ region) of an antibody or fragment thereof in accordance with the presently disclosed subject matter. A SARAH domain is a domain (peptide) comprising a short helix (hl) on the N-terminal side and a long helix (h2) on the C-terminal side, which in some embodiments comprises usually 42 to 54, optionally 43 to 49, further optionally 47 to 49, and yet further optionally 49 amino acid residues and has properties of forming antiparallel coiled coils between h2 with another SARAH domain. It should be noted that hl can comprise 5 to 7 amino acid residues, and h2 can comprise 38 to 42 pieces of amino acid residues.

The SARAH domain used here may be any SARAH domain as would be suitable to one of ordinary skill in the art upon a review on the instant disclosure. By way of further example and not limitation, in a case where two SARAH domains form an antiparallel coiled coil between h2, the distance between both N-termini of two SARAH domains (two hl) is optionally about 35 A to 45 A, further optionally about 39 A to 41 A, and further optionally about 40 A. Particular examples of such SARAH domains include the SARAH domain of the human mammalian sterile 20-like kinase 1 polypeptide (hMST1; DYEFLKSWTVEDLQKRL-LALDPMMEQEIEEIRQKYQSKRQPILDAIEAK, SEQ ID NO: 19; corresponding to amino acids 432-480 of Accession No. NP_006273.1 of the GENBANK® biosequence database), the SARAH domain of the human mammalian sterile 20-like kinase 2 polypeptide (hMST2; DFD-FLKNLSLEELQMRLKALDPMMEREIEEL RQRYTAKRQPILDAMDAK, SEQ ID NO: 20; corresponding to amino acids 325-373 of Accession No. NP_001243242.1 of the GENBANK® biosequence database), the SARAH domain of the human ras association domain-containing protein 5 isoform C polypeptide (hRAF5; GEVEWDAFSIPELQNFLTILEKEEQD-KIQQVQKKYDKFRQKLEE ALRES, SEQ ID NO: 21; corresponding to amino acids 212-260 of Accession No. NP_872606.1 of the GENBANK® biosequence database), the SARAH domain of the human ras association domain-containing protein 1 isoform B polypeptide (hRAF1; GEVNWDAFSMPELHN FLRILQREEEEHLRQILQKY-SYSRQKIQEALHAS, SEQ ID NO: 22; which shows 47/49 amino acid identity to amino acids 138-186 of Accession No. NP_001193886.1 of the GENBANK® biosequence database), the SARAH domain of the human protein salvador homolog 1 polypeptide (hSAV1; HILK-WELFQLADLDTYQGMLKLLFMKELE QIVKMYEAY-RQALLTELENR, SEQ ID NO: 23; corresponding to amino acids 320-368 of Accession No. NP_068590.1 of the GENBANK® biosequence database), and further include those having a sequence homology of in some embodiments 85% or more, in some embodiments 90% or more, and in some embodiments 95% or more with one of the foregoing SARAH domains. With respect to the foregoing representative SARAH domains, a general design approach can involve heavy and light chains of a given antibody being individually fused with a 49-residue SARAH domain via a two-residue (Gly-Ser) linker. In some embodiments with respect to the foregoing representative SARAH domains, two Cys residues (38 and 49) in the hRAF1 SARAH domain were substituted with Ser to avoid undesired disulfide bond formation. In some embodiments, residues 24 and 35 are mutated to Cys to form an asymmetric inter-chain disulfide bond based on the homodimeric hMST1 structure.

H5 DNA sequence (filtered DNA sequence consisting of 798 bases; SEQ ID NO: 1)

```
GAGGTGCAGCTGTTGGAGTCTGGGGGAGGCTTGGTACAGCCTGGGGGGT

CCCTGAGACTCTCCTGTGCAGCCTCTGGATTCACCTTTAGCAGCTATGC

CATGAGCTGGGTCCGCCAGGCTCCAGGGAAGGGGCTGGAGTGGGTCTCA

GATATTTATGATGGTGGTGGTACAAATTACGCAGACTCCGTGAAGGGCC

GGTTCACCACCTCCAGAGACAATTCCAAGAACACGCTGTATCTGCAAAT

GAACAGCCTGAGAGCCGAGGACACGGCCGTATATTACTGTGCGAAAACT

GCTGATAATTTTGACTACTGGGGCCAGGGAACCCTGGTCACCGTCTCGA

GCGGTGGAGGCGGTTCAGGCGGAGGTGGCAGCGGCGGTGGCGGGTCGAC

GGACATCCAGATGACCCAGTCTCCATCCTCCCTGTCTGCATCTGTAGGA

GACAGAGTCACCATCACTTGCCGGGCAAGTCAGAGCATTAGCAGCTATT

TAAATTGGTATCAGCAGAAACCAGGGAAAGCCCCTAAGCTCCTGATCTA

TGCTGCATCCACTTTGCAAAGTGGGGTCCCATCAAGGTTCAGTGGCAGT
```

-continued

GGATCTGGGACAGATTTCACTCTCACCATCAGCAGTCTGCAACCTGAAG

ATTTTGCAACTTACTACTGTCAACAGGCTAATAGTGCTCCTACTACGTT

CGGCCAAGGGACCAAGGTGGAAATCAAACGGGCGGCCGCA

H5 amino acid sequence (265 residues; SEQ ID NO: 2; encoded by SEQ ID NO: 1)

EVQLLESGGGLVQPGGSLRLSCAASGFTFSSYAMSWVRQAPGKGLEWVS

DIYDGGGTNYADSVKGRFTTSRDNSKNTLYLQMNSLRAEDTAVYYCAKT

ADNFDYWGQGTLVTVSSGGGGSGGGGSGGGGSTDIQMTQSPSSLSASVG

DRVTITCRASQSISSYLNWYQQKPGKAPKLLIYAASTLQSGVPSRFSGS

GSGTDFTLTISSLQPEDFATYYCQQANSAPTTFGQGTKVEIKRAAA

PelB+H5 DNA—DNA sequence consisting of 864 bases (the pelB sequence was added for expression in *E. coli;* 287 residues; SEQ ID NO: 3)

ATGAAATACCTATTGCCTACGGCAGCCGCTGGATTGTTATTACTCGCGG

CCCAGCCGGCCATGGCCGAGGTGCAGCTGTTGGAGTCTGGGGGAGGCTT

GGTACAGCCTGGGGGGTCCCTGAGACTCTCCTGTGCAGCCTCTGGATTC

ACCTTTAGCAGCTATGCCATGAGCTGGGTCCGCCAGGCTCCAGGGAAGG

GGCTGGAGTGGGTCTCAGATATTTATGATGGTGGTGGTACAAATTACGC

AGACTCCGTGAAGGGCCGGTTCACCACCTCCAGAGACAATTCCAAGAAC

ACGCTGTATCTGCAAATGAACAGCCTGAGAGCCGAGGACACGGCCGTAT

ATTACTGTGCGAAAACTGCTGATAATTTTGACTACTGGGGCCAGGGAAC

CCTGGTCACCGTCTCGAGCGGTGGAGGCGGTTCAGGCGGAGGTGGCAGC

GGCGGTGGCGGGTCGACGGACATCCAGATGACCCAGTCTCCATCCTCCC

TGTCTGCATCTGTAGGAGACAGAGTCACCATCACTTGCCGGGCAAGTCA

GAGCATTAGCAGCTATTTAAATTGGTATCAGCAGAAACCAGGGAAAGCC

CCTAAGCTCCTGATCTATGCTGCATCCACTTTGCAAAGTGGGGTCCCAT

CAAGGTTCAGTGGCAGTGGATCTGGGACAGATTTCACTCTCACCATCAG

CAGTCTGCAACCTGAAGATTTTGCAACTTACTACTGTCAACAGGCTAAT

AGTGCTCCTACTACGTTCGGCCAAGGGACCAAGGTGGAAATCAAACGGG

CGGCCGCA

PelB+H5 amino acid sequence (SEQ ID NO: 4; encoded by SEQ ID NO: 3)

MKYLLPTAAAGLLLLAAQPAMAEVQLLESGGGLVQPGGSLRLSCAASGF

TFSSYAMSWVRQAPGKGLEWVSDIYDGGGTNYADSVKGRFTTSRDNSKN

TLYLQMNSLRAEDTAVYYCAKTADNFDYWGQGTLVTVSSGGGGSGGGGS

GGGGSTDIQMTQSPSSLSASVGDRVTITCRASQSISSYLNWYQQKPGKA

PKLLIYAASTLQSGVPSRFSGSGSGTDFTLTISSLQPEDFATYYCQQAN

SAPTTFGQGTKVEIKRAAA

A 286 residue sequence (PelB+H5 T93 Sequence; SEQ ID NO: 5)

MKYLLPTAAAGLLLLAAQPAMAEVQLLESGGGLVQPGGSLRLSCAASGF

TFSSYAMSWVRQAPGKGLEWVSDIYDGGGTNYADSVKGRFTTSRDNSKN

TLYLQMNSLRAEDTAVYYCAKTADNFDYWGQGTLVTVSSGGGGSGGGGS

GGGGSTDIQMTQSPSSLSASVGDRVTITCRASQSISSYLNWYQQKPGKA

PKLLIYAASTLQSGVPSRFSGSGSGTDFTLTISSLQPEDFATYYCQQAN

SAPTTFGQGTKVEIKRAAA

Another 286 residue sequence (PelB+H5 T93I Sequence; SEQ ID NO: 6)

MKYLLPTAAAGLLLLAAQPAMAEVQLLESGGGLVQPGGSLRLSCAASGF

TFSSYAMSWVRQAPGKGLEWVSDIYDGGGTNYADSVKGRFTTSRDNSKN

TLYLQMNSLRAEDIAVYYCAKTADNFDYWGQGTLVTVSSGGGGSGGGGS

GGGGSTDIQMTQSPSSLSASVGDRVTITCRASQSISSYLNWYQQKPGKA

PKLLIYAASTLQSGVPSRFSGSGSGTDFTLTISSLQPEDFATYYCQQAN

SAPTTFGQGTKVEIKRAAA

H5 Clones Consensus Sequence (SEQ ID NO: 8)

EVQLLESGGGLVQPGGSLRLSCAASGFTESSYAMSWVRQAXGKGLEWVS

DIYDGGGTNYADSVKGRFTTSRDXSKNTXYLQMNSLRAEDTAVYYCXKT

ADNFXYWGQGTLVTVSSGGGGSGGGGSGGGGSTDIQMTQSPSSLSASVG

DRVTITCRASQSISSYLNWYQQKPGKAPKLLIYAASTLQSGVPSRFSGS

GSGTDFTLTISSLQPEDFATYYCQQANSAPTTFGQGTKVEIKRAAA

H5 Modified Clone R1F8/R1H8 (SEQ ID NO: 9)

EVQLLESGGGLVQPGGSLRLSCAASGFTESSYAMSWVRQAPGKGLEWVS

DIYDGGGTNYADSVKGRFTTSRDNSKNTLYLQMNSLRAEDTAVYYCTKT

ADNFDYWGQGTLVTVSSGGGGSGGGGSGGGGSTDIQMTQSPSSLSASVG

DRVTITCRASQSISSYLNWYQQKPGKAPKLLIYAASTLQSGVPSRFSGS

GSGTDFTLTISSLQPEDFATYYCQQANSAPTTFGQGTKVEIKRAAA

H5 Modified Clone R4B8 (SEQ ID NO: 10)

EVQLLESGGGLVQPGGSLRLSCAASGFTFSSYAMSWVRQAPGKGLEWVS

DIYDGGGTNYADSVKGRFTTSRDNSKNTLYLQMNSLRAEDTAVYYCAKT

ADNFYYWGQGTLVTVSSGGGGSGGGGSGGGGSTDIQMTQSPSSLSASVG

DRVTITCRASQSISSYLNWYQQKPGKAPKLLIYAASTLQSGVPSRFSGS

GSGTDFTLTISSLQPEDFATYYCQQANSAPTTFGQGTKVEIKRAAA

H5 Modified Clone R2G3 (SEQ ID NO: 11)

EVQLLESGGGLVQPGGSLRLSCAASGFTFSSYAMSWVRQASGKGLEWVS

DIYDGGGTNYADSVKGRFTTSRDDSKNTLYLQMNSLRAEDTAVYYCAKT

ADNFDYWGQGTLVTVSSGGGGSGGGGSGGGGSTDIQMTQSPSSLSASVG

-continued

DRVTITCRASQSISSYLNWYQQKPGKAPKLLIYAASTLQSGVPSRFSGS

GSGTDFTLTISSLQPEDFATYYCQQANSAPTTFGQGTKVEIKRAAA

H5 Modified Clone R1H6 (SEQ ID NO: 12)

EVQLLESGGGLVQPGGSLRLSCAASGFTESSYAMSWVRQAPGKGLEWVS

DIYDGGGTNYADSVKGRFTTSRDNSKNTMYLQMNSLRAEDTAVYYCAKT

ADNFDYWGQGTLVTVSSGGGGSGGGGSGGGGSTDIQMTQSPSSLSASVG

DRVTITCRASQSISSYLNWYQQKPGKAPKLLIYAASTLQSGVPSRFSGS

GSGTDFTLTISSLQPEDFATYYCQQANSAPTTFGQGTKVEIKRAAA

The amino acids underlined and in bold in SEQ ID NOs: 5 and 6 indicate the T to I difference between the two 286 residue sequences provided above. These two sequences encode useful peptides of the presently disclosed subject matter with properties encompassed by the presently disclosed subject matter.

One of ordinary skill in the art will appreciate that based on the sequences of the components of the antibodies disclosed herein they can be modified independently of one another with conservative amino acid changes, including, insertions, deletions, and substitutions, and that the valency could be altered as well. Amino acid changes (fragments and homologs) can be made independently in an antibody as well when they are being used in combination therapy.

In some embodiments, a protein or peptide of the presently disclosed subject matter, or a combination thereof, can be administered by a route selected from, including, but not limited to, intravenously, intrathecally, locally, intramuscularly, topically, orally, intra-arterially, parenterally, etc. Administration can be more than once. One of ordinary skill in the art can determine how often to administer the compound, the dose to be used, and what combination of other agents it can be administered with such as therapeutic agents and/or other drugs or compounds such as antimicrobial agents, anti-inflammatory agents, etc. One of ordinary skill in the will be able to determine when or if to use an additional agent and the route of administration.

In some embodiments, the present proteins or polypeptides are administered by injection. The parenteral route for administration of the polypeptide is in accordance with known methods, e.g., injection or infusion by intravenous, intraperitoneal, intramuscular, intra-arterial, subcutaneous, or intralesional routes. The protein or polypeptide may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 ug and 50 mg, in some embodiments between 50 ug and 10 mg, of the polypeptide. A typical pharmaceutical composition for intramuscular injection would be made up to contain, for example, 1-10 ml of sterile buffered water and between 10 ug and 50 mg, in some embodiments between 50 ug and 10 mg, of the polypeptide of the presently disclosed subject matter. Methods for preparing parenterally administrable compositions are well known in the art and described in more detail in various sources, including, for example, Genaro 1985, which is incorporated herein by reference in its entirety for all purposes.

When used in vivo for therapy, the antibodies of the subject presently disclosed subject matter are administered to the subject in therapeutically effective amounts (i.e., amounts that have desired therapeutic effect). They will normally be administered parenterally. The dose and dosage regimen will depend upon the degree of the disease or disorder, the characteristics of the particular antibody or immunotoxin used, e.g., its therapeutic index, the patient, and the patient's history. Advantageously the antibody or fragment thereof is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

For parenteral administration, the antibodies (such as scFv) will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

The antibody compositions used are formulated and dosages established in a fashion consistent with good medical practice taking into account the condition or disorder to be treated, the condition of the individual patient, the site of delivery of the composition, the method of administration, and other factors known to practitioners. The antibody compositions are prepared for administration according to the description of preparation of polypeptides for administration, infra.

The hybrid antibodies and hybrid antibody fragments include complete antibody molecules having full length heavy and light chains, or any fragment thereof, such as Fab, Fab', F(ab')$_2$, Fd, scFv, antibody light chains and antibody heavy chains. Chimeric antibodies which have variable regions as described herein and constant regions from various species are also suitable. See for example, U.S. Patent Application Publication No. 2003/0022244.

The peptides of the presently disclosed subject matter may be readily prepared by standard, well-established techniques, such as solid-phase peptide synthesis (SPPS) as described by Stewart et al., 1984; Bodanszky & Bodanszky, 1984. At the outset, a suitably protected amino acid residue is attached through its carboxyl group to a derivatized, insoluble polymeric support, such as cross-linked polystyrene or polyamide resin.

"Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method that utilized tert-butyloxcarbonyl as the α-amino protecting group, and the FMOC method which utilizes 9-fluorenylmethyloxycarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. 1990.

Peptide Modification and Preparation

Peptide preparation is described in the Examples. It will be appreciated, of course, that the proteins or peptides of the presently disclosed subject matter may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH$_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the presently disclosed subject matter are also contemplated as functional equivalents. Thus, a peptide in accordance with the presently disclosed subject matter treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicyclic and the like, to provide a water soluble salt of the peptide is suitable for use in the presently disclosed subject matter.

The presently disclosed subject matter also provides for analogs of proteins. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the presently disclosed subject matter are not limited to products of any of the specific exemplary processes listed herein.

The presently disclosed subject matter includes the use of beta-alanine (also referred to as β-alanine, β-Ala, bA, and βA, having the structure:

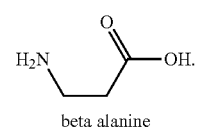

beta alanine

Sequences are provided herein which use the symbol "βA", but in the Sequence Listing submitted herewith "βA" is provided as "Xaa" and reference in the text of the Sequence Listing indicates that Xaa is beta alanine.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH2), and mono- and di-alkylamino groups such as methylamino, ethylamino, dimethylamino, diethylamino, methylethylamino and the like are examples of C-terminal blocking groups. Decarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and decarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al., 1990.

As discussed, modifications or optimizations of peptide ligands of the presently disclosed subject matter are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the presently disclosed subject matter are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from C1-C10 branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Antibody Formats and Preparation Thereof

Antibodies directed against proteins, polypeptides, or peptide fragments thereof of the presently disclosed subject matter may be generated using methods that are well known in the art. For instance, U.S. Pat. No. 5,436,157, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

In some embodiments, one or more antibodies or fragments thereof are used. In some embodiments, one or both antibodies are single chain, monoclonal, bi-specific, synthetic, polyclonal, chimeric, human, or humanized, or active fragments or homologs thereof. In some embodiments, the antibody binding fragment is scFV, F(ab')$_2$, F(ab)$_2$, Fab', or Fab.

For the preparation of monoclonal antibodies, any technique which provides for the production of antibody molecules by continuous cell lines in culture may be utilized. For example, the hybridoma technique originally developed by Kohler & Milstein, the trioma technique, the human B-cell hybridoma technique (Kozbor & Roder, 1983), and the EBV-hybridoma technique (Cole et al., 1985) may be employed to produce human monoclonal antibodies. In some embodiments, monoclonal antibodies are produced in germ-free animals.

In accordance with the presently disclosed subject matter, human antibodies may be used and obtained by utilizing human hybridomas (Cote et al., 1983) or by transforming human B cells with EBV virus in vitro (Cole et al., 1985). Furthermore, techniques developed for the production of "chimeric antibodies" (Morrison et al., 1984; Neuberger et al., 1984; Takeda et al., 1985) by splicing the genes from a mouse antibody molecule specific for epitopes of SLLP polypeptides together with genes from a human antibody molecule of appropriate biological activity can be employed; such antibodies are within the scope of the presently disclosed subject matter. Once specific monoclonal antibodies have been developed, the preparation of mutants and variants thereof by conventional techniques is also available.

Various techniques have been developed for the production of antibody fragments of humanized antibodies. Traditionally, these fragments were derived via proteolytic digestion of full-length antibodies (see e.g., Morimoto & Inouye, 1992; Brennan et al., 1985). However, these fragments can now be produced directly by recombinant host cells. Alternatively, Fab'-SH fragments can be directly recovered from *E. coli* and chemically coupled to form F(ab')$_2$ fragments (Carter et al., 1992a). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). See PCT International Patent Application Publication No. WO 1993/16185; U.S. Pat. Nos. 5,571,894; 5,587,458. The antibody fragment may also be a "linear antibody", e.g., as described in U.S. Pat. No. 5,641,870, for example. Such linear antibody fragments may be monospecific or bispecific.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see e.g., U.S. Pat. Nos. 4,975,369; 5,075,431; 5,081,235; 5,169,939; 5,202,238; 5,204,244; 5,231,026; 5,292,867; 5,354,847; 5,472,693; 5,482,856; 5,491,088; 5,500,362; and 5,502,167). Detailed methods for preparation of chimeric (humanized) antibodies can be found in U.S. Pat. No. 5,482,856. A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see e.g., Jones et al., 1986; Riechmann et al., 1988; Presta, 1992, PCT International Patent Application Publication No. WO 92/02190, U.S. Patent Application Publication No. 2006/0073137, and U.S. Pat. Nos. 5,225,539; 5,530,101; 5,585,089; 5,693,761; 5,693,762; 5,714,350; 5,766,886; 5,770,196; 5,777,085; 5,821,123; 5,821,337; 5,869,619; 5,877,293; 5,886,152; 5,895,205; 5,929,212; 6,054,297; 6,180,370; 6,407,213; 6,548,640; 6,632,927; 6,639,055; and 6,750,325.

In some embodiments, this presently disclosed subject matter provides for fully human antibodies. Human antibodies consist entirely of characteristically human polypeptide sequences. The human antibodies of this presently disclosed subject matter can be produced in using a wide variety of methods (see e.g., U.S. Pat. No. 5,001,065, for review).

Typically, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al, 1986; Riechmann et al., 1988); Verhoeyen et al., 1988), by substituting hypervariable region sequences for the corresponding sequences of a human "acceptor" antibody. Accordingly, such "humanized" antibodies are chimeric antibodies (see e.g., U.S. Pat. Nos. 4,816,567 and 5,482,856) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Another method for making humanized antibodies is described in U.S. Patent Application Publication No. 2003/0017534, wherein humanized antibodies and antibody preparations are produced from transgenic non-human animals. The non-human animals are genetically engineered to contain one or more humanized immunoglobulin loci that are capable of undergoing gene rearrangement and gene conversion in the transgenic non-human animals to produce diversified humanized immunoglobulins.

In some embodiments, the choice of human variable domains, both light and heavy, to be used in making the humanized antibodies is very important to reduce antigenicity. According to the so-called "best-fit" method, the sequence of the variable domain of a rodent antibody is screened against a library of known human variable-domain sequences or a library of human germline sequences. The human sequence that is closest to that of the rodent can then be accepted as the human framework region for the humanized antibody (Sims et al., 1993; Chothia & Lesk, 1987). Another method uses a particular framework region derived from the consensus sequence of all human antibodies of a particular subgroup of light or heavy chains. The same framework may be used for several different humanized antibodies (Carter et al., 1992b; Presta et al., 1993). Other methods designed to reduce the immunogenicity of the antibody molecule in a human patient include veneered antibodies (see e.g., U.S. Pat. No. 6,797,492 and U.S. Patent Application Publication Nos. 2002/0034765 and 2004/0253645) and antibodies that have been modified by T-cell epitope analysis and removal (see e.g., U.S. Patent Application Publication No. 2003/0153043 and U.S. Pat. No. 5,712,120).

It is important that when antibodies are humanized they retain high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The antibody moieties of this presently disclosed subject matter can be single chain antibodies.

Antibodies directed against proteins, polypeptides, or peptide fragments thereof of the presently disclosed subject matter may be generated using methods that are well known in the art. For instance, U.S. Pat. No. 5,436,157, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

The hybrid antibodies and hybrid antibody fragments include complete antibody molecules having full length heavy and light chains, or any fragment thereof, such as Fab, Fab', F(ab')$_2$, Fd, scFv, antibody light chains and antibody heavy chains. Chimeric antibodies which have variable regions as described herein and constant regions from various species are also suitable. See for example, U.S. Patent Application No. 2003/0022244.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')$_2$, and single chain Fv (scFv) fragments.

In some embodiments, the specific binding molecule is a single-chain variable analogue (scFv). The specific binding molecule or scFv may be linked to other specific binding molecules (for example other scFvs, Fab antibody fragments, chimeric IgG antibodies (e.g., with human frameworks)) or linked to other scFvs of the presently disclosed subject matter so as to form a multimer which is a multi-specific binding protein, for example a dimer, a trimer, or a tetramer. Bi-specific scFvs are sometimes referred to as diabodies, tri-specific such as triabodies and tetra-specific such as tetrabodies when each scFv in the dimer, trimer, or tetramer has a different specificity. Diabodies, triabodies and tetrabodies can also be monospecific, when each scFv in the dimer, trimer, or tetramer has the same specificity.

In some embodiments, techniques described for the production of single-chain antibodies (U.S. Pat. No. 4,946,778, incorporated by reference herein in its entirety) are adapted to produce protein-specific single-chain antibodies. In some embodiments, the techniques described for the construction of Fab expression libraries (Huse et al., 1989) are utilized to allow rapid and easy identification of monoclonal Fab fragments possessing the desired specificity for specific antigens, proteins, derivatives, or analogs of the presently disclosed subject matter.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which bind the antigen therefrom at any epitopes present therein.

Monoclonal antibodies directed against full length or peptide fragments of a protein or peptide may be prepared using any well known monoclonal antibody preparation procedures, such as those described, for example, in Harlow & Lane, 1988; Tuszynski et al., 1988). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided.

The presently disclosed subject matter encompasses more than the specific fragments and humanized fragments disclosed herein. In some embodiments, the antibody is selected from the group consisting of a single chain antibody, a monoclonal antibody, a bi-specific antibody, a chimeric antibody, a synthetic antibody, a polyclonal antibody, or a humanized antibody, or active fragments or homologs thereof.

A nucleic acid encoding the monoclonal antibody obtained using the procedures described herein may be cloned and sequenced using technology which is available in the art, and is described, for example, in Wright et al., 1992)

and the references cited therein. Further, the antibody of the presently disclosed subject matter may be "humanized" using the technology described in Wright et al., 1992 and in the references cited therein, and in Gu et al., 1997.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Green & Sambrook, 2012.

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton & Barbas, 1994). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

In accordance with the presently disclosed subject matter, human antibodies may be used and obtained by utilizing human hybridomas (Cote et al., 1983) or by transforming human B cells with EBV virus in vitro (Cole et al., 1985). Furthermore, techniques developed for the production of "chimeric antibodies" (Morrison et al., 1984; Neuberger et al., 1984; Takeda et al., 1985).

The procedures just presented describe the generation of phage which encode the Fab portion of an antibody molecule. However, the presently disclosed subject matter should not be construed to be limited solely to the generation of phage encoding Fab antibodies. Rather, phage which encode single chain antibodies (scFv/phage antibody libraries) are also included in the presently disclosed subject matter. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991. Panning of phage so generated for the isolation of a desired antibody is conducted in a manner similar to that described for phage libraries comprising Fab DNA.

The presently disclosed subject matter should also be construed to include synthetic phage display libraries in which the heavy and light chain variable regions may be synthesized such that they include nearly all possible specificities (Barbas, 1995; de Kruif et al., 1995).

In the production of antibodies, screening for the desired antibody can be accomplished by techniques known in the art, e.g., ELISA (enzyme-linked immunosorbent assay). Antibodies generated in accordance with the presently disclosed subject matter may include, but are not limited to, polyclonal, monoclonal, chimeric (i.e., "humanized"), and single chain (recombinant) antibodies, Fab fragments, and fragments produced by a Fab expression library.

In some embodiments, the presently disclosed H5 scFv and variants thereof can be purified after expression in *E. coli*. By way of example and not limitation, *E. coli* can be used as a host for recombinant protein production, including immunoglobulin fragments, as can mammalian cells. *E. coli* can be employed to produce target proteins including but not limited to the scFvs and variants thereof of the presently disclosed subject matter in large quantities (see e.g., Verma et al., 1998).

Since scFvs contain 2 disulfide bonds, a leader sequence (PelB) to direct the antibody fragment into the *E. coli* periplasmic space can also be used as desired. The leader can then be removed physiologically once the scFv reaches the periplasmic space. The latter space between the inner and outer membranes of Gram negative bacteria is more oxidizing compared to the cytoplasm as it contains chaperonin equivalents and disulfide isomerases (Skerra & Pluckthun, 1988).

In some embodiments, the *E. coli* strain used can be BL21 DE3, which expresses T7 polymerase. This polymerase transcribes DNA sequences up to five times faster than the native *E. coli* RNA polymerase and enables strong induction protein expression with isopropyl β-D-1-thiogalactopyranoside (IPTG). Additionally, BL21 DE3 lacks the Lon protease (Gottesman, 1996) and outer membrane protease OmpT (Grodberg & Dunn, 1988).

The presently disclosed H5 can be also purified via affinity HPLC using a protein L column, which preferentially binds scFv light chains.

Substantially pure peptide obtained as described herein may be purified by following known procedures for protein purification, wherein an immunological, enzymatic, or other assay is used to monitor purification at each stage in the procedure. Protein purification methods are well known in the art, and are described, for example in Deutscher et al., 1990.

It is common in the field of recombinant humanized antibodies to graft murine CDR sequences onto a well-established human immunoglobulin framework previously used in human therapies such as the framework regions of Herceptin [Trastuzumab]. In the construction of the human ScFv disclosed in this study a novel approach was taken to engineer a unique human immunoglobulin framework in order to avoid previous intellectual property issues surrounding the Herceptin framework [Genentech]. The humanized ScFv disclosed is thus anticipated to constitute a distinct patentable composition of matter.

In some embodiments, when used in vivo for therapy, the antibodies of the subject presently disclosed subject matter are administered to the subject in therapeutically effective amounts (i.e., amounts that have desired therapeutic effect). They will normally be administered parenterally. The dose and dosage regimen will depend upon the degree of the infection, the characteristics of the particular antibody or immunotoxin used, e.g., its therapeutic index, the patient, and the patient's history. Advantageously the antibody or immunotoxin is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

In some embodiments, for parenteral administration, the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

Pharmaceutical Compositions and Administration

The presently disclosed subject matter is also directed to methods of administering the compounds of the presently disclosed subject matter to a subject.

Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the presently disclosed subject matter to a subject in need thereof. Compounds identified by the methods of the presently disclosed subject matter can be administered with known compounds or other medications as well.

The pharmaceutical compositions useful for practicing the presently disclosed subject matter may be administered to deliver a dose of between 1 ng/kg/day and 100 mg/kg/day.

The presently disclosed subject matter encompasses the preparation and use of pharmaceutical compositions comprising a compound useful for treatment of the diseases and disorders disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The compositions of the presently disclosed subject matter may comprise at least one active peptide, one or more acceptable carriers, and optionally other peptides or therapeutic agents.

For in vivo applications, the peptides of the presently disclosed subject matter may comprise a pharmaceutically acceptable salt. Suitable acids which are capable of forming such salts with the compounds of the presently disclosed subject matter include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents, or adjuvants. The compositions are in some embodiments sterile and nonpyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum metahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g., 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the presently disclosed subject matter can be prepared in a manner fully within the skill of the art.

The peptides of the presently disclosed subject matter, pharmaceutically acceptable salts thereof, or pharmaceutical compositions comprising these compounds may be administered so that the compounds may have a physiological effect. Administration may occur enterally or parenterally; for example, orally, rectally, intracisternally, intravaginally, intraperitoneally, locally (e.g., with powders, ointments or drops), or as a buccal or nasal spray or aerosol. Parenteral administration is preferred. Particularly preferred parenteral administration methods include intravascular administration (e.g., intravenous bolus injection, intravenous infusion, intra-arterial bolus injection, intra-arterial infusion and catheter instillation into the vasculature), peri- and intra-target tissue injection (e.g., peri-tumoral and intra-tumoral injection), subcutaneous injection or deposition including subcutaneous infusion (such as by osmotic pumps), intramuscular injection, and direct application to the target area, for example by a catheter or other placement device.

Where the administration of the peptide is by injection or direct application, the injection or direct application may be in a single dose or in multiple doses. Where the administration of the compound is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the presently disclosed subject matter is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

A pharmaceutical composition of the presently disclosed subject matter may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the presently disclosed subject matter may further comprise one or more additional pharmaceutically active agents. Particularly contemplated additional agents include anti-emetics and scavengers such as cyanide and cyanate scavengers.

Controlled- or sustained-release formulations of a pharmaceutical composition of the presently disclosed subject matter may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Genaro, 1985, which is incorporated herein by reference.

Typically, dosages of the compound of the presently disclosed subject matter which may be administered to an animal, in some embodiments a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In some embodiments, the dosage of the compound will vary from about 1 mg to about 10 g per kilogram of body weight of the animal. In another aspect, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The presently disclosed subject matter also includes a kit comprising the composition of the presently disclosed subject matter and an instructional material which describes adventitially administering the composition to a cell or a tissue of a subject. In some embodiments, this kit comprises a (in some embodiments sterile) solvent suitable for dissolving or suspending the composition of the presently disclosed subject matter prior to administering the compound to the subject.

As used herein, an "instructional material" includes a publication, a recording, a diagram, or any other medium of expression which can be used to communicate the usefulness of the peptide of the presently disclosed subject matter in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the presently disclosed subject matter may, for example, be affixed to a container which contains the multimeric peptide of the presently disclosed subject matter or be shipped together with a container which contains the peptide. Alternatively, the instructional material may be shipped separately from the container with the intention that the instructional material and the compound be used cooperatively by the recipient.

Idiopathic Pulmonary Fibrosis

Fibronectin (Fn) has been identified as a potential target for early onset Idiopathic Pulmonary Fibrosis (IPF). IPF produces similar scarring and thickening of tissue found in other forms of respiratory diseases, making it difficult to identify the exact cause of the disease. A possible pathway in the development of fibrosis involves a strained conformation of Fn. The presently disclosed subject matter provides an antibody called H5 to bind to the disease-state model, which is a strained conformation of Fn, called FnIII9-4G-10 (4G). Representative antibodies that bind better to 4G than H5 does are also provided herein. By way of example and not limitation, mutations were introduced into the H5 sequence by mutagenesis and amplified through error prone PCR to develop a diverse library of antibodies. This library was then screened using phage display and multiple ELISA rounds. Clone strength was quantified through an absorbance ratio, where higher ratios indicated better binding performance. Testing helped to identify 23 clones that outperformed H5; however, when the clones were sequenced, four were identified to be different than H5.

Pulmonary fibrosis (PF) is a disease in which lung tissue becomes thick, stiff, and scarred over time. Scarred lung tissue hinders the movement of oxygen from the lungs into the bloodstream, thus reducing the amount of available oxygen in circulation for the body (see e.g., the website of the National Heart, Lung, and Blood Institute; King et al., 2011). PF is further characterized by the deposition of extracellular matrix (ECM) proteins, such as fibronectin (Fn), that are responsible for the breakdown of functional alveolar units, which results in respiratory failure (Datta et al., 2011). While a controllable amount of ECM production benefits the body, such as through scar tissue for injury healing, an uncontrollable amount can be fatal, such as in Idiopathic Pulmonary Fibrosis (IPF; Raghu & Mikacenic, 2018). IPF, one of at least 200 different forms of PF, is a chronic state of fibrosis that leads to an irreversible decline in lung functionality. IPF affects 1 out of 200 adults over the age of 65, with 50,000 adults diagnosed and another 40,000 deaths from IPF each year (Pulmonary Fibrosis Foundation, 2018). Immediate treatment is required in order to slow the progression of IPF. Therefore, it is imperative to continue research to better detect and understand the pathways of IPF.

The presently disclosed representative H5 antibody binds to the strained conformation of Fn. Two different fragments were designed to model the strained and normal conformations in the relevant region of Fn. The strained version of Fn, FnIII9-4G-10 (4G), includes the addition of four glycines between the 9th and 10th type III repeats, which is a mutation that decreases binding affinity of Fn for the α5β1 integrin. The engineered Fn was used in experiments to model the change in response to mechanical forces in disease-states and to prove the existence of Fn's integrin switch. The normal version, FnIII9*10 (9*10), expresses the normal folding of Fn in the 9th and 10th type III repeats. Thus, modifications of the H5 antibody to improve binding to strained Fn and prohibit or limit binding to regular Fn are provided in accordance with the presently disclosed subject matter through directed evolution, phage display, and ELISAs.

As disclosed herein, the exemplary H5 antibody of the presently disclosed subject matter has been identified to possess a "local maximum" binding affinity for 4G. However, the binding has not reached the "absolute maximum", or the best potential binding state. The basis for directed evolution is the production of a library with a maximal diversity of genes in order to reach fitness peaks. Therefore, also disclosed herein are experiments to develop a library of H5 antibody clones diverse enough to reach the "absolute maximum" binding affinity for 4G. In some embodiments, random mutagenesis is employed to introduce random mutations into the current H5 antibody DNA sequence (Cadwell & Joyce, 1992).

Phage display technology is used to improve the H5 clone's binding affinity for 4G and prohibit or limit binding to 9*10. Phage display is a process used to present polypeptides on the surface of lysogenic filamentous bacteriophages through manipulation of the phage's genotype (Bazan et al., 2012). Its use in creating antibodies was developed within a larger framework called directed evolution, which uses a trial-and-error approach to introduce genetic variations in antibodies in order to enhance at least one antibody's target binding ability (Trafton, 2010). The technique earned publicity recently when its contributors received the Nobel Prize in Chemistry (Offord & Grens, 2018). Through this framework, in some embodiments provided are antibodies and antigen-binding fragments thereof that are modified through optimization of the diversity of the antibody library by mutagenesis through error prone PCR, while also confirming that protein adaptations can be successful and be produced on a faster time scale.

Finally, ELISAs were performed, and the clones identified to outperform H5 were separated from the phage for further antibody characterization. Sequences of the clones were analyzed as disclosed herein.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for the Examples

Creating a Library of H5 Clones. Mutagenesis was performed using the GeneMorph II Random Mutagenesis Kit with H5 as the DNA template. First, a master mix was created including water, Mutazyme II Reaction Buffer, dNTP mix, forward and backward primers, Mutazyme II DNA Polymerase, and the H5 DNA template. The sequences of the primers employed were 5'-CCAAGGCATGCAAAT-TCTATTTCAA-3' (SEQ ID NO: 13) and 5'-TGGTGAT-GATGATGTGCGGC-3' (SEQ ID NO: 14). The reaction took place in a thermocycler for 33 cycles, with the annealing temperature set to 53.2° C.

The primers used in these reactions, whose sequences were determined by the Primer3 software, ensured mutations in the full length H5 antibody, while a separate library with only mutations in the heavy chain of H5 was prepared beforehand through a similar process. After the first error prone PCR, sequential reactions were performed wherein the previous product of error prone PCR was used as DNA template for the next reaction. Two sequential error prone PCRs were performed for a total of three reactions to maximize the diversity of the library, since errors were compounded with each sequential reaction.

Next, digestion of a vector was performed. The vector pR2 was digested so that the section of DNA coding for the antibodies prepared by error prone PCR could be inserted into the vector. The vector pR2 compiled genetic information for the antibody clones as well as antibiotic resistance to ampicillin. The helper phage added later contained genetic information for kanamycin resistance. Antibiotics were used in plates and media throughout the process to ensure the exclusive growth of the TG1 bacterial cell line without contamination. Digestion was performed by combining the products from mutagenesis and the pR2 vector, each with water, buffer, and the restriction enzymes BspEI and NotI, purchased from New England BioLabs. The reactions were placed in a thermocycler for one-hour incubations at 37° C.

After incubation, gel electrophoresis was used to run the products with a purple loading dye through a thick agarose gel. The correctly sized vector products, which excluded the insert identical in size to the H5 clone DNA insert, were excised and purified with the QIAquick Gel Extraction Kit from QIAGEN. The size of the insert was 645 base pairs, while the pR2 vector excluding the insert was 4618 base pairs. A DNA ladder was used for reference to determine which bands to excise from the agarose gel. Ligation was then used to combine the vector with the H5 clone inserts. A master mix was prepared and placed into the thermocycler at 16° C. overnight. The ligation products were purified with the QIAGEN PCR Purification Kit.

After ligation and a heat inactivation at 70° C., the pR2 vector with H5 clone library inserts were ready to be introduced into bacterial cells, so that the antibody library could be displayed on the protein coats of phages. The vectors were introduced into TG1 cells through electroporation, in which the bacterial cell membranes were opened using a pulse of electricity produced by the Lucigen Electrocompetent Cells. The protocol recommended electroporation at 10 µF, 600 Ohms, and 1800 Volts. After electroporation, the TG1 cells were grown on TYE plates. In order to confirm the diversity of the library, DNA of 20 randomly selected colonies from the plates were amplified with PCR and sequenced. Further experimentation continued with the heavy chain varied library.

Determining the Best Clones: Phage Display. To prepare the clones for phage display, the antibody library was grown in a culture of 2×YT media supplemented with 4% glucose and 100 mg/mL carbenicillin until culture reached an OD600 of 0.5. The OD600 was measured using a NanoDrop Spectrophotometer. Carbenicillin was used in place of ampicillin because of its greater stability (Addgene, 2017). Then, $1 \times 10^{12}$ KM13 helper phages were added to the culture and the culture was incubated overnight. KM13 helper phages encode for 5 different proteins that are expressed on its protein coat: P3, P6, P7, P8, and P9. P3, P6, P7, and P9 are expressed at 5 copies per particle on the ends of the KM13 helper phage. There is a P7 and P9 cap at one end and a P3 and P6 cap the other end. P3 is specifically responsible for bacterial cell recognition and infection (Sidhu, 2001). The pR2 vector combines with the helper phage genetic material in order to display the antibody clones on the surface of the P3 proteins. In these experiments, the KM13 helper phage were wild type phages and contained only the genetic material for normal P3 proteins. When helper phages were added to the culture, they infected the bacteria and produced antibodies for display on their protein coats. The following day, a series of centrifugation and precipitation steps were performed to isolate the phages for selection.

For phage display, two 96-well maleimide plates were prepared for cross-screening through a series of wash steps and the addition of Fn fragments (one plate with 9*10 fragments and another with 4G fragments). Purified phages were added to 5% MPBS (5% w/v milk powder in PBS) and 100 µL of phage in MPBS was then added to each well of the 96-well plate exposed to 9*10 fragments. The plates were then incubated for one hour on a shaker at room temperature. The supernatant was collected from the plates as it represents phage that did not bind to 9*10. The supernatant was then added to the 96-well plate exposed to 4G and incubated for one hour on a shaker at room temperature. After the one hour, plates were washed to remove antibodies that did not bind to 4G. Lastly, trypsin protease was added to the 4G plate to elute the phages that bound to 4G. Trypsin protease specifically cuts the c-Myc tag between the antibody and P3 of KM13 helper phages.

Figure 11:
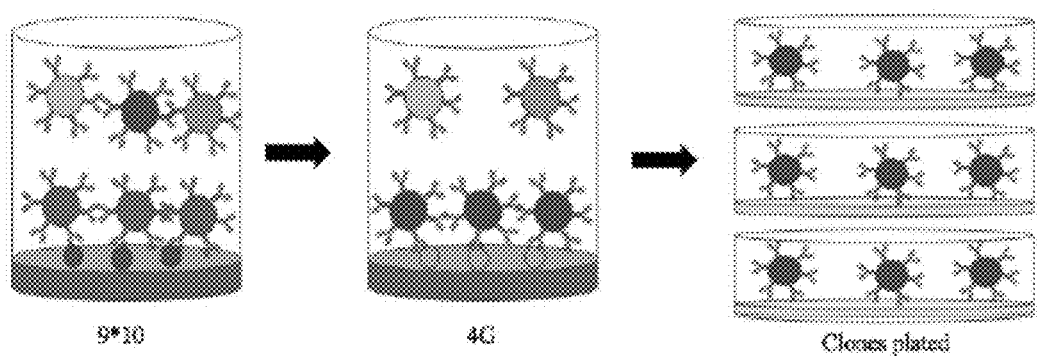
FIG. 11 depicts an exemplary strategy for the selection of clones in phage display, illustrating an exemplary process for negative and positive selection. First, antibodies presented on phages are exposed to 9*10 Fn fragments on a maleimide plate (left panel). The supernatant from that plate is transferred to a maleimide plate with 4G fragments (middle panel). Unbound clones are disposed of and bound clones are removed from the plate and transferred to a TYE plate to grow (right panel).
Figure 13:
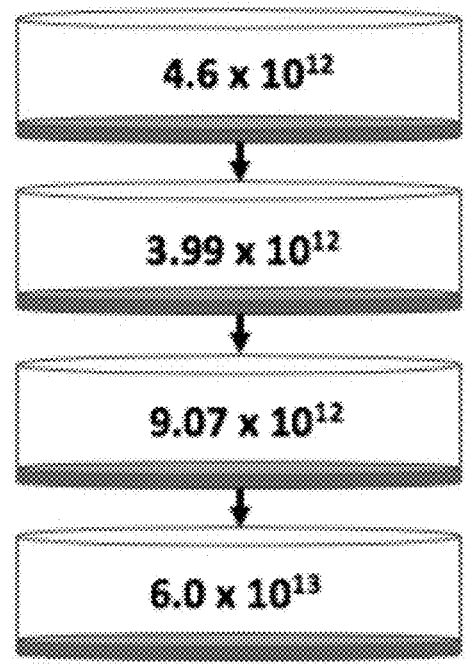
FIG. 13 depicts phage titers during negative and positive selection. After each round of screening, phage titers were measured using a NanoDrop Spectrophotometer at OD260. Four rounds of selection were performed, and the goal of each was to narrow down the number of clones containing different sequences while keeping the total number of phages the same. The phage titers were a measure of the total number of phages in each round.

The selected phages were then amplified. The TG1 cells were grown in 2×YT media with no antibiotic until an OD600 of 0.5 was reached. Eluted phages from the selection round were added to 30 mL of culture and incubated for one hour at 37° C. After an hour, the culture was centrifuged to obtain a pellet, and that pellet was resuspended in 2×YT media. 161 µL of culture was added to six TYE plates supplemented with carbenicillin and 4% glucose. These plates were then incubated at 37° C. overnight for growth of the selected phages with bacteria for the next round of selection. The next day the bacteria was scraped from plates and used to perform another selection round by repeating the procedure beginning again with selection with maleimide-activated plates. Maleimide-activated plates, a special modification to the normal phage display protocol, were also used in ELISA testing and will be elaborated in that section. The phage display protocol was repeated for a total of four rounds of selection. The process of positive and negative selection, wherein only the phages of antibody fragments that bound to 4G but not 9*10 proceeded to growth and the next round of selection, is depicted in FIG. 11.

Figure 12:
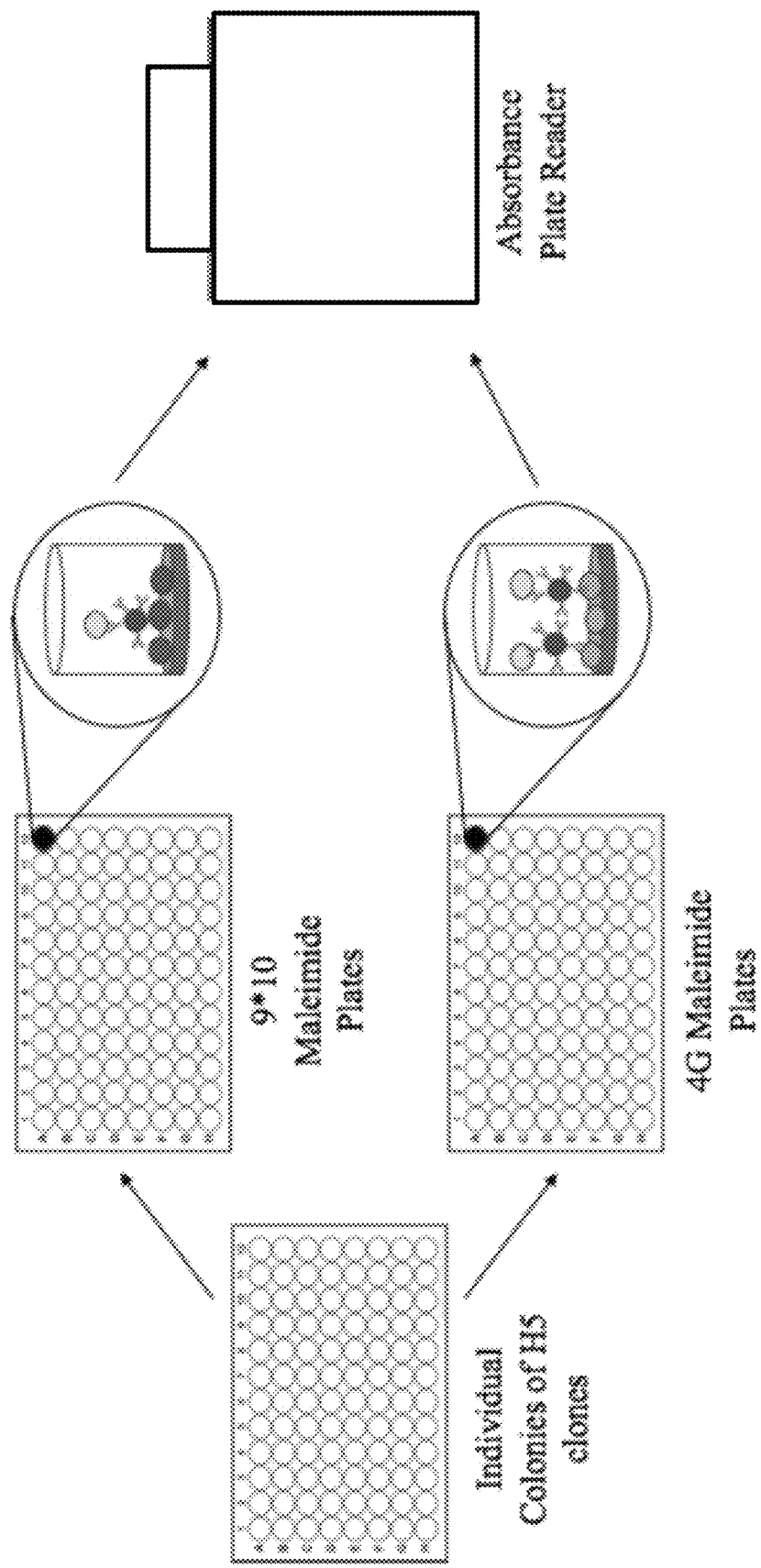
FIG. 12 depicts an exemplary strategy for ELISA selection of clones, illustrating an exemplary process for ELISA testing. Individual colonies were picked and placed in round-bottom 96 well plates (left panel). In each plate, an H5 colony was placed in well A1. Colonies were grown and transferred to maleimide-activated plates containing 9*10 and 4G Fn fragments (panel second to left). An HRP-conjugated secondary antibody was added to each well in the plates (panel third to left). Finally, absorbances from each plate were measured by a plate reader and used to calculate 4G/9*10 ratios (right most panel).
Figure 14:
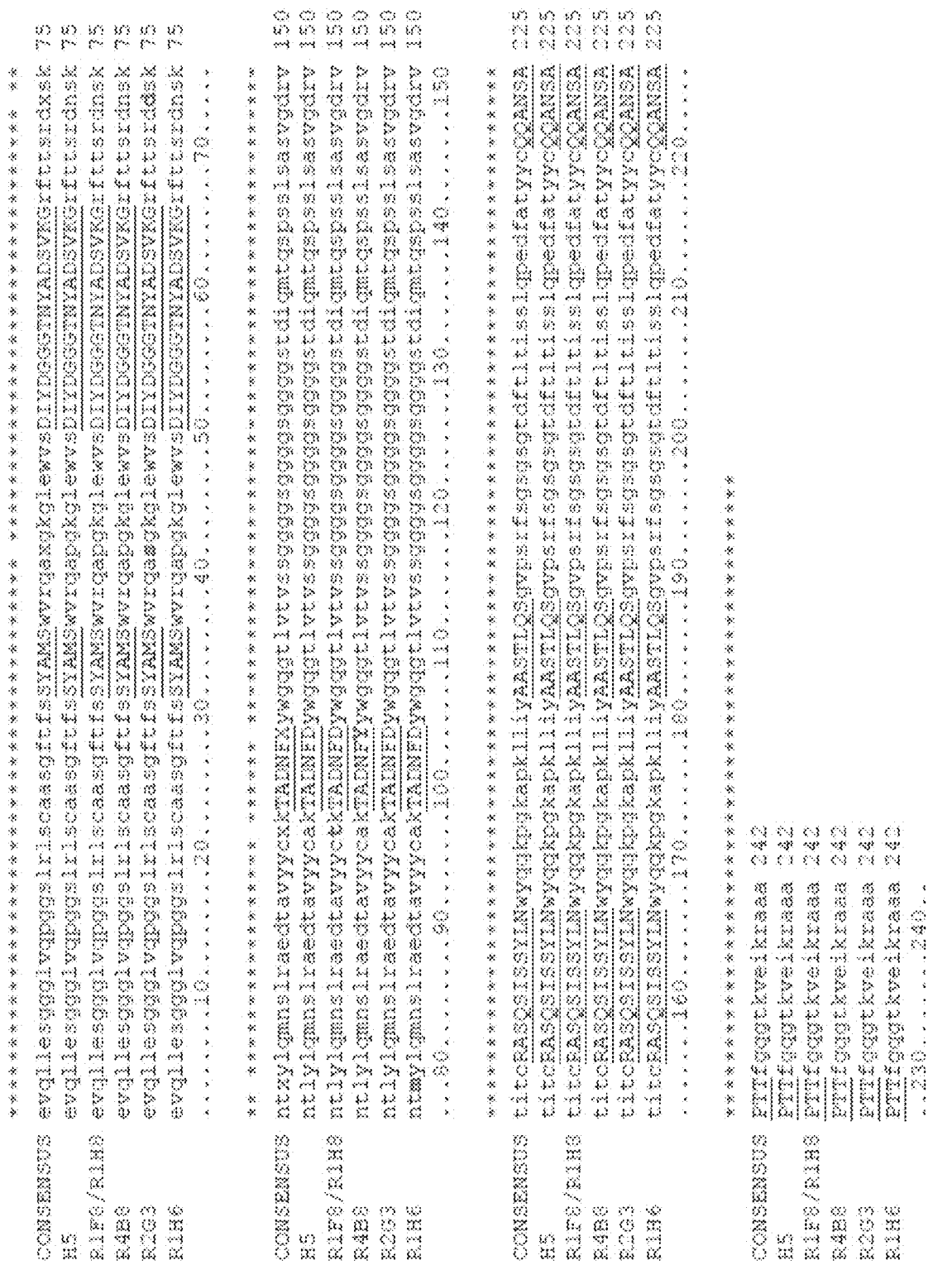
FIG. 14 is a summary of amino acid sequences of exemplary antibody clones along with a consensus sequence (SEQ ID NO: 8). Patterns of mutations in H5 clone (SEQ ID NO: 1) amino acid sequences contributed to the continuous work of finding a scFv that bound better to 4G than did H5. Modifications of amino acids are shown in bold red text with reference to known CDRs (uppercase and underlined). In R1F8 (SEQ ID NO: 9), alanine 96 was replaced with a threonine. In R4B8 (SEQ ID NO: 10), aspartic acid 103 in CDR3 was replaced by a tyrosine. In R2G3 (SEQ ID NO: 11), proline 41 between CDR1 and CDR2 was replaced by a serine, and asparagine 73 between CDR2 and CDR3 was replaced by an aspartic acid. In R1H6 (SEQ ID NO: 12), leucine 78 between CDR2 and CDR3 was replaced by a methionine.

Determining the Best Clones: ELISA Testing. Basic quantitative data with sandwich ELISAs of the HRP-conjugated antibodies was produced to compare binding of the selected clones on 4G and 9*10. For each ELISA round, a 96-well consisted of H5 and clone colonies. Well A1 consisted of an H5 colony (control) while the remaining 95 wells consisted of a colony picked from the TYE plates from the previous selection round. The plate was grown and then colonies were transferred to two maleimide plates: one with 4G Fn fragments and one with 9*10 Fn fragments. HRP anti-M13 conjugate as the secondary antibody and TMB substrate solution for detection of the HRP was added to each well of the plate. The plates were incubated for no longer than 30 minutes under aluminum foil to avoid degradation of HRP. Then, 1M sulfuric acid was added to each well to stop the reaction. Then, a plate reader was used to measure absorbance signals from each well. These absorbance values were used to quantify clone performance. The entire process described is illustrated in FIG. 12.

Maleimide-activated plates were used for ELISAs in the process of screening clones. Maleimide is a functional group that reacts with free sulfhydryl groups to form stable thioether linkages (Thermo Fischer Scientific Catalogue No. 15150). Maleimide reacted with the N-termini cysteines of the fibronectin fragments to ensure the proper display of the fragments on the plate wells. The method using maleimide-activated plates, also used in positive and negative selection, was preferred over regular polystyrene plates because the fibronectin fragments used were prone to unfolding and therefore, improper display of epitopes (Cuccuru et al., 2012). Before use, the plates were washed with buffer and blocked with cysteine. TCEP Disulfide Reducing Gel was used to reduce the disulfide bonds in the fibronectin fragments before the fragments were added to the ELISA plates.

Example 1

Recombinant Fn Fragments and Antibody Selection

Figure 1B:
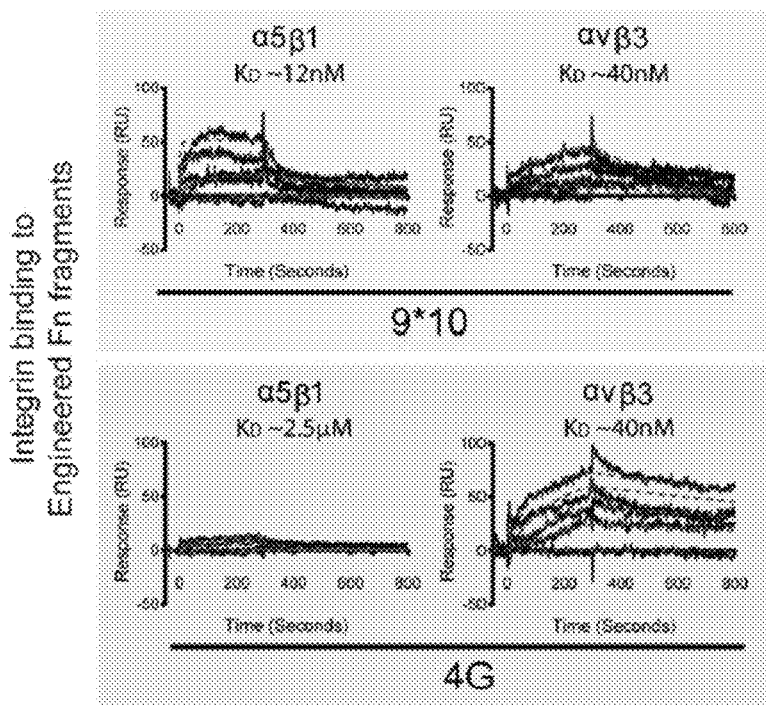
Figure 1C:
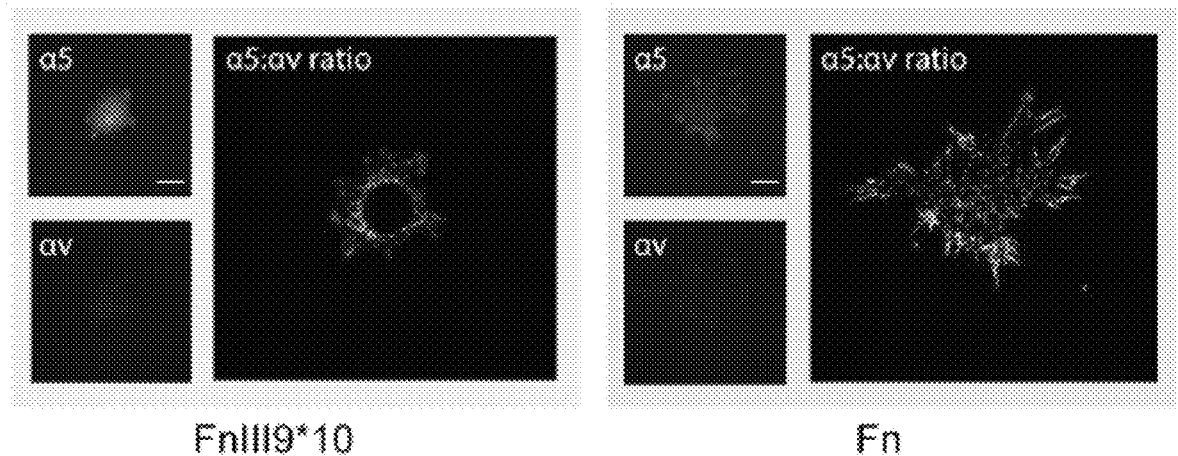
Figure 1C:
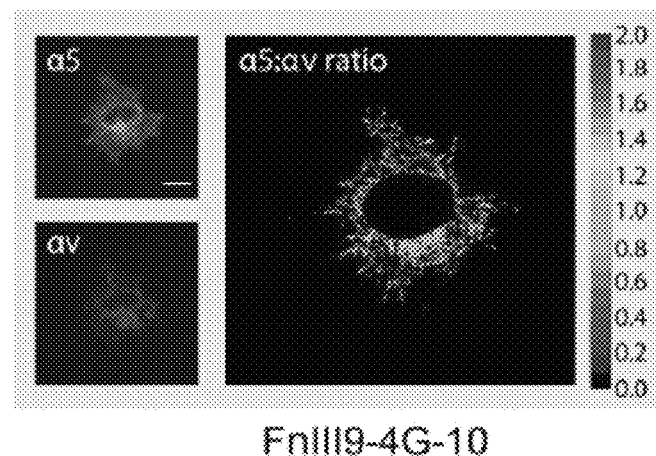
Figure 2:
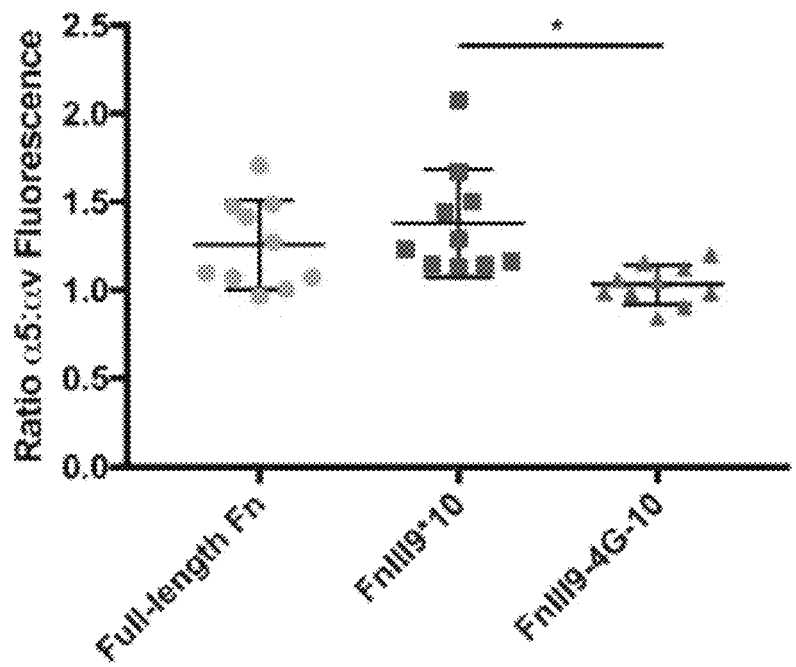
FIG. 2 is a plot of quantitation of integrin staining intensity on Fn fragments and full-length Fn. Human foreskin fibroblasts were seeded onto fragments or full-length Fn in serum-free media, fixed at 30 minutes, and stained for α5 and αv as described herein (see e.g., EXAMPLE 1). Ratiometric images of each cell were generated by thresholding individual channels and dividing α5 by αv. Median α5: αv values were calculated for each image and compared using one-way ANOVA with Tukey's post-test, N=10 cells for each condition. *p<0.01.

To test the existence of Fn's integrin switch and to demonstrate its relevance in vivo, single-chain antibodies (scFv) capable of detecting a ~1 nm extension in the conformation of Fn's integrin binding domain through directed evolution and screening against recombinant Fn fragments that mimic the force-induced structural states predicted in silico were developed and are disclosed herein. Engineered Fn fragments spanning the 9th and 10th type III repeats of Fn were produced as reported (Martino et al., 2009), in which a Leu1408Pro mutation (van der Walle et al., 2002) was created to stabilize the spatial and angular orientation of the pentapeptide sequence PHSRN (SEQ ID NO: 7) with respect to RGD (denoted FnIII9*10). A second, extended conformation, variant was created by inserting a tetraglycine (GGGG; SEQ ID NO: 17) peptide linker between the 9th and 10th type III repeats, increasing the separation between the PHSRN pentapeptide (SEQ ID NO: 7) and RGD sites from 3.4 nm to approximately 4.3 nm (denoted FnIII9-4G-10; see FIG. 1A). Surface plasmon resonance (SPR) experiments demonstrated that the insertion of the tetraglycine (SEQ ID NO: 17) linker was sufficient to decrease in vitro α5β1 integrin binding affinity from 12 nM to ~2.5 μM whereas integrin αvβ3 affinity predictably remained relatively constant at ~40 nM (FIG. 1B). Immunofluorescence staining of integrins on human foreskin fibroblasts cultured on these Fn fragments confirmed that this molecular modification resulted in a switch in the integrin binding profile from α5β1 and αvβ3 to predominantly αvβ3 at the cellular level (FIG. 1C; FIG. 2), supporting earlier reports of FnIII9*10 fragment's ability to engage α5β1 integrins preferentially (Martino et al., 2009).

Figure 3:
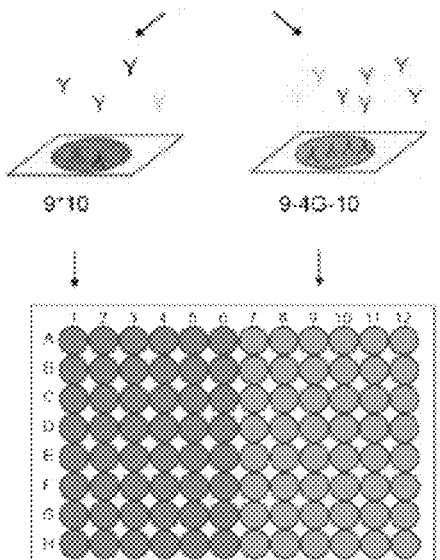
FIG. 3 presents the results of ELISA assay for selection of scFv antibodies following phage display panning on Fn fragments.

Phage display was used to isolate scFv antibodies capable of discriminating between two engineered Fn fragments that spanned a force-sensitive portion of Fn (FnIII9-10) intended to model molecular strain within Fn. Fn fragments were produced by recombinant protein production methods, FnIII9*10: stabilized mutant with Leu1408Pro mutation to stabilize the spatial orientation of the synergy site (PHSRN; SEQ ID NO: 7) with respect to the RGD site (Martino et al., 2009), FnIII9-4G-10: mutant with a tetraglycine (SEQ ID NO: 17) insertion in the linker region between 9th and 10th type III repeats (Markowski et al., 2012). Binding kinetics of FnIII9'10 variants to integrins α5β1 and αvβ3 were analyzed through surface plasmon resonance using a Biacore 2000 (Biacore Lifesciences, GE Healthcare, Chicago, Illinois, United States of America) and data analysis was performed with Scrubber 2 and ClampXP software (Center for Biomolecular Interactions Analysis, University of Utah, Salt Lake City, Utah, United States of America; see also Morton et al., 1995; Morton & Myszka, 1998; Myszka et al., 1998). Integrins (100 μg/mL; R&D Systems, Minneapolis, Minnesota, United States of America) were immobilized onto sensor chips with carboxylic acid-terminated alkanethiol surfaces using EDC/sulfo-NHS chemistry, and kinetic binding experiments were performed using kinetic injections of various concentrations of FnIII9'10 variant analyte, with a 10 minute dissociation phase following each injection. Individual antibodies were characterized for their ability to discriminate between two model Fn fragments by an ELISA assay (FIG. 3). Phage panning was performed using the Tomlinson I+J antibody libraries and selection to FnIII9*10 and FnIII9-4G-10 using established methods (de Wildt et al., 2000; Lee et al., 2007). Following three rounds of phage panning and selection, scFv antibodies with differential targeting selectivity towards the stabilized FnIII9*10 mutant versus FnIII9-4G-10 were further isolated using an ELISA assay. Soluble scFv were expressed in the absence of the phage by transfer of the vector into HB2151 *E. coli* cells and expression of soluble scFv induced by IPTG. Soluble scFvs were purified from the culture medium using Protein-A chromatography using an AKTA FPLC chromatography system.

By performing phage display panning and selection using scFv antibody libraries (see e.g., de Wildt et al., 2000; Lee et al., 2007) on the recombinant Fn fragments FnIII9*10 and FnIII9-4G-10, it was possible to isolate specific scFv with both high binding affinities and discrimination between the two model Fn fragments. Forty antibody clones were isolated and eight were carried forward for subsequent validation. Clone H5 displayed high selectivity towards the extended (FnIII9-4G-10), but not the native, stabilized (FnIII9*10) conformation. The characteristics of these scFvs are summarized in Table 4.

TABLE 4

Characteristics of scFv Clones

| Library | scFv | (4G/9*10) Ratio Preference | scFv | (4G/9*10) Ratio Preference |
|---|---|---|---|---|
| Tomlinson I | B1 | 2.818306 | G2 | 2.547049 |
| Tomlinson I | C2 | 2.256894 | F4 | 1.577504 |
| Tomlinson I | B2 | 1.328435 | G8 | 5.009584 |
| dAb | A4 | 0.485305 | D7 | 5.234991 |
| dAb | B4 | 0.452006 | E8 | 0.474262 |
| dAb | D1 | 0.601751 | F7 | 2.776091 |
| dAb | A8 | 2.491379 | F8 | 1.901473 |
| dAb | C8 | 3.458188 | | |
| Tomlinson I - 4G | E3 | 3.17104 | G3 | 2.1611 |
| Tomlinson I - 4G | C4 | 2.06550 | H5 | 2.0163 |
| Tomlinson I - 4G | G1 | 0.514737 | D2 | 1.8265 |
| Tomlinson I - 4G | F1 | 2.7782 | | |
| Tomlinson I - 9*10 | D2 | 0.1197 | A10 | 0.4958 |
| Tomlinson I - 9*10 | E4 | 0.1923 | G7 | 0.4997 |
| Tomlinson I - 9*10 | H5 | 0.2454 | H5 | 0.4453 |
| Tomlinson I - 9*10 | F7 | 3.1062 | H9 | 1.4553 |
| Tomlinson I - 9*10 | G2 | 0.4988 | A5 | 2.0489 |
| Tomlinson I - 9*10 | H5 | 2.6235 | C5 | 2.1898 |
| Tomlinson I - 9*10 | E2 | 0.582 | | |
| dAb - 4G | B5 | 1.8663 | F4 | 1.7859 |
| Tomlinson I - 4G | E3 | 3.1919 | G1 | 0.5147 |
| Tomlinson I - 4G | C4 | 2.0655 | | |

Example 2

Integrin Immunostaining on Fn Fragments

Human foreskin fibroblasts (ATCC, Manassas, Virginia, United States of America) were cultured on glass coverslips coated with 20 μg/ml of full-length Fn or 4 μM Fn fragment (FnIII9*10 or FnIII9-4G10). Cells were seeded at 5,000 cells/cm² in a 24 well plate, and cultured in serum-free medium. After 30 minutes of adhesion, cells were fixed in 50%/50% (v/v) mixture of ice-cold acetone-methanol, blocked with normal goat serum, and stained with antibodies against α5 integrin (MAB1928; Millipore, Billerica, Massachusetts, United States of America) or αv integrin (AB16821; Abcam, Cambridge, United Kingdom). Secondary antibodies ALEXAFLUOR® 488 goat anti-rabbit and ALEXAFLUOR® 546 goat anti-mouse (ThermoFisher Scientific, Waltham, Massachusetts, United States of America) were visualized using spinning disk confocal microscopy (PerkinElmer, Waltham, Massachusetts, United States of America). Ratiometric images were generated using an in-house MATLAB algorithm. Images were thresholded using Otsu's method, and masked based on where both α5 and αv signals passed the threshold. Fluorescence intensity of α5 staining was then divided by staining intensity of αv.

Example 3

Integrin-Blocking Cell Adhesion Assays

Antibodies were assessed for the functional ability to block cell attachment to Fn, and its effect on cell adhesion strength (Gallant et al., 2005). Fn was adsorbed to wells of a 95-well tissue culture plate at 10 µg/mL, and surface was blocked by heat denatured BSA for 1 hour at room temperature. Cells (human foreskin fibroblasts, CHO.B2-αvβ3, K562) were seeded at 5000 cells/well at allowed to attach for 30 minutes at 37° C. Plates were gently washed twice with PBS, fixed in 5% glutaraldehyde, and stained with 0.1% (w/v) crystal violet, and attached cells were quantified on plate reader by reading absorbance at 570 nm. Percent attachment was determined by interpolation from a standard curve, and statistics were performed with one-way ANOVA, with Tukey's post-test.

Example 4

Cell Adhesion Assays on Strained Cell-Derived ECMs

Figure 4A:
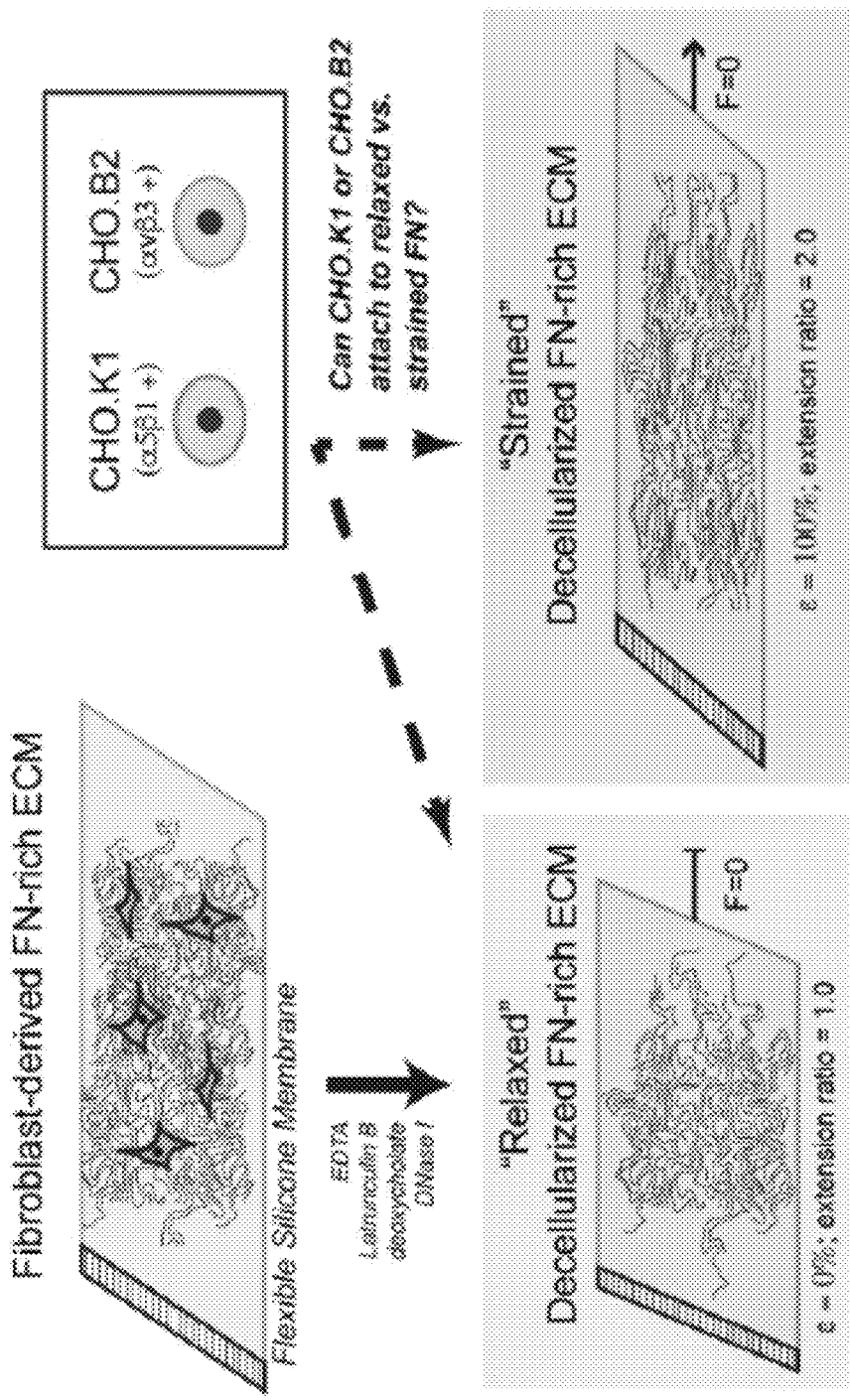
FIGS. 4A and 4B is a schematic of cell attachment experiments designed to demonstrate the impact of strain of a decellularized Fn-rich matrix on integrin binding and a a bar graph showing quantitation of cell adhesion on strained (red bars) and relaxed (blue bars) Fn-rich ECM demonstrating that strain of the ECM significantly impacted cell binding via α5β1, but not αVβ3, respectively. Error bars reflect SD, *p<0.05, N=6, ANOVA with Tukey's post-test.
Figure 4B:
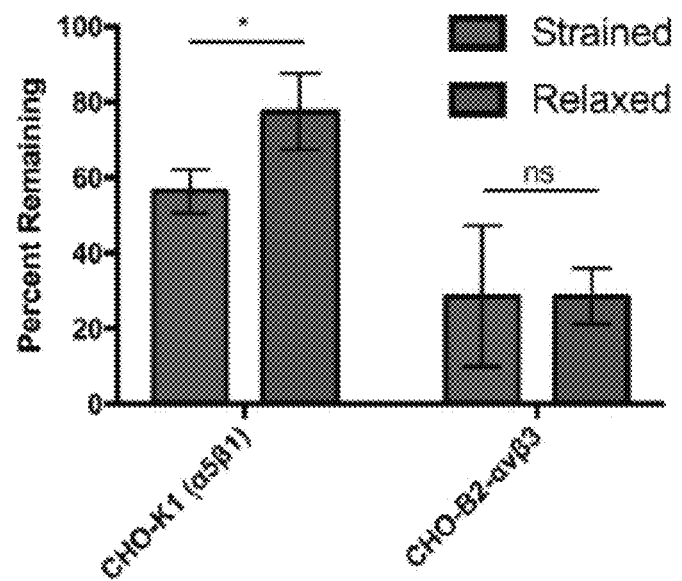
Figure 5A:
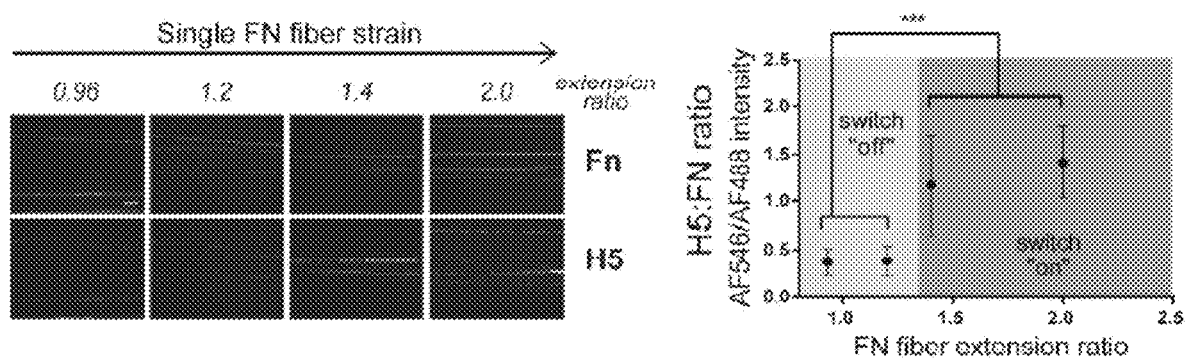
Figure 6C:
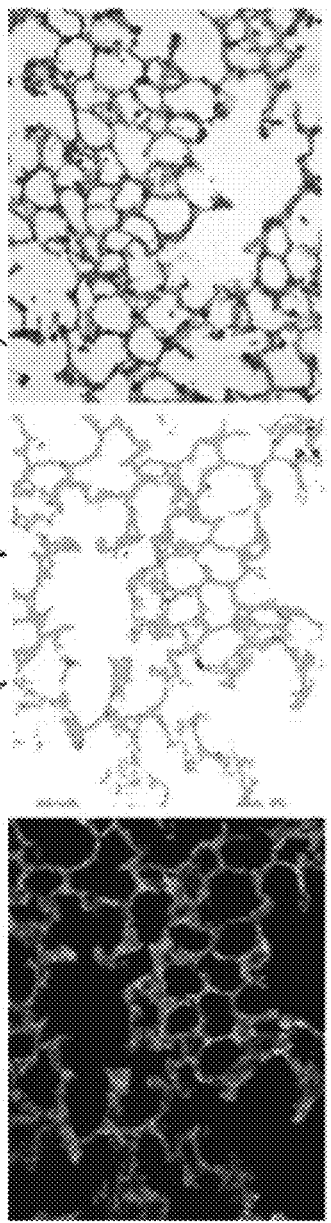
Figure 6D:
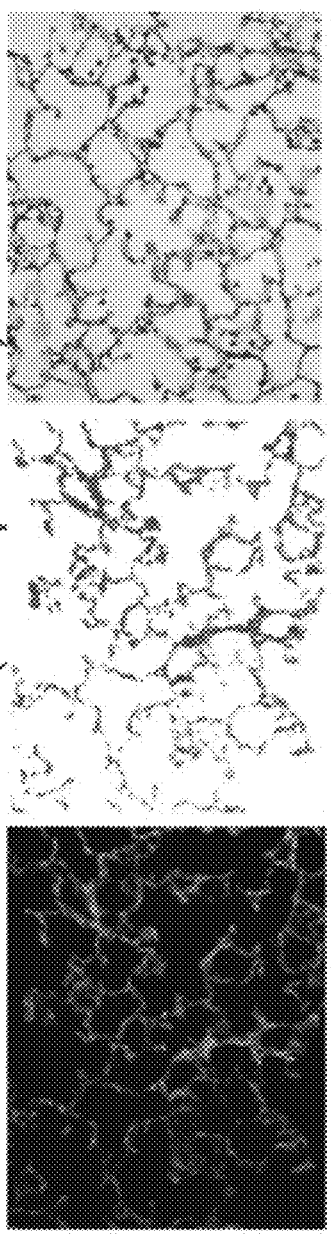
Figure 7:
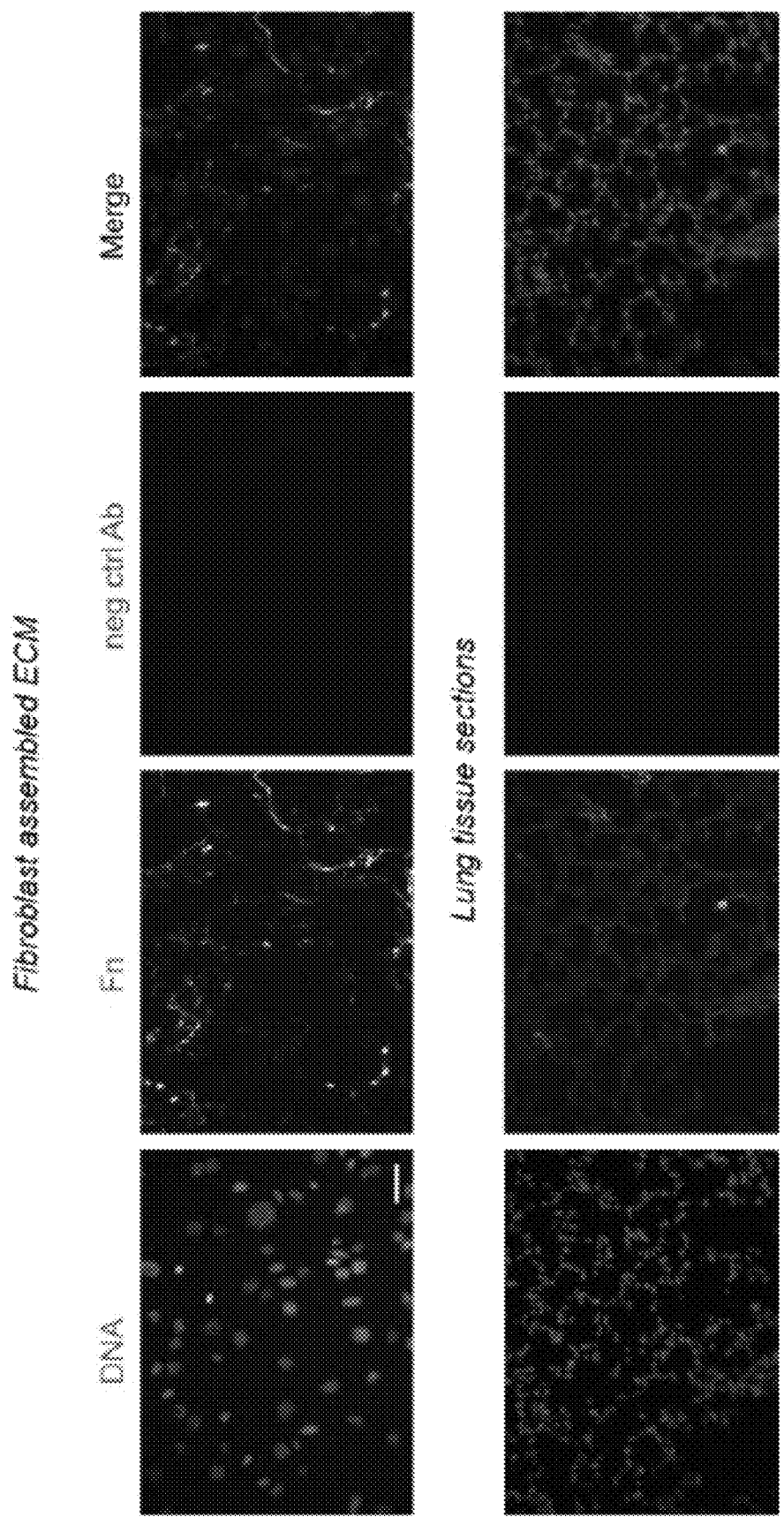
FIG. 7 is a series of fluorescence micrographs showing minimal staining of a negative control scFv antibody on fibroblast assembled ECMs and native ECMs. A negative control antibody was produced from a random clone from the parental Tomlinson I library, and staining experiments were performed on fibroblast assembled ECM (top) and on frozen mouse lung tissue sections (bottom). Scale bar is 50 μm.

Cell adhesion assays were additionally performed on decellularized Fn-rich ECMs formed on elastic PDMS membranes, which enable artificial straining or relaxing. Cells exclusively expressing α5β1 integrin (Schornberg et al., 2009) adhered to a lesser extent on strained Fn ECMs compared to relaxed, whereas cells exclusively expressing αvβ3 did not exhibit differential adhesion (see FIGS. 4A and 4B). The overall enhanced adhesion of cells expressing α5β1 was likely due to binding the PHSRN sequence (SEQ ID NO: 7), which enhanced cell adhesion over binding of RGD alone (Aota et al., 1994) Furthermore, the decreased adhesion of cells exclusively expressing αvβ3 could have been due to the transfection efficiency of the ITGAV vector into CHO B2 cells, which do not naturally express α5 or αv. By contrast, the CHO K1 cells endogenously express hamster α5β1 integrin (Schornberg et al., 2009). Taken together, these results supported the hypothesis of a force-sensitive "integrin switch" in Fn fibers, yet fell short of demonstrating a specific conformational change in the integrin binding domain.

Cell-derived matrices were assembled by human foreskin fibroblasts on polydimethylsiloxane (PDMS) membranes (Specialty Manufacturing Inc., Saginaw, Michigan, United States of America). Briefly, PDMS was treated with 0.1 N NaOH, followed by surface modification to immobilize Fn using (3-aminopropyl)triethoxy silane and glutaraldehyde as a crosslinker, using established methods (see Kuddannaya et al., 2013). Fibroblasts were seeded at 10,000 cells/cm$^2$ and allowed to assemble an ECM on the PDMS membranes for 7 days in culture. After 7 days, fibroblasts were chemically lysed and removed from the ECM using Latrunculin B (Sigma, St. Louis, Missouri, United States of America) to depolymerize actin, ethylenediamenetetraacetic acid (EDTA) to assist in integrin detachment, and sodium deoxycholate (DOC; Sigma, St. Louis, Missouri, United States of America) to lyse cell membranes. Nuclear DNA was digested with DNase I (Amresco, Solon, Ohio, United States of America). The remaining cell-derived ECM was either left relaxed or strained to an extension ratio of 2.0. Cells exclusively expressing αvβ3 (CHO.B2-αvβ3) or α5β1 (CHO.K1; Schornberg et al., 2009) were seeded at 10,000 cells/cm2 and allowed to attach for 15 minutes. After, unbound cells were gently washed off with PBS, the cell-derived ECMs fixed in 4% paraformaldehyde for 10 minutes, and the nuclei of remaining cells were stained with Hoechst 33342 (Life Technologies, Carlsbad, California, United States of America). Imaging of remaining cells was performed with a 20× objective on a spinning disk confocal microscope (PerkinElmer, Waltham, Massachusetts, United States of America). Percent remaining was calculated from interpolation from a standard curve, and statistics were performed with one-way ANOVA, with Tukey's post-test.

Validation of H5's recognition to FnIII9 and its selective inhibition of αvβ3 binding to Fn-adsorbed surfaces led to the use the H5 clone to test the hypothesis that Fn's integrin binding domain displays a force-induced conformational change (i.e., extension) when Fn fibers are mechanically strained. Manually deposited Fn fibers on micropatterned and stretched PDMS membranes displayed unfolding of Fn's type III repeats, demonstrated by the exposure of cryptic cysteines (see Smith et al., 2007; Little et al., 2008; Cao et al., 2012). Using this system, the binding of H5 to Fn fibers under increasing strain was found to display switch-like behavior, with H5 signal increasing significantly at an extension ratio of ~1.4-1.5, and plateauing at additional strain (see FIG. 5A). This discrete signature suggested an abrupt transition from a native folded to extended conformation upon the application of tensile force.

Similarly, on decellularized Fn-rich ECMs assembled on elastic PDMS membranes (FIG. 5B), H5 was able to both globally discriminate strained from relaxed Fn ECMs and locally discriminate between fibers in both a relaxed and strained ECM. H5 staining intensity of Fn-rich ECM also correlated strongly with the contractile state of resident fibroblasts, as induced by the addition of contractility agonists (TGF-β) or inhibitors (blebbistatin), suggesting that cell-generated forces are sufficient to activate the integrin switch (FIG. 5C).

H5 was then employed to probe Fn integrin binding domain conformations within native tissues. Stained tissues from two model systems were used: a mouse model of pulmonary fibrosis (Izbicki et al., 2002; Lawson et al., 2005).

The results are presented in FIGS. 4A-4D. The early repair (FIG. 6B) and fibrotic (FIG. 6C) time points showed areas of higher H5:Fn ratio, indicating the unfolding of Fn's integrin binding domain, perhaps indicative of active fibrosis. By resolution (FIG. 6D), the H5:Fn ratiometric image resembled that of the saline control (FIG. 6A).

Using frozen tissue sections from saline control and bleomycin-treated fibrotic mouse lungs, staining of H5, but not a negative control scFv, localized to fibrillar Fn (assessed using a polyclonal anti-Fn antibody) within the ECM. FIG. 7 provides a series of fluorescence micrographs showing minimal staining of a negative control scFv antibody on fibroblast assembled ECMs and native ECMs. A negative control antibody was produced from a random clone from the parental Tomlinson I library, and staining experiments were performed on fibroblast assembled ECM (top) and on frozen mouse lung tissue sections (bottom). Ratiometric image analysis revealed that the H5 staining patterns within these lung samples were spatially distinct, suggesting distinct conformational states of Fn within the matrix. Notably, the fibrotic time points (2-8 weeks) showed areas of high H5:Fn ratio, correlating with the severity of fibrosis observed in the corresponding H&E staining. By week 10, at which point the fibrosis was resolved, the H5:Fn ratio resembled that of the saline control. H5 was also used to probe the Fn-rich ECM during postnatal retinal vascularization. The retinas of newborn mice are avascular but become vascularized in a reproducible manner over the first 10 days after birth (Pitulescu et al., 2010). During angiogenesis, migration of endothelial tip-cells is guided by fibronectin fibers deposited by the astrocytic network (Jiang et al., 1994).

Figure 8A:
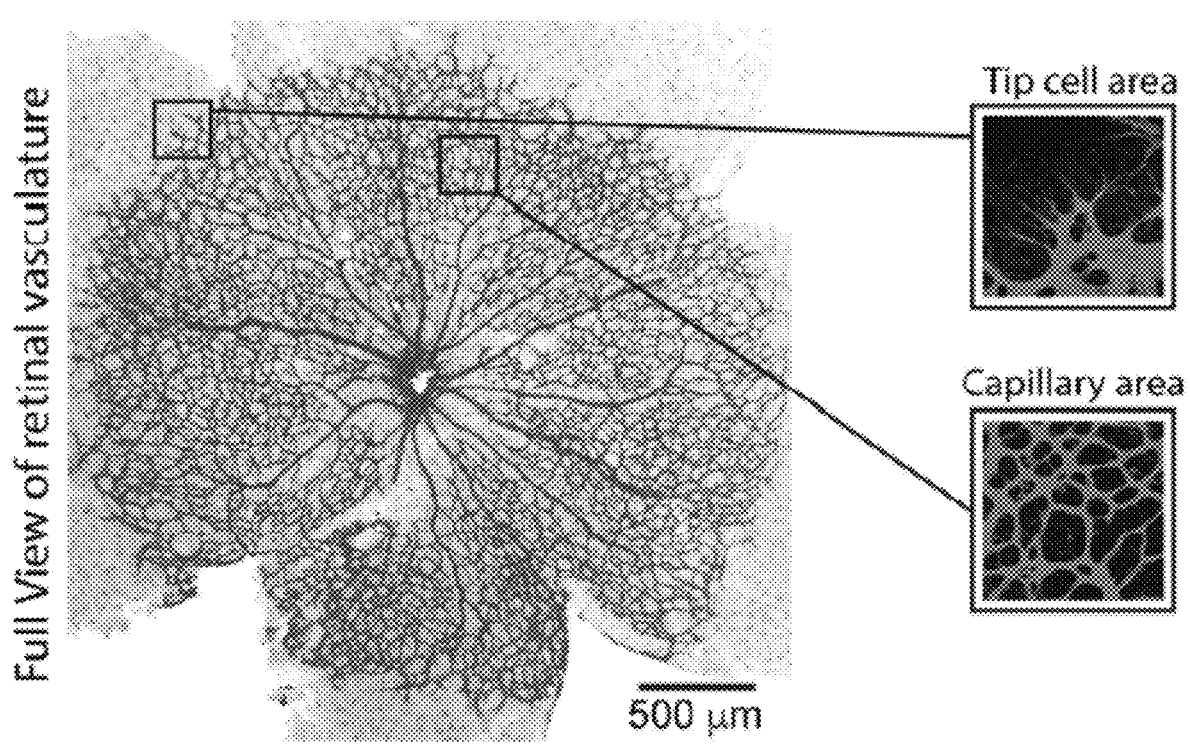
FIGS. 8A-8C depict the results of experiments showing that Fn's integrin mechano-switch was activated at tip cells during retinal angiogenesis.
Figure 8B:
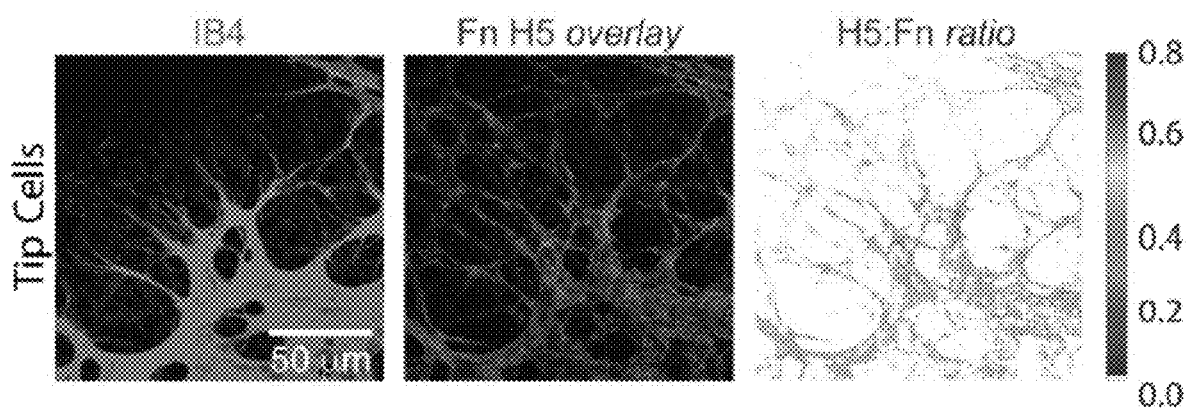
Figure 8C:
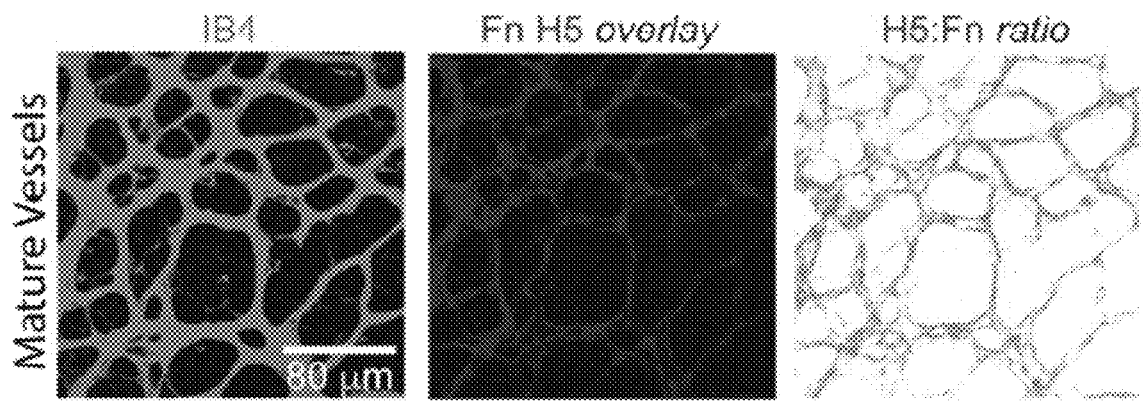

The results are presented in FIGS. 8A-8C, which show that Fn's integrin mechano-switch was activated at tip cells during retinal angiogenesis. FIG. 8A is a photograph of whole mount immunostaining for retinal endothelial cells during post-natal retinal angiogenesis with Tip Cell area and Capillary area (i.e. mature vessels) identified (scale bar=500 µm). FIG. 8B is a series of photographs of the tip cell region (scale bar=50 µm) and FIG. 8C is a series of photographs of mature vessels (scale bar=80 µm) that were immunostained with isolectin B4 (IB4, green) and H5 (red) and anti-Fn (blue) at post-natal day 6. Tip cells and blood vessels were visualized using isolectin B4. H5:Fn ratiometric images were generated for each region. The Tip Cell area (FIG. 8B) showed regions of high H5:Fn ratio, suggestive of endothelial tip cell force generation during angiogenesis. The mature vessel area (FIG. 8C), where forces were predicted to be low, displayed a low H5:Fn ratio.

Thus, the H5:Fn ratio was observed to be increased at the filopodia of tip cells, suggesting that cell-generated forces during vascular expansion is sufficient to alter the conformation of the integrin-binding domain of surrounding Fn fibers. In contrast, H5 showed minimal staining in regions of mature vessels.

These combined results both demonstrated the in vivo existence and activation of the long-theorized Fn conformational switch within the integrin binding domain and suggested its influence in skewing integrin specificity in both developmental processes, as well as in pathological tissue fibrosis. H5 thus represents an attractive approach to detecting and targeting key developmental and disease processes.

Example 5

Antibody Characterization by ELISA and SPR

Domain mapping of scFv antibodies was performed using a competitive ELISA assay analyzing the binding of H5 to immobilized FnIII9-4G-10 in the presence of soluble Fn fragments, including either the 9th (FnIII6-9) or 10th (FnIII10-14) type III repeats. In another ELISA experiment, 96 well plates were coated with purified proteins at the specified concentrations diluted in 1×PBS overnight at 4° C. Washes with PBST (0.1% TWEEN®-20 in PBS) removed unbound protein and then well plates were blocked with MPBS (2% wt/vol nonfat dry milk in PBS) for 30 minutes at room temperature on an orbital shaker. Bound proteins were then detected using a primary antibody. One plate was coated with the phage isolated H5 antibody (100 ng/mL), which is known to contain a myc tag, and a control plate was incubated with the primary antibody HFN 7.1 (1:2000, Thermo Fischer, MA5-12314), a monoclonal mouse antibody to the integrin-binding domain of Fn. The plates were then coated with an anti-myc biotin (1:2000, Sigma Aldrich, B7554) or anti-mouse biotin (1:2000, Abcam, ab97044) respectively. These steps were followed by HRP conjugated extravidin (1:1000, Sigma Aldrich, E2886). One-step Ultra TMB (3,3',5,5'-tetramethylbenzidine) ELISA substrate was used to complete the assay (Thermo Fischer, 34028). Absorbance readings were read at 450 nm on a BioTek Synergy H4 microplate reader and blank wells were subtracted so that relative protein concentration could be determined.

Figure 9A:
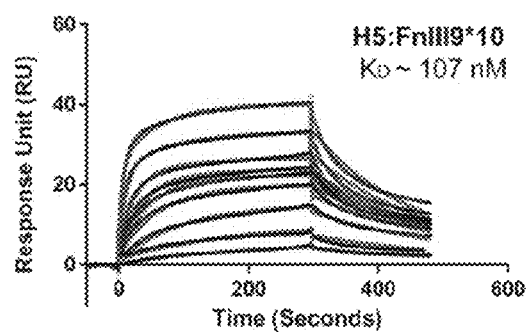
Figure 9B:
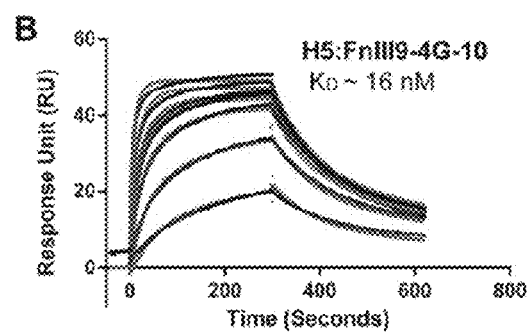
Figure 9C:
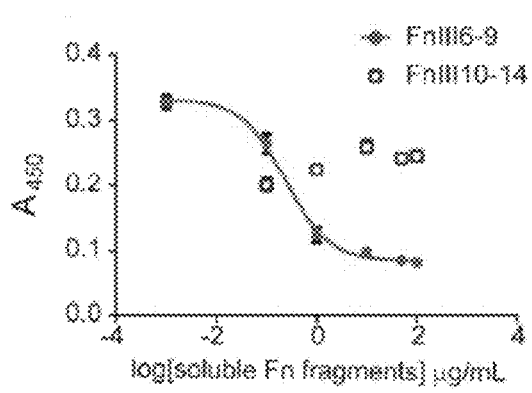
Figure 9D:
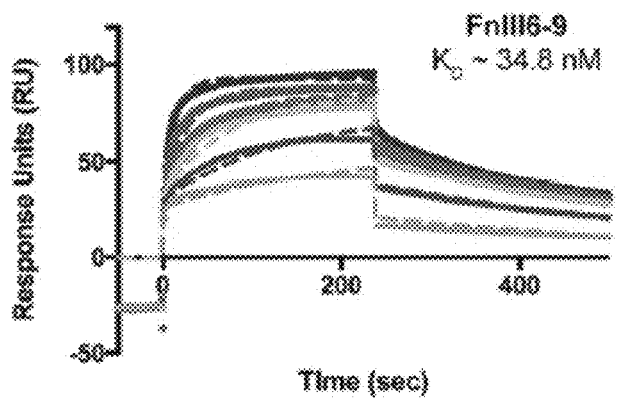
Figure 9E:
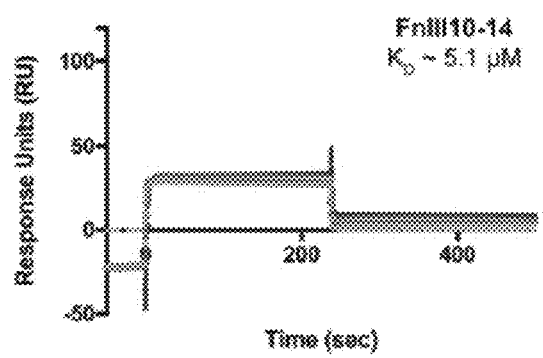

H5 binding kinetics were evaluated using SPR (see FIGS. 9A and 9B). Equilibrium dissociation constants ($K_D$) were determined to be 107 nM for H5 binding to FnIII9*10 and 16 nM for binding to FnIII9-4G-10. Selectivity of H5 binding to the FnIII9-4G-10 fragment was thus approximately an order of magnitude greater compared to FnIII9-10. Competitive ELISAs of H5 binding to FnIII9-4G-10 in the presence of increasing concentrations of soluble Fn fragments displaying only the 9th (FnIII6-9) or 10th (FnIII10-14) type III repeats demonstrated that increasing concentrations of FnIII6-9 blocked binding of H5 to Fn9-4G-10, which was not observed with increasing concentrations of FnIII10-14 (see FIG. 9C). Additionally, SPR analysis of H5 binding to these fragments revealed that the equilibrium dissociation constant ($K_D$) for H5 binding to FnIII6-9 was 34.8 nM, a higher affinity interaction than H5 binding to FnIII10-14 (5.1 µM; see FIGS. 9D and 9E). Together, these data indicated that H5's epitope was located within Fn's 9th type III repeat.

Example 6

Antibody Characterization by Western Blot

Purified, denatured/reduced proteins and PRECISION PLUS PROTEIN™ All Blue Prestained Protein Standard (#1610373; Bio-Rad Laboratories, Inc., Hercules, California, United States of America) were separated with a 6% SDS gel through SDS-PAGE and transferred to a nitrocellulose membrane where the blot was then cut to allow for separate staining. The western blots were then blocked with MTBS (5% wt/vol nonfat dry milk in 1×TBS) at room temperature for one hour then incubated with H5 or HFN 7.1 (1:6000) overnight at 4° C. on a 3D rocker. The H5 blot was then incubated with an anti-myc mouse monoclonal antibody (1:6000, Thermo Fischer, R950-25). Both blots were then incubated with a LI-COR goat anti-mouse IR dye 800CW (1:15000, LI-COR, Inc., 926-32210). Imaging of the blots was completed with a LI-COR scanner.

Figure 9F:
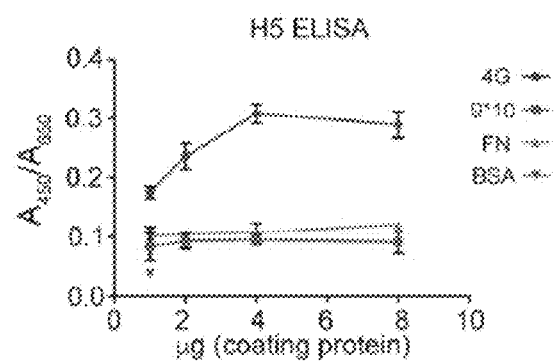
Figure 9G:
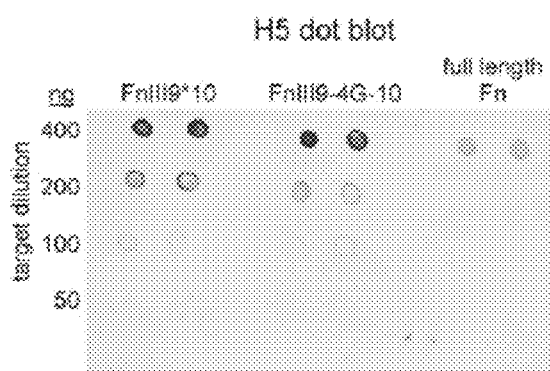
Figure 9H:
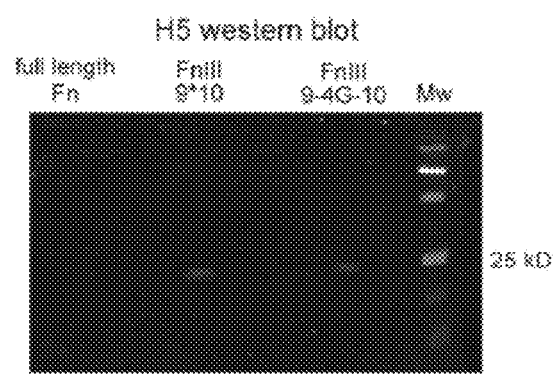
Figures 10A, 10B:
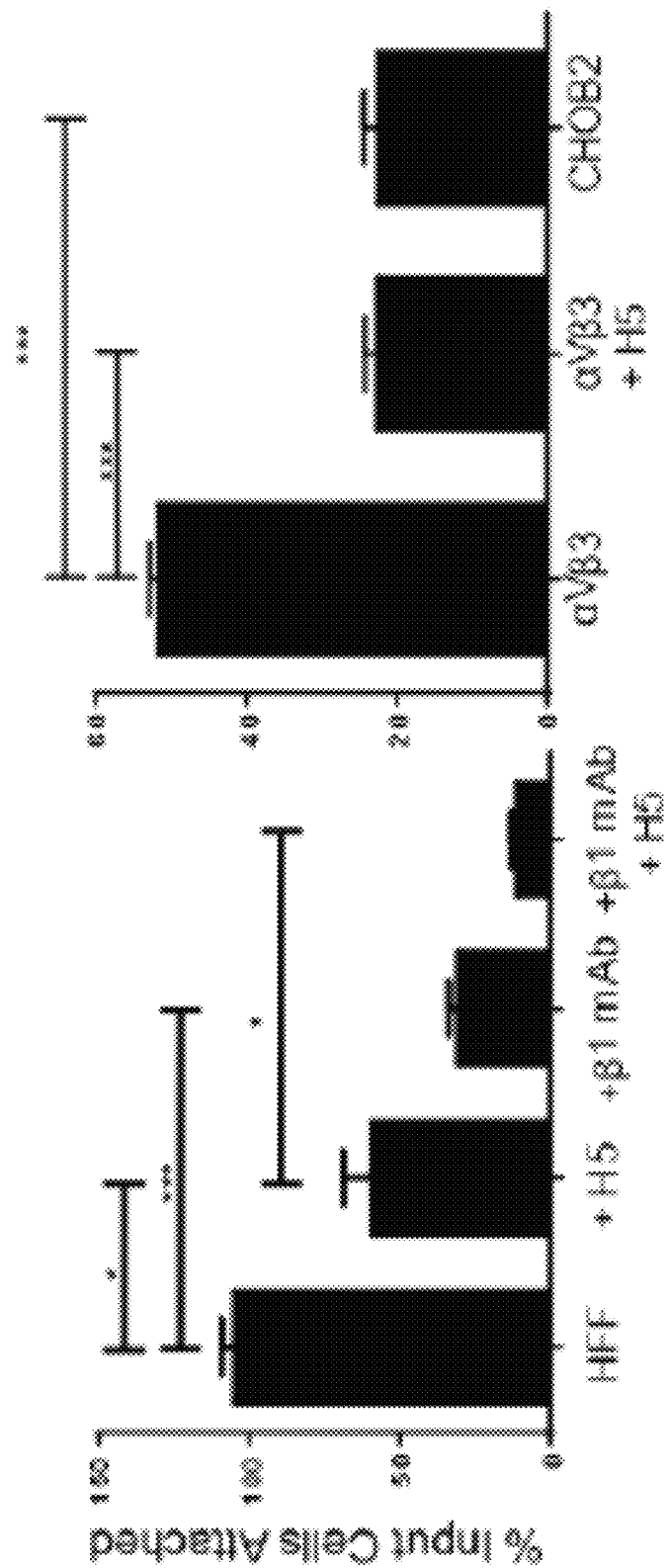
FIGS. 10A-10C are a series of bar graphs summarizing the results of experiments that showed that the H5 antibody selectively blocked integrin αVβ3-Fn interactions.
Figure 10C:
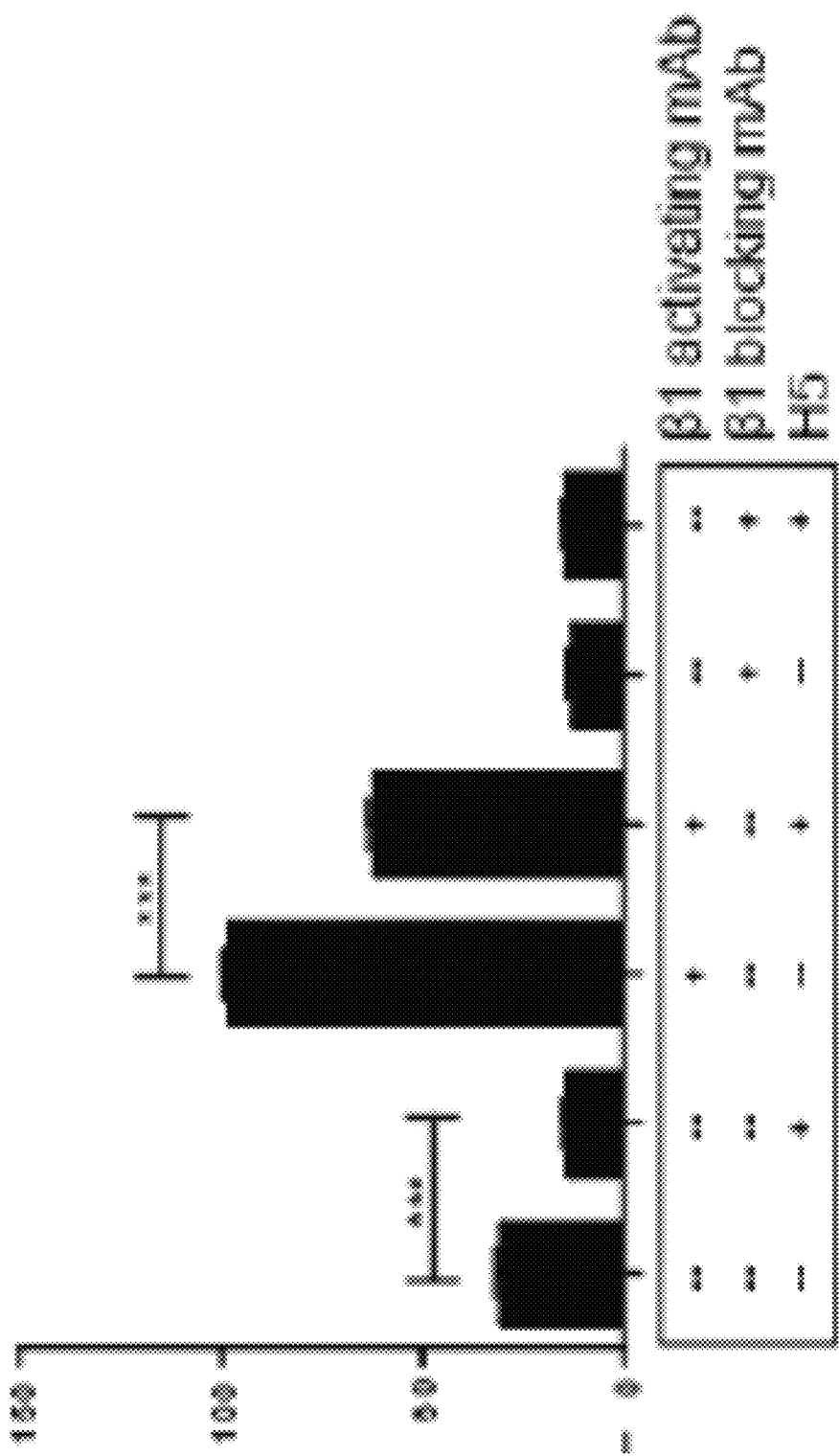

Binding characteristics of H5 to Fn and the Fn fragments were then evaluated by Western blot analysis in parallel with a commercially-available control antibody clone (HFN7.1; Novus Biologicals, LLC, Centennial, Coloroado, United States of America) against Fn's integrin binding domain (see FIGS. 9F-9K). FIG. 9F is a graph showing the results of ELISA of H5 binding to full-length Fn and Fn fragments. H5 bound increasingly to increasing amounts of surface adsorbed FnIII9-4G-10 to a significantly greater degree than FnIII9*10 or full length Fn at all concentrations (p<0.0001; Two-way ANOVA with Tukey's post-test, N=3). FIGS. 9G and 9H are a Nitrocellulose dot blot (FIG. 9G) and Western blot (FIG. 9H), respectively, of H5 binding to full-length Fn and Fn fragments. Under these denaturing conditions, H5 bound FnIII9-4G-10 and FnIII9*10 to a similar degree. FIGS. 9I-9K are a bar graph of the results of ELISA (FIG. 9I), dot blot (FIG. 9J), and Western blot (FIG. 9K) of HFN7.1, a commercially-available antibody targeting FnIII9-10 (Novus Biologicals, LLC, Centennial, Colorado, United States of America). In the ELISA, HFN7.1 only bound FnIII9-4G-10 to a significantly greater degree than FnIII9*10 at 1 M ($p<0.05$) and was not significant at higher concentrations (Two-way ANOVA with Tukey's post-test, N=3). HFN7.1 did not show preferential affinity for FnIII9*10 or FnIII9-4G-10 in the dot blot or Western blot.

The increased affinity of H5 to FnIII9-4G-10 versus FnIII9*10 was observed in ELISA, but not in dot blot or traditional denaturing Western blots, suggesting that the epitope bound by H5 was likely a linear peptide sequence and not a more complex 3D structure. It was hypothesized that if H5 bound to the open (or "off") state of the switch that it should selectively inhibit αvβ3-Fn interactions, since the antibody only weakly recognizes the closed/"on" α5β1-binding conformation. Standard cell attachment assays to Fn-adsorbed substrates, which present multiple conformations of Fn due to surface-mediated unfolding, confirmed the H5 clone selectively inhibited Fn-integrin αvβ3, but not α5β1, interactions with Fn.

The results are presented in FIGS. 10A-10C. FIG. 10A shows inhibition of attachment of human foreskin fibroblasts (HFF) to full length Fn. FIG. 10B shows inhibition of attachment of CHOB2 and CHOB2-αVβ3 cells to full length Fn. FIG. 10C shows inhibition of attachment of integrin α5β1 expressing K562 cells to full length Fn.

Example 7

Antibody Characterization by Dot Blot

Purified proteins were spotted in duplicate (5 μL each dot) at indicated concentrations onto a nitrocellulose membrane and given time to dry. The dot blots were then blocked with MTBS (5% wt/vol nonfat dry milk in 1×TBS) at room temperature for one hour then incubated with H5 or HFN 7.1 (1:6000) overnight at 4° C. on a 3D rocker. The H5 dot blot was then incubated with an anti-myc mouse monoclonal antibody (1:6000, Thermo Fischer, R950-25). Both dot blots were then incubated with a LI-COR goat anti-mouse IR dye 800CW (1:15000, LI-COR, 926-32210). Imaging of the dot blots was completed with a LI-COR scanner.

Example 8

Mouse Bleomycin Model of Pulmonary Fibrosis

All animal experiments were done in accordance with IACUC guidelines at GT following an approved protocol. Mice (C57/BL6, female, 6-8 weeks age) were obtained from Jackson's Labs and allowed to recover anesthetized using a ketamine/xylazine/acepromazine cocktail, and injected with Bleomycin sulfate (Enzo Life Science, Farmingdale, New York, United States of America) at a dose of 3.2 U/kg through intratracheal injections. Injection volumes were 50 μL of solution, with additional 10 μL of air bolus. Immediately after injection, mice were placed on heating pads and allowed to recover from anesthesia before placed back into housing.

Example 9

Imaging of Fn Using H5 on Fn Fibers In Vitro

Fn fibers were deposited on polydimethylsiloxane (PDMS) substrates as described previously (Cao et al., 2012) strained to indicated amounts, and purified H5 antibody (50 μg/mL) was incubated on Fn fibers for 1 hour, stained with anti-Myc antibody (Life Technologies, Grand Island, New York, United States of America), anti-Fn (Millipore, Billerica, Massachusetts, United States of America) and visualized with ALEXAFLUOR® 488 and ALEXAFLUOR® 546 secondary antibodies (Life Technologies, Grand Island, New York, United States of America).

Example 10

Imaging of Fn Using H5 on Cell-Assembled ECM In Vitro in Response to Cell Contraction Coverslips (10 mm diameter) were sterilized in 70% ethanol and placed into wells of a 24-well plate and coated with Fn (3 μg/mL) overnight at 4° C. Prior to cell seeding, coverslip were washed 3× with PBS and mouse primary lung fibroblasts were seeded at 10,000 cells/well. Cell were allowed to attach for 30 minutes at 37° C. in the incubator. After 30 minutes, medium was then aspirated and replaced with medium containing 1 μg/mL ALEXAFLUOR® 488 (ThermoFisher Scientific, Waltham, Massachusetts, United States of America) labeled Fn. Cells were then cultured for an additional 48 hours, at 37° C., 5% $CO_2$ in the incubator, during which time the fluorescent Fn was incorporated into the assembled ECM. TGF-β (10 ng/mL) was added 16 hours before fixing cells in appropriate wells, and blebbistatin (20 μM) was added 30 min prior to fixation where appropriate. Cells were washed 3 times with PBS and fixed in 4% formaldehyde for 20 minutes. Fixed cells were blocked for non-specific binding with 3% BSA in PBS overnight at 4° C. and stained with H5 antibody (50 μg/mL), anti-Myc antibodies to detect the myc tag of H5 (Fisher Scientific, Hampton, New Hampshire, United States of America), and visualized with confocal microscopy with ALEXAFLUOR® 546 secondary antibody (ThermoFisher Scientific, Waltham, Massachusetts, USA). Ratiometric image analysis of H5 staining with respect to total Fn was performed using a custom program written in MATLAB (Natick, Massachusetts, United States of America). Briefly, images were thresholded using Otsu's method, and masked based on where both Fn and H5 signals passed the threshold. Fluorescence intensity of H5 staining was then divided by staining intensity of Fn. Image quantitation was performed on the processed ratiometric image by generating a histogram of ratiometric (H5:Fn) pixel values.

Example 11

Imaging of Fn Using H5 on Strained ECMs Assembled on PDMS

Cell-derived ECMs were assembled by human foreskin fibroblasts on polydimethylsiloxane (PDMS) membranes as described above. 48 hours prior to decellularization, media was aspirated and replaced with medium containing 1 μg/mL ALEXAFLUOR® 555 (ThermoFisher Scientific, Waltham, Massachusetts, United States of America) labeled Fn, which was then assembled by cells into the ECM. The remaining cell-derived ECMs were left relaxed or strained to an extension ratio of 2.0. ECMs were fixed in 4% paraformaldehyde for 10 minutes, blocked with 3% BSA for 1 hour at room temperature, and stained with H5 (10 μg/mL) as described above. ECMs were imaged with confocal microscopy for ALEXAFLUOR® 555-labeled Fn and the myc tag through an ALEXAFLUOR® 647 secondary antibody. N=6 ECMs imaged for relaxed and strained conditions each. Ratiometric analysis for H5:Fn was performed using the MATLAB script described above, and the mean ratio values of each condition were compared using the Wilcoxon Sum Rank Test.

Example 12

Imaging of Fn Using H5 on Ex Vivo Lung Tissue Samples

Mice were euthanized, and the lungs were collected and fixed with 4% paraformaldehyde. Fixed lungs were placed into 20% sucrose overnight at 4° C., embedded in O.C.T. compound (Electron Microscopy Sciences, Hatfield, Pennsylvania, United States of America) and frozen in 1-methylbutane in liquid $N_2$. Frozen sections (10 µm thickness) were prepared on a Cryostar NX70 cryostat (Thermo Scientific, Pittsburgh, Pennsylvania, United States of America) and transferred to Plus-glass slides. Lung sections were blocked overnight at 4° C. with 3% BSA in PBS. All staining was performed by sandwiching the staining solution (150 µL per slide) between the slide and a parafilm surface. Slides were blocked for non-specific binding with 3% BSA in PBS overnight at 4° C. and stained with H5 antibody (10 µg/mL), anti-Fn and anti-Myc antibodies, and visualized with ALEXAFLUOR® 488 and 546 secondary antibodies.

Example 13

Imaging of Fn Using H5 on Postnatal Mouse Retina

Mouse eyes were removed from euthanized postnatal pups at postnatal day 6 (P6) and fixed in 4% paraformaldehyde for one hour in room temperature (RT) before dissection of the retina under a stereo microscope. Prior to whole mount staining, retinas were permeabilized in blocking buffer (PBS solution containing 0.1% Triton X-100 and 2% BSA) at 4° C. overnight. After three times 20-minute wash by Pblec buffer (1.0% Triton X-100, 0.1 mM $MgCl_2$, 0.1M $CaCl_2$, 0.01M $MnCl_2$ in PBS), retina was further incubated at 4° C. overnight with primary antibodies diluted in Pblec buffer. Retinas were washed five times for 20 minutes with washing buffer (blocking buffer in the ratio of 1:1 in PBS solution), positive staining was detected with fluorescent-conjugated secondary antibody diluted in blocking buffer for 2 hours in RT. Finally, the specimens were washed in washing buffer for 5×20 minutes and 2×5 minutes in PBS. Retinas were mounted with Fluoroshield with DAPI (Sigma) and the slide was kept in RT for at least one hour. Digital images were taken either by Leica TCS SP5 confocal microscope or Zeiss 710 confocal microscope. The following reagents were used for staining: Biotinylated isolectin B4 (IB4, Vector, 1:200), Fibronectin (Millipore, 1:150), ScFv antibodies: A4-546/H5-546 (Final concentration for staining: 10 µg/ml).

Example 14

Creation of H5 Clone Library

The library of H5 clones was created through mutagenesis by error prone PCR. Three mutagenesis reactions were performed using the Agilent GeneMorph II Random Mutagenesis Kit, which comprises Mutazyme II DNA polymerase, buffers, and dNTP mix, along with the appropriate primers to introduce mutations in the full length of the scFv antibody. Random mutagenesis by error prone PCR introduces mutations in DNA for protein characteristic modifications. Using the Agilent kit as per the manufacturer's instructions, the mutation rate can be adjusted by varying the amount of target DNA added and the number of amplification cycles. Since the aim was to create a library that was as diverse as possible, the recommendations for a high mutation rate was followed. The number of mutations per 1,000 base pairs was estimated to be between nine and 16, since 10 ng of target DNA was amplified for 33 cycles. A conservative estimate yields an error rate of about one percent per reaction, since the full length of H5 is 850 base pairs. To maximize the mutation rate, however, sequential error prone PCRs were performed. The product of the first round was used as the template for the second round, and the product of the second round was used as the template for the third round. Therefore, the first round of error prone PCR yielded about a one percent mutation rate, while the second round and third rounds of error prone PCR yielded about two and three percent mutation rates, respectively. After the final round of error prone PCR, digestion, ligation, and electroporation were conducted to prepare the clones for phage display. The cells were then infected with helper phage to allow for the cells to display the H5 library. Afterwards, 20 random colonies that were plated and grown were sent for sequencing to verify the diversity of the library. The library comprised over one million clones that could potentially possess stronger binding affinity to 4G than that of H5. These clones then proceeded to the next stage, comprising positive and negative selection.

Example 15

Phage Display Selection

During phage purification, a 5 mL conical tube with the full-length library split while in the centrifuge, which resulted in loss of the full-length library. Instead, a previously made library with variations in the heavy chain of the scFv antibody, produced through the same process of mutagenesis, was used. The heavy chain mutated library was inserted into TG1 cells by electroporation for use in phage display. As part of phage display, a series of negative and positive selection rounds were performed to narrow down the number of clones. The antibodies were negatively selected for through binding to 9*10 and were positively selected for through binding to 4G. In order to quantify the total number of clones obtained after the first round of selection, cells were plated in serial dilutions. Each colony, represented by one speck on a plate, theoretically represents one unique antibody clone. However, some colonies could have been duplicates or unviable antibodies due to the random nature of the error prone PCR process. After each round, the number of phage was estimated in order to confirm that titers were similar among selection rounds (FIG. 13). The calculation for number of phage per milliliter was provided by the original protocol for phage display as follows: Phage per mL OD260*100*22.14*$10^{10}$ (Lee et al., 2017). This calculation indicates the total number of phage, but does not necessarily indicate the number of unique sequences carried by the phage after each round of selection. The process assumes that after each round of selection, phage carrying favorable antibodies are enriched and occupy a greater percentage of the total quantity of phage. As shown in FIG. 13, an increase in phage titers in rounds three and four indicates that the enrichment process worked to increase the number of phage copies that carried antibodies with an affinity for 4G. Through this negative and positive selection process, the number of nonviable clones were eliminated while the number of favorable clones were enriched.

Example 16

ELISA Testing

Of the remaining clones, ELISA testing was performed in order to quantify and to identify which clones performed better than H5. Seven rounds of ELISA testing for single colonies were completed. For each round, an ELISA was performed to measure the binding of a plate containing 9*10 and a plate containing 4G. The first well (A1) of the plate contained H5, while the remaining 95 wells contained different colonies selected from the bacterial cell cultures grown after positive and negative selection. At the end of each ELISA round, a plate reader was used to measure the absorbance for each plate at two different wavelengths (450 and 650 nm). The absorbance values at 650 nm were subtracted from those at 450 nm to remove background noise. The adjusted values were then used to calculate absorbance ratios of the corresponding 4G and 9*10 plates. Absorbance ratios were calculated by dividing the absorbance value of 4G by the absorbance value of 9*10 (Absorbance Ratio=4G/9*10). Clones that produced higher absorbance ratios than the absorbance ratio of H5 indicated better binding to strained fibronectin. Rounds 5, 6, and 7 did not produce any viable clones. These three rounds were repeated twice with new reagents and chemicals. Unfortunately, no viable clones were identified through new ELISA tests, so the project continued with the clones from only the first four rounds.

After the seven rounds, 23 clones displayed greater ratios than the respective H5 ratio from each round. When analyzing absorbance ratios for the second round, it was found that many clones had higher 4G/9*10 ratios than the control, H5, did. It was proposed that additional background noise may have affected the absorbance values or that the control set a low standard for 4G/9*10 ratios. Thus, a higher 4G/9*10 threshold was established for selecting the best clones for that particular round.

The clones were then sequenced to determine duplicates and exact copies of H5. From the sequenced clones, five were found to be different from H5: R1H6, R1H8, R1F8, R2G3, and R4B8. Table 5 is a Table of Preference of best clones from ELISA testing for 4G. This table summarizes the ELISA data for the best clones that were found to have different amino acid sequences from H5. The ratio value indicates the preference for 4G over 9*10. The H5 control ratio is also listed for each round for comparison purposes. As shown, 4G/9*10 ratios for the clones were greater than those for their corresponding control ratios.

TABLE 5

Clone Preferences after ELISA Testing

| Name | 4G/9*10 Ratio |
|---|---|
| H5 in Round 1 | 1.208 |
| R1H6 | 1.625 |
| R1H8 | 1.415 |
| R1F8 | 1.328 |
| H5 in Round 2 | 1.023 |
| R2G3 | 2.531 |
| H5 in Round 4 | 1.058 |
| R4B8 | 1.488 |

However, R1H8 and R1F8 were found to have the same amino acid sequence. The notation was created by combining the round number and ELISA well positions. R1F8 contained one mutation close to CDR3, a complementarity-determining region found in the variable chain. R1H6 contained one mutation between CDR2 and CDR3. R2G3 contained two mutations; one between CDR1 and CDR2 and another between CDR2 and CDR3. R4B8 contained one mutation in CDR2. Regions in between these CDR sites have been found to be responsible for binding affinity; thus, variations in these sites are considered to be favorable (Foote & Winter, 1992; Koenig et al., 2017). The amino acid sequences for the four clones, along with indications of CDRs and mutations that deviate from the original H5 sequences, are diagrammed in FIG. 14. To summarize, through ELISA testing, four unique clones outperformed H5 in binding preference to 4G.

Discussion of Examples 14-16

Antibody Library Production and Initial Selection. The goal of this project was to develop a more effective antibody than H5 for binding to the disease-state model of Fn called 4G. First, an antibody library of over one million clones was created and negatively and positively selected to eliminate poor clones and enrich strong clones, respectively.

During negative and positive selection rounds, phage numbers remained relatively consistent throughout the four rounds. At the beginning of the first selection, the library included a combination of viable and nonviable clones as a result of the random mutations created through error prone PCR. Each selection process eliminated more nonviable antibodies, while keeping the number of phage particles the same. This selection process was conducted to enrich the phages that have favorable sequences. The third and fourth rounds saw an increase in phage titers, which suggested that the clones were enriched.

ELISA Testing. Seven ELISA tests were performed to quantify and to identify clones that bound better to the strained conformation of Fn than the current H5 antibody does. The first four rounds produced the expected absorbance values, but the remaining rounds yielded low absorbance values deemed unusable for analysis. When the fifth and sixth rounds produced abnormally low absorbances, new reagents, such as KM13 helper phage, secondary antibody, and TMB substrate solution were prepared and bought in case the original reagents were the cause of faulty ELISAs. Comparably low absorbance values for the H5 antibody (control) in well A1 for each plate furthered this hypothesis. Rounds 5 and 6 were repeated and round 7 was conducted with new reagents, but they each failed to produce meaningful results. Due to time constraints, selection proceeded with the antibody clones from the four successful ELISAs.

Isolation of Antibody from Phage. After completion of the multiple ELISA rounds, 23 clones with 4G/9*10 ratios better than those of H5 were sent for sequencing. The sequencing results showed that many of the clones code for duplicates of the current H5 antibody. Of the 23 clones, only four antibodies were chosen to continue to the next parts in the project. In order to perform further characterization experiments such as BLI and epitope mapping, the antibodies must be separated from the phage. The phage was necessary to carry the antibody clones through phage display and ELISA processes stably. A method called the Gibson Assembly can be employed as a way of assembling multiple fragments of DNA that replaces the need for restriction sites. A reaction mix that includes exonuclease, polymerase, and ligase is gathered along with the DNA fragments for the Gibson Assembly reaction (Gibson, 2011).

Characterization of the antibody clones can also be accomplished through bio-layer interferometry (BLI) and epitope mapping. BLI is a label-free technology that measures molecular interactions in real time for the purpose of detection, quantification, and kinetic analysis. Specifically, BLI measures interference patterns between waves of light. The instruments operate by directing white light down a fiber-optic biosensor towards two interfaces separated by an internal reference layer and a thin biocompatible layer, which resides on the surface of the tip. The reflection of this directed white light by the two layers result in constructive or destructive interference at various spectrum wavelengths. Then, a CCD array detector measures the interference pattern. Interference patterns in real time yield kinetic data of the molecular interactions, which can be used to eliminate H5 antibody clones that indicate weak molecular interactions with FnIII9-4G-10 (Tobias, 2014).

In addition to using surface plasmon resonance (SPR), which is commonly used to measure the strength and kinetics of binding, characterization of antibody clones can include epitope mapping. Epitope mapping characterizes the interaction between the strained conformation of fibronectin and the new antibody clone. It can give greater insight into the mechanisms of binding and reveal nuances of IPF disease progression from the viewpoint of fibronectin. Epitope mapping can be performed through site-directed mutagenesis, where mutations of specific amino acids of the Fn fragments would be introduced for assay testing. In testing, drops in affinity or losses of function of the mutated fragments will indicate specific amino acids' importance in the antibody-protein interaction (Benjamin & Perdue, 1996).

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Addgene (2017) Over-Agar Antibiotic Plating. Basic Molecular Biology Protocol available from the website of Addgene of Watertown, Massachusetts, United States of America.

Altschul et al. (1990a) Basic local alignment search tool. J Mol Biol 215:403-410.

Altschul et al. (1990b) Protein database searches for multiple alignments. Proc Natl Acad Sci USA 87:14:5509-5513.

Altschul et al. (1997) Gapped BLAST and PSI-BLAST: a new generation of protein database search programs. Nucleic Acids Res 25:3389-3402.

Arimori et al. (2017) Fv-clasp: An Artificially Designed Small Antibody Fragment with Improved Production Compatibility, Stability, and Crystallizability. Structure 25:1611-1622.

Aota et al. (1994) The Short Amino Acid Sequence Pro-His-Ser-Arg-Asn in Human Fibronectin Enhances Cell-Adhesive Function. J Biol Chem 269:24756-247561.

Barbas (1995) Synthetic human antibodies. Nature Medicine 1:837-839.

Bazan et al. (2012) Phage display—A powerful technique for immunotherapy. Hum Vaccines Immunother 8:1817-1828.

Benjamin & Perdue (1996) Site-Directed Mutagenesis in Epitope Mapping. Methods 9:508-515.

Bird et al. (1988) Single-chain antigen-binding proteins. Science 242:423-426.

Bodanszky & Bodanszky (1984) in *The Practice of Peptide Synthesis*, Springer-Verlag, New York, New York, United States of America.

Brennan et al. (1985) Preparation of bispecific antibodies by chemical recombination of monoclonal immunoglobulin G1 fragments. Science 229:81-83.

Brockmann (2012) Selection of Stable scFv Antibodies by Phage Display. in *Antibody Engineering: Methods and Protocols, Second Edition* (ed. Chames, P.) Humana Press, New York, New York, United States of America, pages 123-144.

Brown et al. (2011) Guiding Epithelial Cell Phenotypes with Engineered Integrin-Specific Recombinant Fibronectin Fragments. Tissue Eng, Part A 17:139-50.

Brown et al. (2015) Integrin alpha3beta1 Binding to Fibronectin Is Dependent on the Ninth Type III Repeat. J Biol Chem 290:25534-25547.

Burton & Barbas (1994) Human antibodies from combinatorial libraries. Adv Immunol 57:191-280.

Cadwell & Joyce (1992) Randomization of genes by PCR mutagenesis. PCR Methods Appl 2:28-33.

Cao et al. (2012) Phage-Based Molecular Probes that Discriminate Force-Induced Structural States of Fibronectin in vivo. Proc Natl Acad Sci USA 109:7251-7256.

Cao et al. (2017) Detection of an Integrin-Binding Mechanoswitch within Fibronectin during Tissue Formation and Fibrosis. ACS Nano 11:7110-7117.

Carisey et al. (2013) Vinculin Regulates the Recruitment and Release of Core Focal Adhesion Proteins in a Force-Dependent Manner. Curr Biol 23:271-281.

Carter et al. (1992a) High level *Escherichia coli* expression and production of a bivalent humanized antibody fragment. Bio/Technology 10:163-167.

Carter et al. (1992b) Humanization of an anti-p185HER2 antibody for human cancer therapy. Proc Natl Acad Sci USA 89:4285.

Chandler et al. (2011) Adipose Progenitor Cells Increase Fibronectin Matrix Strain and Unfolding in Breast Tumors. Phys Biol 8:015008.

Chen et al. (2013) Fusion Protein Linkers: Property, Design and Functionality. Adv Drug Deliv Rev 65:1357-1369.

Chothia & Lesk (1987) Canonical structures for the hypervariable regions of immunoglobulins. J Mol Biol 196:901-917.

Cole et al. (1985) in *Monoclonal Antibodies and Cancer Therapy*, Alan R. Liss, Inc., New York, New York, United States of America, pp. 77-96.

Cote et al. (1983) Generation of human monoclonal antibodies reactive with cellular antigens. Proc Natl Acad Sci USA 80:2026-2030.

Craig et al. (2001) Comparison of the Early Stages of Forced Unfolding for Fibronectin Type III Modules. Proc Natl Acad Sci USA 98:5590-5595.

Craig et al. (2004) Tuning the Mechanical Stability of Fibronectin Type III Modules Through Sequence Variations. Structure 2004, 12, 21-30.

Craig et al. (2008) Effect of Linker and Spacer on the Design of a Fibronectin-Mimetic Peptide Evaluated via Cell Studies and AFM Adhesion Forces. Langmuir 24:10282-10292.

Cuccuru et al. (2012) A simple, rapid and inexpensive technique to bind small peptides to polystyrene surfaces for immunoenzymatic assays. J Immunol Methods 382:216-219.

Datta et al. (2011) Novel therapeutic approaches for pulmonary fibrosis. Br J Pharmacol 163:141-172.

de Kruif et al. (1995) Selection and application of human single chain Fv antibody fragments from a semi-synthetic phage antibody display library with designed CDR3 regions. J Mol Biol 248:97-105.

de Wildt et al. (2000) Antibody Arrays for High-Throughput Screening of Antibody-Antigen Interactions. Nat Biotechnol 18:989-994.

Deutscher et al. (1990) *Guide to Protein Purification*, Harcourt Brace Jovanovich, San Diego, California, United States of America.

Devereux et al. (1984) A comprehensive set of sequence analysis programs for the VAX. Nucl Acids Res 12:387-395.

European Patent Application No. 17868682.0.

Foote & Winter (1992) Antibody framework residues affecting the conformation of the hypervariable loops. J Mol Biol 224:487-499.

Gallant et al. (2005) Cell Adhesion Strengthening: Contributions of Adhesive Area, Integrin Binding, and Focal Adhesion Assembly. Mol Biol Cell 16(9):4329-4340.

Garcia et al. (2002) Distinct Activation States of alpha5beta1 Integrin Show Differential Binding to RGD and Synergy Domains of Fibronectin. Biochemistry 41:9063-9069.

Gee et al. (2008) Fibronectin Unfolding Revisited: Modeling Cell Traction-Mediated Unfolding of the Tenth Type-III Repeat. PLoS One 3:e2373.

Genaro (1985) *Remington's Pharmaceutical Sciences*, Mack Publishing Co., Easton, Pennsylvania, United States of America.

Gibson (2011) Enzymatic Assembly of Overlapping DNA Fragments. Chapter Fifteen of Methods in Enzymology 498:349-361.

Gottesman (1996). Proteases and Their Targets in *Escherichia coli*. Annual Review of Genetics, 30(1):465-506.

Grashoff et al. (2010) Measuring Mechanical Tension Across Vinculin Reveals Regulation of Focal Adhesion Dynamics. Nature 466:263-266.

Green & Sambrook (2012) *Molecular Cloning: A Laboratory Manual, Fourth Edition*, Cold Spring Harbor Laboratory Press, Cold Spring Harbor, New York, United States of America.

Grodberg & Dunn (1988) OmpT encodes the *Escherichia coli* outer membrane protease that cleaves T7 RNA polymerase during purification. J Bacteriol 170:1245-1258.

Gross & Mienhofer (1981) *The Peptides, Vol.* 3, Academic Press, New York, New York, United States of America, pp. 3-88.

Gu et al. (1997) Construction and expression of mouse-human chimeric antibody SZ-51 specific for activated platelet P-selectin. Thromb Haemost 77(4):755-759.

Harlow & Lane (1988) *Antibodies, A Laboratory Manual*, Cold Spring Harbor Laboratory Publications, Cold Spring Harbor, New York, United States of America.

Henderson et al. (2013) Targeting of AlphaV Integrin Identifies a Core Molecular Pathway that Regulates Fibrosis in Several Organs. Nat Med 19:1617-1624.

Hubbard et al. (2016) Fibronectin Fiber Extension Decreases Cell Spreading and Migration. J Cell Physiol 231:1728-1736.

Huse et al. (1989) Generation of a large combinatorial library of the immunoglobulin repertoire in phage lambda. Science 246:1275-1281.

Huston et al. (1988) Protein engineering of antibody binding sites: recovery of specific activity in an anti-digoxin single-chain Fv analogue produced in *Escherichia coli*. Proc Natl Acad Sci USA 85:5879-5883.

Izbicki et al. (2002) Time Course of Bleomycin-Induced Lung Fibrosis. Int J Exp Pathol 83:111-119.

Jiang et al. (1994) Astrocytes Modulate Retinal Vasculogenesis: Effects on Fibronectin Expression. J Cell Sci 107:2499-2508.

Jones et al. (1986) Replacing the complementarity-determining regions in a human antibody with those from a mouse. Nature 321:522-525.

Karlin & Altschul (1990) Methods for assessing the statistical significance of molecular sequence features by using general scoring schemes. Proc Natl Acad Sci USA 87:2264-2268.

King et al. (2011) Idiopathic pulmonary fibrosis. Lancet 378(9807):1949-1961.

Karlin & Altschul (1993) Applications and statistics for multiple high-scoring segments in molecular sequences. Proc Natl Acad Sci USA 90:5873-5877.

Koenig et al. (2017) Mutational landscape of antibody variable domains reveals a switch modulating the inter-domain conformational dynamics and antigen binding. Proc Natl Acad Sci USA 114:486-495.

Kohler & Milstein (1975) Continuous cultures of fused cells secreting antibody of predefined specificity. Nature 256:495-497.

Kozbor & Roder (1983) The production of monoclonal antibodies from human lymphocytes. Immunology Today 4:72.

Krammer et al. (1999) Forced Unfolding of the Fibronectin Type III Module Reveals a Tensile Molecular Recognition Switch. Proc Natl Acad Sci USA 96:1351-1356.

Kuddannaya et al. (2013) Surface Chemical Modification of Poly(dimethylsiloxane) for the Enhanced Adhesion and Proliferation of Mesenchymal Stem Cells. ACS Appl Mater Interfaces 5:9777-9784.

Lawson et al. (2005) Increased and Prolonged Pulmonary Fibrosis in Surfactant Protein C-Deficient Mice Following Intratracheal Bleomycin. Am J Pathol 167:1267-1277.

Lee et al. (2007) Selection of Human Antibody Fragments by Phage Display. Nat Protoc 2:3001-3008.

Lemmon et al. (2011) Probing the Folded State of Fibronectin Type III Domains in Stretched Fibrils by Measuring Buried Cysteine Accessibility. J Biol Chem 286:26375-26382.

Li et al. (2005) Mechanical Unfolding Intermediates Observed by Single-Molecule Force Spectroscopy in a Fibronectin Type III Module. J Mol Biol 345:817-826.

Little et al. (2008) Assay to Mechanically Tune and Optically Probe Fibrillar Fibronectin Conformations from Fully Relaxed to Breakage. Matrix Biol 27:451-461.

Mardon & Grant (1994) The Role of the Ninth and Tenth Type III Domains of Human Fibronectin in Cell Adhesion. FEBS Lett 340:197-201.

Markowski et al. (2012) Directing Epithelial to Mesenchymal Transition Through Engineered Microenvironments Displaying Orthogonal Adhesive and Mechanical Cues. J Biomed Mater Res, Part A 100:2119-2127.

Marks et al. (1991) By-passing immunization: human antibodies from V-gene libraries displayed on phage. J Mol Biol 222:581-597.

Martino et al. (2009) Controlling Integrin Specificity and Stem Cell Differentiation in 2D and 3D Environments Through Regulation of Fibronectin Domain Stability. Biomaterials 30:1089-1097.

Moek et al. (2017) Theranostics Using Antibodies and Antibody-Related Therapeutics. J Nucl Med Off Publ Soc Nucl Med 58:83S-90S.

Morimoto & Inouye (1992) Single-step purification of F(ab')$_2$ fragments of mouse monoclonal antibodies (immunoglobulins G1) by hydrophobic interaction high performance liquid chromatography using TSKgel Phenyl-5PW. J Biochem Biophys Methods 24:107-117.

Morrison et al. (1984) Chimeric human antibody molecules: mouse antigen-binding domains with human constant region domains. Proc Natl Acad Sci USA. 81:6851-6855.

Morton & Myszka (1998) Kinetic analysis of macromolecular interactions using surface plasmon resonance biosensors. Methods Enzymol 295:268-294.

Morton et al. (1995) Interpreting complex binding kinetics from optical biosensors: a comparison of analysis by linearization, the integrated rate equation, and numerical integration. Anal Biochem 227(1):176-185.

Mould et al. (1997) Defining the Topology of Integrin alpha5beta1-Fibronectin Interactions Using Inhibitory Anti-alpha5 and Anti-beta1 Monoclonal Antibodies. Evidence that the Synergy Sequence of Fibronectin is Recognized by the Amino-Terminal Repeats of the alpha5 Subunit. J Biol Chem 272:17283-17292.

Myszka et al. (1998) CLAMP©: a biosensor kinetic data analysis program. Trends Biochem Sci 23(4):149-150.

National Heart, Lung, and Blood Institute. Idiopathic Pulmonary Fibrosis, available from the website of the National Heart, Lung, and Blood Institute (NHLBI).

Neuberger et al. (1984) Recombinant antibodies possessing novel effector functions. Nature 312:604-608.

Offord & Grens (2018) Directed Evolution, Phage Display Nab Chemistry Nobel. The Scientist Magazine, Oct. 3, 3018.

Pankov & Yamada (2002) Fibronectin at a glance. J Cell Sci 115:3861-3863.

Patan (2004) Vasculogenesis and Angiogenesis. Cancer Treat Res 117:3-32.

Paul (1993) *Fundamental Immunology*, 3rd Ed., Raven Press, New York, New York, United States of America.

PCT International Patent Application Publication Nos. WO 1992/02190; WO 1993/16185; WO 2007/019107; WO 2007/030652; WO 2007/089798; WO 2008/060374; WO 2018/088403.

Pitulescu et al. (2010) Inducible Gene Targeting in the Neonatal Vasculature and Analysis of Retinal Angiogenesis in Mice. Nat Protoc 5:1518-1534.

Presta (1992) Antibody engineering. Curr Op Struct Biol 2:593-596.

Presta et al. (1993) Humanization of an antibody directed against IgE. J Immunol 1993 151:2623.

Pulmonary Fibrosis Foundation (2018) What is Pulmonary Fibrosis. available from the website of the Pulmonary Fibrosis Foundation, Chicago, Illinois, United States of America.

Raghu & Mikacenic (2018) Pathogenesis of idiopathic pulmonary fibrosis. Available from the website of UPTODATE®, Wolters Kluwer, Riverwoods, Illinois, United States of America.

Riechmann et al. (1988) Reshaping human antibodies for therapy. Nature 332:323-327.

Rosano & Ceccarelli (2014) Recombinant protein expression in *Escherichia coli*: advances and challenges. Front Microbiol 5:Article 172.

Ruoslahti & Pierschbacher (1987) New Perspectives in Cell Adhesion: RGD and Integrins. Science 238:491-497.

Schornberg et al. (2009) Alpha5beta1-Integrin Controls Ebolavirus Entry by Regulating Endosomal Cathepsins. Proc Natl Acad Sci USA 106:8003-8008.

Shukla et al. (2013) Structure of Active Betaarrestin-1 Bound to a G-Protein-Coupled Receptor Phosphopeptide. Nature 497:137-141.

Sidhu (2001) Engineering M13 for phage display. Biomol Eng 18:57-63.

Sims et al. (1993) A humanized CD18 antibody can block function without cell destruction. J Immunol 151:2296-2308.

Skerra & Pluckthun (1988). Assembly of a Functional Immunoglobulin Fv Fragment in *Escherichia coli*. Science 240:1038.

Smith et al. (2007) Force-Induced Unfolding of Fibronectin in the Extracellular Matrix of Living Cells. PLoS Biol 5:2243-2254.

Stewart et al. (1984) in *Solid Phase Peptide Synthesis, 2nd Edition*, Pierce Chemical Company, Rockford, Illinois, United States of America.

Takeda et al. (1985) Construction of chimaeric processed immunoglobulin genes containing mouse variable and human constant region sequences. Nature 314:452-454.

Tobias (2014) Biomolecular binding kinetic assays on the octet platform. Forte Bio Appl Note 14:1-21.

Trafton (2010) Explained: Directed evolution. Speeding up protein evolution in the lab can yield useful molecules that nature never intended. MIT News May 13, 2010. Massachusetts Institute of Technology, Cambridge, Massachusetts, United States of America.

Tuszynski et al. (1988) Thrombospondin promotes platelet aggregation. Blood 72:109-115.

U.S. patent application Ser. No. 16/345,639.

U.S. Patent Application Publication Nos. 2002/0034765; 2003/0017534; 2003/0022244; 2003/0153043; 2004/0253645; 2006/0073137; 2018/0298087, 2018/0312588, 2018/0346564, 2019/0151448.

U.S. Pat. Nos. 4,554,101; 4,816,567; 4,946,778; 4,975,369; 5,001,065; 5,075,431; 5,081,235; 5,169,939; 5,202,238; 5,204,244; 5,225,539; 5,231,026; 5,292,867; 5,354,847; 5,436,157; 5,472,693; 5,482,856; 5,491,088; 5,500,362; 5,502,167; 5,530,101; 5,571,894; 5,585,089; 5,587,458; 5,641,870; 5,693,761; 5,693,762; 5,712,120; 5,714,350; 5,766,886; 5,770,196; 5,777,085; 5,821,123; 5,821,337; 5,869,619; 5,877,293; 5,886,152; 5,895,205; 5,929,212; 6,054,297; 6,180,370; 6,407,213; 6,479,284; 6,548,640;

6,632,927; 6,639,055; 6,677,436; 6,750,325; 6,797,492; 7,060,808; 7,906,625; 8,398,980; 8,436,150; 8,796,439; 10,253,111.

van der Walle et al. (2002) Novel Mutant Human Fibronectin FIII9-10 Domain Pair with Increased Conformational Stability and Biological Activity. Protein Eng 15:1021-1024.

Verhoeyen et al. (1988) Reshaping human antibodies: grafting an antilysozyme activity. Science 239:1534-1536.

Verma et al. (1998). Antibody engineering: Comparison of bacterial, yeast, insect and mammalian expression systems. Journal of Immunological Methods 216(1-2), 165-181.

Winter & Milstein (1991) Man-made antibodies. Nature 349:293-299.

Wright et al. (1992) Genetically engineered antibodies: progress and prospects. Critical Rev in Immunol 12(3,4): 125-168.

Zhu et al. (2008) Structure of a Complete Integrin Ectodomain in a Physiologic Resting State and Activation and Deactivation by Applied Forces. Mol Cell 32:849-861.

While the presently disclosed subject matter has been disclosed with reference to specific embodiments, it is apparent that other embodiments and variations of this presently disclosed subject matter may be devised by others skilled in the art without departing from the true spirit and scope of the presently disclosed subject matter.

SEQUENCE LISTING

```
Sequence total quantity: 37
SEQ ID NO: 1            moltype = DNA  length = 726
FEATURE                 Location/Qualifiers
misc_feature            1..726
                        note = Artificially synthesized H5 scFv sequence
source                  1..726
                        mol_type = other DNA
                        organism = synthetic construct
CDS                     1..726
SEQUENCE: 1
gaggtgcagc tgttggagtc tgggggaggc ttggtacagc ctgggggtc cctgagactc     60
tcctgtgcag cctctggatt cacctttagc agctatgcca tgagctgggt ccgccaggct   120
ccagggaagg ggctggagtg ggtctcagat atttatgatg gtggtggtac aaattacgca   180
gactccgtga agggccggtt caccacctcc agagacaatt ccaagaacac gctgtatctg   240
caaatgaaca gcctgagagc cgaggacacg gccgtatatt actgtgcgaa aactgctgat   300
aattttgact actggggcca gggaaccctg gtcaccgtct cgagcggtgg aggcggttca   360
ggcggaggtg gcagcggcgg tggcgggtcg acggacatcc agatgaccca gtctccatcc   420
tccctgtctg catctgtagg agacagagtc accatcactt gccgggcaag tcagagcatt   480
agcagctatt taaattggta tcagcagaaa ccagggaaag cccctaagct cctgatctat   540
gctgcatcca ctttgcaaag tggggtccca tcaaggttca gtggcagtgg atctgggaca   600
gatttcactc tcaccatcag cagtctgcaa cctgaagatt ttgcaactta ctactgtcaa   660
caggctaata gtgctcctac tacgttcggc caagggacca aggtggaaat caaacgggcg   720
gccgca                                                              726

SEQ ID NO: 2            moltype = AA  length = 242
FEATURE                 Location/Qualifiers
REGION                  1..242
                        note = Synthetic Construct
source                  1..242
                        mol_type = protein
                        organism = synthetic construct
SEQUENCE: 2
EVQLLESGGG LVQPGGSLRL SCAASGFTFS SYAMSWVRQA PGKGLEWVSD IYDGGGTNYA    60
DSVKGRFTTS RDNSKNTLYL QMNSLRAEDT AVYYCAKTAD NFDYWGQGTL VTVSSGGGGS   120
GGGGSGGGGS TDIQMTQSPS SLSASVGDRV TITCRASQSI SSYLNWYQQK PGKAPKLLIY   180
AASTLQSGVP SRFSGSGSGT DFTLTISSLQ PEDFATYYCQ QANSAPTTFG QGTKVEIKRA   240
AA                                                                 242

SEQ ID NO: 3            moltype = DNA  length = 792
FEATURE                 Location/Qualifiers
misc_feature            1..792
                        note = Artificially synthesized PelB + H5 scFv sequence
source                  1..792
                        mol_type = other DNA
                        organism = synthetic construct
CDS                     1..792
SEQUENCE: 3
atgaaatacc tattgcctac ggcagccgct ggattgttat tactcgcggc ccagccggcc     60
atggccgagg tgcagctgtt ggagtctggg ggaggcttgg tacagcctgg ggggtccctg   120
agactctcct gtgcagcctc tggattcacc tttagcagct atgccatgag ctgggtccgc   180
caggctccag ggaaggggct ggagtgggtc tcagatattt atgatggtgg tggtacaaat   240
tacgcagact ccgtgaaggg ccggttcacc acctccagag acaattccaa gaacacgctg   300
tatctgcaaa tgaacagcct gagagccgag gacacggccg tatattactg tgcgaaaact   360
gctgataatt ttgactactg gggccaggga accctggtca ccgtctcgag cggtggaggc   420
ggttcaggcg gaggtggcag cggcggtggc gggtcgacat ccagatgacc cagtctccatcc  unknown
```

```
cgggcggccg ca                                                              792

SEQ ID NO: 4              moltype = AA   length = 264
FEATURE                   Location/Qualifiers
REGION                    1..264
                          note = Synthetic Construct
source                    1..264
                          mol_type = protein
                          organism = synthetic construct
SEQUENCE: 4
MKYLLPTAAA GLLLLAAQPA MAEVQLLESG GGLVQPGGSL RLSCAASGFT FSSYAMSWVR   60
QAPGKGLEWV SDIYDGGGTN YADSVKGRFT TSRDNSKNTL YLQMNSLRAE DTAVYYCAKT  120
ADNFDYWGQG TLVTVSSGGG GSGGGGSGGG GSTDIQMTQS PSSLSASVGD RVTITCRASQ  180
SISSYLNWYQ QKPGKAPKLL IYAASTLQSG VPSRFSGSGS GTDFTLTISS LQPEDFATYY  240
CQQANSAPTT FGQGTKVEIK RAAA                                        264

SEQ ID NO: 5              moltype = AA   length = 264
FEATURE                   Location/Qualifiers
REGION                    1..264
                          note = Artificially synthesized 286 amino acid PelB + H5
                            sequence
source                    1..264
                          mol_type = protein
                          organism = synthetic construct
SEQUENCE: 5
MKYLLPTAAA GLLLLAAQPA MAEVQLLESG GGLVQPGGSL RLSCAASGFT FSSYAMSWVR   60
QAPGKGLEWV SDIYDGGGTN YADSVKGRFT TSRDNSKNTL YLQMNSLRAE DTAVYYCAKT  120
ADNFDYWGQG TLVTVSSGGG GSGGGGSGGG GSTDIQMTQS PSSLSASVGD RVTITCRASQ  180
SISSYLNWYQ QKPGKAPKLL IYAASTLQSG VPSRFSGSGS GTDFTLTISS LQPEDFATYY  240
CQQANSAPTT FGQGTKVEIK RAAA                                        264

SEQ ID NO: 6              moltype = AA   length = 264
FEATURE                   Location/Qualifiers
REGION                    1..264
                          note = Artificially synthesized PelB + H5 T931 sequence
source                    1..264
                          mol_type = protein
                          organism = synthetic construct
SEQUENCE: 6
MKYLLPTAAA GLLLLAAQPA MAEVQLLESG GGLVQPGGSL RLSCAASGFT FSSYAMSWVR   60
QAPGKGLEWV SDIYDGGGTN YADSVKGRFT TSRDNSKNTL YLQMNSLRAE DIAVYYCAKT  120
ADNFDYWGQG TLVTVSSGGG GSGGGGSGGG GSTDIQMTQS PSSLSASVGD RVTITCRASQ  180
SISSYLNWYQ QKPGKAPKLL IYAASTLQSG VPSRFSGSGS GTDFTLTISS LQPEDFATYY  240
CQQANSAPTT FGQGTKVEIK RAAA                                        264

SEQ ID NO: 7              moltype = AA   length = 5
FEATURE                   Location/Qualifiers
source                    1..5
                          mol_type = protein
                          organism = Homo sapiens
SEQUENCE: 7
PHSRN                                                               5

SEQ ID NO: 8              moltype = AA   length = 242
FEATURE                   Location/Qualifiers
REGION                    1..242
                          note = Artificially constructed consensus sequence
VARIANT                   41
                          note = Xaa can be Pro or Ser
VARIANT                   73
                          note = Xaa can be Asn or Asp
VARIANT                   78
                          note = Xaa can be Leu or Met
VARIANT                   96
                          note = Xaa can be Ala or Thr
VARIANT                   103
                          note = Xaa can be Asp or Tyr
source                    1..242
                          mol_type = protein
                          organism = synthetic construct
SEQUENCE: 8
EVQLLESGGG LVQPGGSLRL SCAASGFTFS SYAMSWVRQA XGKGLEWVSD IYDGGGTNYA   60
DSVKGRFTTS RDXSKNTXYL QMNSLRAEDT AVYYCXKTAD NFXYWGQGTL VTVSSGGGGS  120
GGGGSGGGGS TDIQMTQSPS SLSASVGDRV TITCRASQSI SSYLNWYQQK PGKAPKLLIY  180
AASTLQSGVP SRFSGSGSGT DFTLTISSLQ PEDFATYYCQ QANSAPTTFG QGTKVEIKRA  240
AA                                                                242

SEQ ID NO: 9              moltype = AA   length = 242
FEATURE                   Location/Qualifiers
```

```
REGION                       1..242
                             note = Artificially synthesized R1F8/R1H8 scFv sequence
source                       1..242
                             mol_type = protein
                             organism = synthetic construct
SEQUENCE: 9
EVQLLESGGG LVQPGGSLRL SCAASGFTFS SYAMSWVRQA PGKGLEWVSD IYDGGGTNYA    60
DSVKGRFTTS RDNSKNTLYL QMNSLRAEDT AVYYCTKTAD NFDYWGQGTL VTVSSGGGGS   120
GGGGSGGGGS TDIQMTQSPS SLSASVGDRV TITCRASQSI SSYLNWYQQK PGKAPKLLIY   180
AASTLQSGVP SRFSGSGSGT DFTLTISSLQ PEDFATYYCQ QANSAPTTFG QGTKVEIKRA   240
AA                                                                 242

SEQ ID NO: 10                moltype = AA  length = 242
FEATURE                      Location/Qualifiers
REGION                       1..242
                             note = Artificially synthesized R4B8 scFv sequence
source                       1..242
                             mol_type = protein
                             organism = synthetic construct
SEQUENCE: 10
EVQLLESGGG LVQPGGSLRL SCAASGFTFS SYAMSWVRQA PGKGLEWVSD IYDGGGTNYA    60
DSVKGRFTTS RDNSKNTLYL QMNSLRAEDT AVYYCTKTAD NFYYWGQGTL VTVSSGGGGS   120
GGGGSGGGGS TDIQMTQSPS SLSASVGDRV TITCRASQSI SSYLNWYQQK PGKAPKLLIY   180
AASTLQSGVP SRFSGSGSGT DFTLTISSLQ PEDFATYYCQ QANSAPTTFG QGTKVEIKRA   240
AA                                                                 242

SEQ ID NO: 11                moltype = AA  length = 242
FEATURE                      Location/Qualifiers
REGION                       1..242
                             note = Artificially synthesized R2G8 scFv sequence
source                       1..242
                             mol_type = protein
                             organism = synthetic construct
SEQUENCE: 11
EVQLLESGGG LVQPGGSLRL SCAASGFTFS SYAMSWVRQA SGKGLEWVSD IYDGGGTNYA    60
DSVKGRFTTS RDDSKNTLYL QMNSLRAEDT AVYYCAKTAD NFDYWGQGTL VTVSSGGGGS   120
GGGGSGGGGS TDIQMTQSPS SLSASVGDRV TITCRASQSI SSYLNWYQQK PGKAPKLLIY   180
AASTLQSGVP SRFSGSGSGT DFTLTISSLQ PEDFATYYCQ QANSAPTTFG QGTKVEIKRA   240
AA                                                                 242

SEQ ID NO: 12                moltype = AA  length = 242
FEATURE                      Location/Qualifiers
REGION                       1..242
                             note = Artificially synthesized R1H6 scFv sequence
source                       1..242
                             mol_type = protein
                             organism = synthetic construct
SEQUENCE: 12
EVQLLESGGG LVQPGGSLRL SCAASGFTFS SYAMSWVRQA PGKGLEWVSD IYDGGGTNYA    60
DSVKGRFTTS RDNSKNTMYL QMNSLRAEDT AVYYCAKTAD NFDYWGQGTL VTVSSGGGGS   120
GGGGSGGGGS TDIQMTQSPS SLSASVGDRV TITCRASQSI SSYLNWYQQK PGKAPKLLIY   180
AASTLQSGVP SRFSGSGSGT DFTLTISSLQ PEDFATYYCQ QANSAPTTFG QGTKVEIKRA   240
AA                                                                 242

SEQ ID NO: 13                moltype = DNA  length = 25
FEATURE                      Location/Qualifiers
misc_feature                 1..25
                             note = Artificially synthesized oligonucleotide primer
source                       1..25
                             mol_type = other DNA
                             organism = synthetic construct
SEQUENCE: 13
ccaaggcatg caaattctat ttcaa                                         25

SEQ ID NO: 14                moltype = DNA  length = 20
FEATURE                      Location/Qualifiers
misc_feature                 1..20
                             note = Artificially synthesized oligonucleotide primer
source                       1..20
                             mol_type = other DNA
                             organism = synthetic construct
SEQUENCE: 14
tggtgatgat gatgtgcggc                                               20

SEQ ID NO: 15                moltype = DNA  length = 20
FEATURE                      Location/Qualifiers
misc_feature                 1..20
                             note = Artificially synthesized oligonucleotide primer
source                       1..20
```

-continued

```
                        mol_type = other DNA
                        organism = synthetic construct
SEQUENCE: 15
gtgctgcttc cggatttacc                                                   20

SEQ ID NO: 16           moltype = DNA  length = 20
FEATURE                 Location/Qualifiers
misc_feature            1..20
                        note = Artificially synthesized oligonucleotide primer
source                  1..20
                        mol_type = other DNA
                        organism = synthetic construct
SEQUENCE: 16
tggtgatgat gatgtgcggc                                                   20

SEQ ID NO: 17           moltype = AA  length = 4
FEATURE                 Location/Qualifiers
REGION                  1..4
                        note = Artifical linker sequence
source                  1..4
                        mol_type = protein
                        organism = synthetic construct
SEQUENCE: 17
GGGG                                                                    4

SEQ ID NO: 18           moltype = AA  length = 5
FEATURE                 Location/Qualifiers
REGION                  1..5
                        note = Artificial linker sequence
source                  1..5
                        mol_type = protein
                        organism = synthetic construct
SEQUENCE: 18
SGGGG                                                                   5

SEQ ID NO: 19           moltype = AA  length = 49
FEATURE                 Location/Qualifiers
source                  1..49
                        mol_type = protein
                        organism = Homo sapiens
SEQUENCE: 19
DYEFLKSWTV EDLQKRLLAL DPMMEQEIEE IRQKYQSKRQ PILDAIEAK                   49

SEQ ID NO: 20           moltype = AA  length = 49
FEATURE                 Location/Qualifiers
source                  1..49
                        mol_type = protein
                        organism = Homo sapiens
SEQUENCE: 20
DFDFLKNLSL EELQMRLKAL DPMMEREIEE LRQRYTAKRQ PILDAMDAK                   49

SEQ ID NO: 21           moltype = AA  length = 49
FEATURE                 Location/Qualifiers
source                  1..49
                        mol_type = protein
                        organism = Homo sapiens
SEQUENCE: 21
GEVEWDAFSI PELQNFLTIL EKEEQDKIQQ VQKKYDKFRQ KLEEALRES                   49

SEQ ID NO: 22           moltype = AA  length = 49
FEATURE                 Location/Qualifiers
source                  1..49
                        mol_type = protein
                        organism = Homo sapiens
SEQUENCE: 22
GEVNWDAFSM PELHNFLRIL QREEEEHLRQ ILQKYSYSRQ KIQEALHAS                   49

SEQ ID NO: 23           moltype = AA  length = 49
FEATURE                 Location/Qualifiers
source                  1..49
                        mol_type = protein
                        organism = Homo sapiens
SEQUENCE: 23
HILKWELFQL ADLDTYQGML KLLFMKELEQ IVKMYEAYRQ ALLTELENR                   49

SEQ ID NO: 24           moltype = AA  length = 5
FEATURE                 Location/Qualifiers
REGION                  1..5
                        note = Artificial heavy chain CDR1
```

```
source                        1..5
                              mol_type = protein
                              organism = synthetic construct
SEQUENCE: 24
SYAMS                                                                    5

SEQ ID NO: 25                 moltype = AA  length = 16
FEATURE                       Location/Qualifiers
REGION                        1..16
                              note = Artificial heavy chain CDR2
source                        1..16
                              mol_type = protein
                              organism = synthetic construct
SEQUENCE: 25
DIYDGGGTNY ADSVKG                                                       16

SEQ ID NO: 26                 moltype = AA  length = 6
FEATURE                       Location/Qualifiers
REGION                        1..6
                              note = Artificial heavy chain CDR3 alternative 1
source                        1..6
                              mol_type = protein
                              organism = synthetic construct
SEQUENCE: 26
TADNFY                                                                   6

SEQ ID NO: 27                 moltype = AA  length = 6
FEATURE                       Location/Qualifiers
REGION                        1..6
                              note = Artificial heavy chain CDR3 alterantive 2
source                        1..6
                              mol_type = protein
                              organism = synthetic construct
SEQUENCE: 27
TADNFD                                                                   6

SEQ ID NO: 28                 moltype = AA  length = 11
FEATURE                       Location/Qualifiers
REGION                        1..11
                              note = Artificial light chain CDR1
source                        1..11
                              mol_type = protein
                              organism = synthetic construct
SEQUENCE: 28
RASQSISSYL N                                                            11

SEQ ID NO: 29                 moltype = AA  length = 7
FEATURE                       Location/Qualifiers
REGION                        1..7
                              note = Artificial light chain CDR2
source                        1..7
                              mol_type = protein
                              organism = synthetic construct
SEQUENCE: 29
AASTLQS                                                                  7

SEQ ID NO: 30                 moltype = AA  length = 9
FEATURE                       Location/Qualifiers
REGION                        1..9
                              note = Artificial light chain CDR3
source                        1..9
                              mol_type = protein
                              organism = synthetic construct
SEQUENCE: 30
QQANSAPTT                                                                9

SEQ ID NO: 31                 moltype = AA  length = 10
FEATURE                       Location/Qualifiers
REGION                        1..10
                              note = Artifical myc tag sequence
source                        1..10
                              mol_type = protein
                              organism = synthetic construct
SEQUENCE: 31
EQKLISEEDL                                                              10

SEQ ID NO: 32                 moltype = AA  length = 11
FEATURE                       Location/Qualifiers
REGION                        1..11
```

```
                              note = Artifical VSV tag sequence
source                        1..11
                              mol_type = protein
                              organism = synthetic construct
SEQUENCE: 32
YTDIEMNRLG K                                                              11

SEQ ID NO: 33                 moltype = AA  length = 6
FEATURE                       Location/Qualifiers
REGION                        1..6
                              note = Artificial His tag sequence
source                        1..6
                              mol_type = protein
                              organism = synthetic construct
SEQUENCE: 33
HHHHHH                                                                    6

SEQ ID NO: 34                 moltype = AA  length = 9
FEATURE                       Location/Qualifiers
REGION                        1..9
                              note = Artifical HA tag
source                        1..9
                              mol_type = protein
                              organism = synthetic construct
SEQUENCE: 34
YPYDVPDYA                                                                 9

SEQ ID NO: 35                 moltype = AA  length = 6
FEATURE                       Location/Qualifiers
REGION                        1..6
                              note = Artificial SortaseA tag
source                        1..6
                              mol_type = protein
                              organism = synthetic construct
SEQUENCE: 35
LPETGG                                                                    6

SEQ ID NO: 36                 moltype = AA  length = 22
FEATURE                       Location/Qualifiers
REGION                        1..22
                              note = Artificial PelB sequence
source                        1..22
                              mol_type = protein
                              organism = synthetic construct
SEQUENCE: 36
MKYLLPTAAA GLLLLAAQPA MA                                                  22

SEQ ID NO: 37                 moltype = AA  length = 5
FEATURE                       Location/Qualifiers
REGION                        1..5
                              note = Artificial linker sequence
source                        1..5
                              mol_type = protein
                              organism = synthetic construct
SEQUENCE: 37
NSAAH                                                                     5
```

What is claimed is:

1. An isolated and purified antibody comprising an amino acid sequence selected from the group consisting of SEQ ID NOs: 6 and 9-12, or an antigen-binding fragment thereof, wherein the antigen-binding fragment thereof selectively binds to a conformational state of fibronectin (FN) comprising FnIII9-4G-10 (4G).

2. The isolated and purified antibody of claim 1, wherein the fragment thereof comprises an scFv fragment.

3. A single chain variable fragment (scFv) polypeptide, comprising a $V_H$ segment comprising a first amino acid sequence selected from the group consisting of amino acids 26-135 of SEQ ID NO: 6 and amino acids 4-113 of any one of SEQ ID NOs: 9-12 and a $V_L$ segment comprising a second amino acid sequence selected from the group consisting of amino acids 131-237 of any one of SEQ ID NOs. 9-12, wherein the first and second amino acid sequences are joined by a linker peptide and further wherein the scFv polypeptide selectively binds to a conformational state of fibronectin (FN) comprising FnIII9-4G-10 (4G).

4. The scFv polypeptide of claim 3, wherein the linker peptide is a glycine-rich peptide.

5. The scFv polypeptide of claim 4, wherein the glycine-rich peptide comprises a concatemer of one, two, or three copies of SEQ ID NO: 17, a concatemer of one, two, or three copies of SEQ ID NO: 18, or a mixture of one, two, or three copies of SEQ ID NO: 17 and one, two, or three copies of SEQ ID NO: 18.

6. The scFv polypeptide of claim 3, further comprising at least two pairs of the $V_H$ segment and $V_L$ segment, wherein the at least two pairs are linked to form a multivalent scFv.

7. The scFv polypeptide of claim 3, wherein the scFv polypeptide is present in the pharmacologically acceptable carrier.

8. The scFv polypeptide of claim 3, wherein the scFv polypeptide is grafted into a human or humanized antibody.

\* \* \* \* \*